(12) United States Patent
Hansen et al.

(10) Patent No.: US 12,123,869 B2
(45) Date of Patent: Oct. 22, 2024

(54) RAPID AND SENSITIVE DETECTION AND QUANTIFICATION OF ANALYTES IN COMPLEX SAMPLES USING POLYMER-BASED METHODS

(71) Applicant: Children's Medical Center Corporation, Boston, MA (US)

(72) Inventors: Clinton H. Hansen, Cambridge, MA (US); Wesley Philip Wong, Cambridge, MA (US); Darren Yang, Somerville, MA (US); Andrew Ward, Everett, MA (US)

(73) Assignee: Children's Medical Center Corporation, Boston, MA (US)

( * ) Notice: Subject to any disclaimer, the term of this patent is extended or adjusted under 35 U.S.C. 154(b) by 94 days.

(21) Appl. No.: 16/088,006

(22) PCT Filed: Mar. 23, 2017

(86) PCT No.: PCT/US2017/023813
§ 371 (c)(1),
(2) Date: Sep. 24, 2018

(87) PCT Pub. No.: WO2017/165647
PCT Pub. Date: Sep. 28, 2017

(65) Prior Publication Data
US 2020/0116712 A1    Apr. 16, 2020

Related U.S. Application Data

(60) Provisional application No. 62/311,975, filed on Mar. 23, 2016, provisional application No. 62/355,285, filed on Jun. 27, 2016.

(51) Int. Cl.
*G01N 33/543* (2006.01)
*C12Q 1/6834* (2018.01)
*G01N 27/447* (2006.01)

(52) U.S. Cl.
CPC ..... *G01N 33/54313* (2013.01); *C12Q 1/6834* (2013.01); *G01N 27/44726* (2013.01); *G01N 27/44739* (2013.01)

(58) Field of Classification Search
CPC .......... C12Q 1/6834; G01N 27/44726; G01N 2458/10
See application file for complete search history.

(56) References Cited

U.S. PATENT DOCUMENTS

| 5,571,677 | A | 11/1996 | Gryaznov |
| 5,635,352 | A | 6/1997 | Urdea et al. |

(Continued)

FOREIGN PATENT DOCUMENTS

| JP | H06-508753 A | 10/1994 |
| JP | 2000-312589 A | 8/2000 |

(Continued)

OTHER PUBLICATIONS

Papadakis et al. Nano Lett. 2010. 10:5093-5097. (Year: 2010).*

(Continued)

*Primary Examiner* — Joseph G. Dauner
(74) *Attorney, Agent, or Firm* — Wolf, Greenfield & Sacks, P.C.

(57) ABSTRACT

Provided herein, inter alia, are improved methods for detecting analytes, including proteins and nucleic acids. In some instances, the analytes are detected in complex matrices such as serum.

20 Claims, 24 Drawing Sheets
Specification includes a Sequence Listing.

Secondary structure free in functionalization complementary oligos and target region at room temperature (25 °C)

(56) References Cited

U.S. PATENT DOCUMENTS

| | | | |
|---|---|---|---|
| 5,888,731 A | 5/1999 | Yager et al. | |
| 5,902,724 A | 5/1999 | Lane et al. | |
| 6,143,504 A | 11/2000 | Das et al. | |
| 6,232,066 B1 | 5/2001 | Felder et al. | |
| 6,251,660 B1 | 6/2001 | Muir et al. | |
| 6,569,306 B1 * | 5/2003 | Read | G01N 27/44704 |
| | | | 204/456 |
| 6,770,698 B1 | 8/2004 | Chu et al. | |
| 8,129,119 B2 | 3/2012 | Jarrell et al. | |
| 8,491,454 B2 | 7/2013 | Wong et al. | |
| 8,795,143 B2 | 8/2014 | Wong et al. | |
| 9,255,905 B1 | 2/2016 | Mellors et al. | |
| 9,914,958 B2 | 3/2018 | Wong et al. | |
| 9,994,839 B2 | 6/2018 | Lo et al. | |
| 10,919,037 B2 | 2/2021 | Wong et al. | |
| 10,948,401 B2 | 3/2021 | Yang et al. | |
| 11,198,900 B2 | 12/2021 | Koussa et al. | |
| 11,396,650 B2 | 7/2022 | Wong et al. | |
| 11,591,636 B2 | 2/2023 | Wong et al. | |
| 2002/0081744 A1 | 6/2002 | Chan et al. | |
| 2002/0182717 A1 | 12/2002 | Karlsson et al. | |
| 2003/0143549 A1 | 7/2003 | Yang et al. | |
| 2003/0186301 A1 | 10/2003 | Christian et al. | |
| 2006/0194240 A1 | 8/2006 | Arnold et al. | |
| 2006/0257958 A1 | 11/2006 | Bruno | |
| 2007/0026423 A1 | 2/2007 | Koehler et al. | |
| 2007/0037152 A1 | 2/2007 | Drmanac | |
| 2007/0117109 A1 | 5/2007 | Rothemund | |
| 2007/0154899 A1 | 7/2007 | Coull et al. | |
| 2007/0281367 A1 * | 12/2007 | Hennessy | C12Q 1/6816 |
| | | | 536/23.1 |
| 2008/0038725 A1 | 2/2008 | Luo et al. | |
| 2008/0131870 A1 | 6/2008 | Allawi et al. | |
| 2008/0312103 A1 | 12/2008 | Nemoto et al. | |
| 2009/0087838 A1 | 4/2009 | Reif et al. | |
| 2009/0286694 A1 | 11/2009 | Zainiev et al. | |
| 2010/0015608 A1 | 1/2010 | Kolpashchikov | |
| 2010/0035247 A1 | 2/2010 | Burton | |
| 2010/0206730 A1 | 8/2010 | Hunkapiller et al. | |
| 2010/0216658 A1 | 8/2010 | Chaput et al. | |
| 2011/0086774 A1 | 4/2011 | Dunaway | |
| 2011/0268654 A1 | 11/2011 | Hilderbrand et al. | |
| 2013/0004523 A1 | 1/2013 | Zubarev et al. | |
| 2013/0130884 A1 | 5/2013 | Wong et al. | |
| 2013/0196341 A1 | 8/2013 | Neely et al. | |
| 2013/0310260 A1 | 11/2013 | Kim et al. | |
| 2013/0344508 A1 | 12/2013 | Schwartz et al. | |
| 2014/0255939 A1 | 9/2014 | Wong et al. | |
| 2014/0284213 A1 | 9/2014 | Sabin et al. | |
| 2014/0302532 A1 | 10/2014 | Wilson et al. | |
| 2015/0027894 A1 | 1/2015 | Puleo et al. | |
| 2015/0093836 A1 | 4/2015 | Suzuki et al. | |
| 2015/0099650 A1 | 4/2015 | Sood et al. | |
| 2015/0292007 A1 | 10/2015 | Church et al. | |
| 2015/0361422 A1 | 12/2015 | Sampson et al. | |
| 2016/0186238 A1 | 6/2016 | Liu et al. | |
| 2017/0369935 A1 | 12/2017 | Koussa et al. | |
| 2018/0135043 A1 | 5/2018 | Wong et al. | |
| 2018/0223344 A1 | 8/2018 | Chandrasekaran et al. | |
| 2018/0291434 A1 | 10/2018 | Wong et al. | |
| 2019/0048409 A1 | 2/2019 | Wong et al. | |
| 2019/0070604 A1 | 3/2019 | Wong et al. | |
| 2020/0340033 A1 | 10/2020 | Wong et al. | |
| 2021/0239602 A1 | 8/2021 | Yang et al. | |
| 2023/0045556 A1 | 2/2023 | Wong et al. | |
| 2023/0146476 A1 | 5/2023 | MacDonald et al. | |

FOREIGN PATENT DOCUMENTS

| | | | |
|---|---|---|---|
| JP | 2003-219897 A | 8/2003 | |
| JP | 2005-536234 A | 12/2005 | |
| JP | 2008-259453 A | 10/2008 | |
| JP | 2009-521230 | 6/2009 | |
| WO | WO 93/01313 A1 | 1/1993 | |
| WO | WO 98/18961 A1 | 5/1998 | |
| WO | WO 00/40751 A2 | 7/2000 | |
| WO | WO 2004/016767 A2 | 2/2004 | |
| WO | WO 2007/076128 A2 | 7/2007 | |
| WO | WO-2009045906 A2 * | 4/2009 | C07K 14/003 |
| WO | WO 2011/005221 A1 | 1/2011 | |
| WO | WO 2011/153211 A1 | 12/2011 | |
| WO | WO 2012/058638 A2 | 5/2012 | |
| WO | WO-2012057689 A1 * | 5/2012 | C12Q 1/6804 |
| WO | WO 2013/010023 A2 | 1/2013 | |
| WO | WO-2013067489 A1 * | 5/2013 | C12Q 1/6813 |
| WO | WO 2014/011800 A1 | 1/2014 | |
| WO | WO-2014160192 A1 * | 10/2014 | C12Q 1/6804 |
| WO | WO 2015/006626 A1 | 1/2015 | |
| WO | WO 2015/040009 A1 | 3/2015 | |
| WO | WO 2015/164602 A2 | 10/2015 | |
| WO | WO 2016/089588 A1 | 6/2016 | |
| WO | WO 2016/164866 A1 | 10/2016 | |
| WO | WO-2016196824 A1 * | 12/2016 | C12N 15/111 |
| WO | WO 2017/003950 A2 | 1/2017 | |
| WO | WO 2017/147398 A1 | 8/2017 | |
| WO | WO-2017139409 A1 * | 8/2017 | G01N 33/5306 |
| WO | WO-2017165647 A1 * | 9/2017 | B01D 57/02 |
| WO | WO 2018/106721 A1 | 6/2018 | |
| WO | WO 2019/100080 A1 | 5/2019 | |

OTHER PUBLICATIONS

Fang et al. Sensors and Actuators B. 2018. 257:620-628. (Year: 2018).*
Ping. MRS Bulletin. 2017. 42:780. (Year: 2017).*
Porchetta et al. J Am Chem Soc. 2018. 140:947-953. (Year: 2018).*
Lubken et al. Nano Lett. 2020. 20:2296-2302. (Year: 2020).*
Chandrasekaran et al. ACS Sens. 2016. 1:120-123. (Year: 2016).*
Love et al. New Methods for the Study of Biomolecular Complexes. 1998. p. 171-179. (Year: 1998).*
International Search Report and Written Opinion for International Application No. PCT/US2017/023813 mailed Jun. 9, 2017.
International Preliminary Report on Patentability for International Application No. PCT/US2017/023813 mailed Oct. 4, 2018.
[No Author Listed], Wikipedia Entry, "Xhol." May 14, 2014. Retrieved from the internet. <https://en.wikipedia.org/w/index.php?title=Xhol&oldid=608536958>. Retrieved on Oct. 18, 2016.
Aaij et al., The gel electrophoresis of DNA. Biochim Biophys Acta. May 10, 1972;269(2):192-200.
Bellot et al., Recovery of intact DNA nanostructures after agarose gel-based separation. Nat Methods. Mar. 2011;8(3):192-4. doi: 10.1038/nmeth0311-192.
Bishop et al., Electrophoretic separation of viral nucleic acids on polyacrylamide gels. J Mol Biol. Jun. 28, 1967;26(3):373-87.
Bustamante et al., Entropic elasticity of lambda-phage DNA. Science. Sep. 9, 1994;265(5178):1599-600.
Bustamante et al., Ten years of tension: single-molecule DNA mechanics. Nature. Jan. 23, 2003;421(6921):423-7.
Butko et al., Detection of Ligand-Induced Conformational Changes in Oligonucleotides by Second-Harmonic Generation at a Supported Lipid Bilayer Interface. Anal Chem. Nov. 1, 2016;88(21):10482-10489. Epub Oct. 12, 2016. Accepted Manuscript, 23 pages.
Chandrasekaran et al., Label-free Detection of Specific Nucleic Acid Sequences using DNA Nanoswitches. The RNA Institute , University at Albany, State University of New York.
Chandrasekaran et al., Programmable DNA Nanoswitches for Detection of Nucleic Acid Sequences. ACS Sens., 2016, 1 (2), pp. 120-123.
Cheng et al., Early pregnancy factor in cervical mucus of pregnant women. Am J Reprod Immunol. Feb. 2004;51(2):102-5.
Chilkoti et al., Molecular Origins of the Slow Streptavidin-Biotin Dissociation Kinetics. J Am Chem Soc. 1995;117(43):10622-8.
Chivers et al., A streptavidin variant with slower biotin dissociation and increased mechanostability. Nat Methods. May 2010;7(5):391-3. doi: 10.1038/nmeth.1450. Epub Apr. 11, 2010.
Cho et al., A genomic-scale view of the cAMP response element-enhancer decoy: a tumor target-based genetic tool. Proc Natl Acad Sci U S A. Nov. 26, 2002;99(24):15626-31. Epub Nov. 18, 2002.

(56) References Cited

OTHER PUBLICATIONS

Conde et al., Implantable hydrogel embedded dark-gold nanoswitch as a theranostic probe to sense and overcome cancer multidrug resistance. Proc Natl Acad Sci U S A. Mar. 17, 2015;112(11):E1278-87. doi: 10.1073/pnas.1421229112. Epub Mar. 2, 2015.
Deniz et al., Single-molecule biophysics: at the interface of biology, physics and chemistry. J R Soc Interface. Jan. 6, 2008;5(18):15-45.
Devaraj et al., Biomedical applications of tetrazine cycloadditions. Acc Chem Res. Sep. 20, 2011;44(9):816-27. doi: 10.1021/ar200037t. Epub May 31, 2011.
Doshi et al., In vitro nanobody discovery for integral membrane protein targets. Sci Rep. Oct. 24, 2014;4:6760. doi: 10.1038/srep06760.
Douglas et al., A logic-gated nanorobot for targeted transport of molecular payloads. Science. Feb. 17, 2012;335(6070):831-4. doi: 10.1126/science.1214081.
Douglas et al., Self-assembly of DNA into nanoscale three-dimensional shapes. Nature. May 21, 2009;459(7245):414-8. doi: 10.1038/nature08016.
Evans et al., Dynamic strength of molecular adhesion bonds. Biophys J. Apr. 1997;72(4):1541-55.
Evans et al., Forces and bond dynamics in cell adhesion. Science. May 25, 2007;316(5828):1148-53.
Evans, Probing the relation between force—lifetime—and chemistry in single molecular bonds. Annu Rev Biophys Biomol Struct. 2001;30:105-28.
França et al., A review of DNA sequencing techniques. Q Rev Biophys. May 2002;35(2):169-200.
Green, Avidin and streptavidin. Methods Enzymol. 1990;184:51-67.
Greenleaf et al., High-resolution, single-molecule measurements of biomolecular motion. Annu Rev Biophys Biomol Struct. 2007;36:171-90.
Halvorsen et al., Binary DNA nanostructures for data encryption. PLoS One. 2012;7(9):e44212. doi: 10.1371/journal.pone.0044212. Epub Sep. 11, 2012.
Halvorsen et al., Cross-platform comparison of nucleic acid hybridization: toward quantitative reference standards. Anal Biochem. Nov. 15, 2014;465:127-33. doi: 10.1016/j.ab.2014.08.001. Epub Aug. 12, 2014.
Halvorsen et al., Massively Parallel Single-Molecule Manipulation Using Centrifugal Force. Biophys J. Jun. 2, 2010;98(11):L53-5.
Halvorsen et al., Nanoengineering a single-molecule mechanical switch using DNA self-assembly. Nanotechnology. Dec. 9, 2011;22(49):494005. doi: 10.1088/0957-4484/22/49494005. Epub Nov. 21, 2011.
Halvorsen, Probing Weak Single-Molecule Interactions: Development and Demonstration of a New Instrument. Boston University, College of Engineering dissertation. 2007: 102 pages.
Hanke et al., Entropy loss in long-distance DNA looping. Biophys J. Jul. 2003;85(1):167-73.
Hansen et al., Nanoswitch-linked immunosorbent assay (NLISA) for fast, sensitive, and specific protein detection. PNAS. Sep. 26, 2017;114(39):10367-10372. Supporting Information, 4 pages.
Hassur et al., UV shadowing—a new and convenient method for the location of ultraviolet-absorbing species in polyacrylamide gels. Anal Biochem. May 1974;59(1):162-4.
Hellman et al., Electrophoretic mobility shift assay (EMSA) for detecting protein-nucleic acid interactions. Nat Protoc. 2007;2(8):1849-61.
Idili et al., Programmable pH-triggered DNA nanoswitches. J Am Chem Soc. Apr. 23, 2014;136(16):5836-9. doi: 10.1021/ja500619w. Epub Apr. 9, 2014. Abstract only.
Jones et al., Nanomaterials. Programmable materials and the nature of the DNA bond. Science. Feb. 20, 2015;347(6224):1260901. doi: 10.1126/science.1260901.
Jung et al., Binding and Dissociation Kinetics of Wild-Type and Mutant Streptavidins on Mixed Biotin-Containing Alkylthiolate Monolayers. Langmuir. Nov. 28, 2000;16(24): 9421-32.
Khalil et al., Single M13 bacteriophage tethering and stretching. Proc Natl Acad Sci U S A. Mar. 20, 2007;104(12):4892-7. Epub Mar. 13, 2007.
Kim et al., A mechanically stabilized receptor-ligand flex-bond important in the vasculature. Nature. Aug. 19, 2010;466(7309):992-5. doi: 10.1038/nature09295.
Kleiner et al., Small-molecule discovery from DNA-encoded chemical libraries. Chem Soc Rev. Dec. 2011;40(12):5707-17. doi: 10.1039/c1cs15076f. Epub Jun. 14, 2011.
Klumb et al., Energetic roles of hydrogen bonds at the ureido oxygen binding pocket in the streptavidin-biotin complex. Biochemistry. May 26, 1998;37(21):7657-63.
Koch et al., Prospects and limitations of the rosette inhibition test to detect activity of early pregnancy factor in the pig. J Reprod Fertil. May 1985;74(1):29-38.
Koussa et al., DNA nanoswitches: a quantitative platform for gel-based biomolecular interaction analysis. Nat Methods. Feb. 2015;12(2):123-6. doi: 10.1038/nmeth.3209. Epub Dec. 8, 2014.
Koussa et al., Protocol for sortase-mediated construction of DNA-protein hybrids and functional nanostructures. Methods. May 15, 2014;67(2):134-41. doi: 10.1016/j.ymeth.2014.02.020. Epub Feb. 22, 2014.
Kufer et al., Single-molecule cut-and-paste surface assembly. Science. Feb. 1, 2008;319(5863):594-6. doi: 10.1126/science.1151424.
Leier et al., Cryptography with DNA binary strands. Biosystems. Jun. 2000;57(1):13-22.
McDonell et al., Analysis of restriction fragments of T7 DNA and determination of molecular weights by electrophoresis in neutral and alkaline gels. J Mol Biol. Feb. 15, 1977;110(1):119-46.
Modi et al., A DNA nanomachine that maps spatial and temporal pH changes inside living cells. Nat Nanotechnol. May 2009;4(5):325-30. doi: 10.1038/nnano.2009.83. Epub Apr. 6, 2009. Abstract only.
Morton et al., Rosette inhibition test: A multicentre investigation of early pregnancy factor in humans. J Reprod Immunol. Sep. 1982;4(5):251-61.
Morton et al., Early pregnancy factor. Semin Reprod Endocrinol. May 1992;10:72-82.
Neuman et al., Single-molecule force spectroscopy: optical tweezers, magnetic tweezers and atomic force microscopy. Nat Methods. Jun. 2008;5(6):491-505. doi: 10.1038/nmeth.1218.
Park et al., Dual blockade of cyclic AMP response element—(CRE) and AP-1-directed transcription by CRE-transcription factor decoy oligonucleotide. gene-specific inhibition of tumor growth. J Biol Chem. Jan. 15, 1999;274(3):1573-80.
Pei et al, A DNA nanostructure-based biomolecular probe carrier platform for electrochemical biosensing. Adv Mater. Nov. 9, 2010;22(42):4754-8. doi: 10.1002/adma.201002767.
Quek et al., Mechanically controlled binary conductance switching of a single-molecule junction. Nat Nanotechnol. Apr. 2009;4(4):230-4. doi: 10.1038/nnano.2009.10. Epub Mar. 1, 2009.
Ritort, Single-molecule experiments in biological physics: methods and applications. J Phys Condens Matter. Aug. 16, 2006;18(32):R531-83. doi:10.1088/0953-8984/18/32/R01. Epub Jul. 25, 2006.
Rothemund, Folding DNA to create nanoscale shapes and patterns. Nature. Mar. 16, 2006;440(7082):297-302.
Sacca et al., DNA origami: the art of folding DNA. Angew Chem Int Ed Engl. Jan. 2, 2012;51(1):58-66. doi: 10.1002/anie.201105846. Epub Dec. 7, 2011.
Seeman, DNA in a material world. Nature. Jan. 23, 2003;421(6921):427-31.
Seeman, Nanomaterials based on DNA. Annu Rev Biochem. 2010;79:65-87. doi: 10.1146/annurev-biochem-060308-102244.
Shroff et al., Biocompatible force sensor with optical readout and dimensions of 6 nm3. Nano Lett. Jul. 2005;5(7):1509-14.
Shroff et al., Optical measurement of mechanical forces inside short DNA loops. Biophys J. Mar. 15, 2008;94(6):2179-86. Epub Dec. 7, 2007.
Smith et al., Overstretching B-DNA: the elastic response of individual double-stranded and single-stranded DNA molecules. Science. Feb. 9, 1996;271(5250):795-9.
Strunz et al., Dynamic force spectroscopy of single DNA molecules. Proc Natl Acad Sci U S A. Sep. 28, 1999;96(20):11277-82.

(56) References Cited

OTHER PUBLICATIONS

Su et al., Nucleic acid fluorescent probes for biological sensing. Appl Spectrosc. Nov. 2012;66(11):1249-62. doi: 10.1366/12-06803. Review.

Svoboda et al., Direct observation of kinesin stepping by optical trapping interferometry. Nature. Oct. 21, 1993;365(6448):721-7.

Thorne, Electrophoretic separation of polyoma virus DNA from host cell DNA. Virology. Jun. 1966;29(2):234-9.

Thuring et al., A freeze-squeeze method for recovering long DNA from agarose gels. Anal Biochem. May 26, 1975;66(1):213-20.

Wiita et al., Force-dependent chemical kinetics of disulfide bond reduction observed with single-molecule techniques. Proc Natl Acad Sci U S A. May 9, 2006;103(19):7222-7. Epub Apr. 27, 2006.

Winfree et al., Design and self-assembly of two-dimensional DNA crystals. Nature. Aug. 6, 1998;394(6693):539-44.

Wong et al., The effect of integration time on fluctuation measurements: calibrating an optical trap in the presence of motion blur. Opt Express. Dec. 11, 2006;14(25):12517-31.

Yang et al., Multiplexed single-molecule force spectroscopy using a centrifuge. Nat Commun. Mar. 17, 2016;7:11026(1-7). doi: 10.1038/ncomms11026.

Zadeh et al., NUPACK: Analysis and design of nucleic acid systems. J Comput Chem. Jan. 15, 2011;32(1):170-3. doi: 10.1002/jcc.21596.

Zhang et al., Mechanoenzymatic cleavage of the ultralarge vascular protein, von Willebrand Factor. Science. Jun. 5, 2009;324(5932):1330-4.

Zheng et al., From molecular to macroscopic via the rational design of a self-assembled 3D DNA crystal. Nature. Sep. 3, 2009;461(7260):74-7. doi: 10.1038/nature08274.

Hopwood et al., Integrated microfluidic system for rapid forensic DNA analysis: sample collection to DNA profile. Anal Chem. Aug. 15, 2010;82(16):6991-9. doi: 10.1021/ac101355r.

Yang et al., An integratable microfluidic cartridge for forensic swab samples lysis. Forensic Sci Int Genet. Jan. 2014;8(1):147-58. doi: 10.1016/j.fsigen.2013.08.012. Epub Sep. 8, 2013.

Ando et al., Single-nanoparticle tracking with angstrom localization precision and microsecond time resolution. Biophys J. Dec. 18, 2018;115(12):2413-2427. Epub Nov. 17, 2018.

Baslé et al., Protein chemical modification on endogenous amino acids. Chem Biol. Mar. 26, 2010;17(3):213-27.

Cheezum et al., Quantitative comparison of algorithms for tracking single fluorescent particles. Biophys J. Oct. 2001;81(4):2378-88.

Fu et al., Flow-induced elongation of von Willebrand factor precedes tension-dependent activation. Nat Commun. Aug. 23, 2017;8(1):324.

Horn et al., Forks and combs and DNA: the synthesis of branched oligodeoxyribonucleotides. Nucleic Acids Res. Sep. 12, 1989;17(17):6959-67.

Jiang et al., Electrostatic steering enables flow-activated von willebrand factor to bind platelet glycoprotein, revealed by single-molecule stretching and imaging. J Mol Biol. Mar. 29, 2019;431(7):1380-1396. Epub Feb. 22, 2019.

Jiang et al., Stretching DNA to twice the normal length with single-molecule hydrodynamic trapping. Lab Chip. May 19, 2020;20(10):1780-1791.

Mendoza et al., Probing protein structure by amino acid-specific covalent labeling and mass spectrometry. Mass Spectrom Rev. Sep.-Oct. 2009;28(5):785-815.

Pinheiro et al., Challenges and opportunities for structural DNA nanotechnology. Nat Nanotechnol. Nov. 6, 2011;6(12):763-72.

Silver et al., Tethered-bead, immune sandwich assay. Biosens Bioelectron. Jan. 15, 2015;63:117-123. Epub Jul. 11, 2014.

Thompson et al., Precise nanometer localization analysis for individual fluorescent probes. Biophys J. May 2002;82(5):2775-83.

Ueno et al., Simple dark-field microscopy with nanometer spatial precision and microsecond temporal resolution. Biophys J. May 19, 2010;98(9):2014-23.

Van Oijen et al., Single-molecule kinetics of lambda exonuclease reveal base dependence and dynamic disorder. Science. Aug. 29, 2003;301(5637):1235-8.

Yang et al., Repurposing a Benchtop Centrifuge for High-Throughput Single-Molecule Force Spectroscopy. Methods Mol Biol. 2018;1665:353-366.

\* cited by examiner

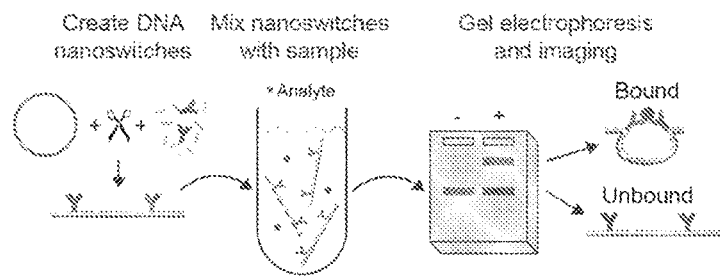
Figure 1
Figure 2A
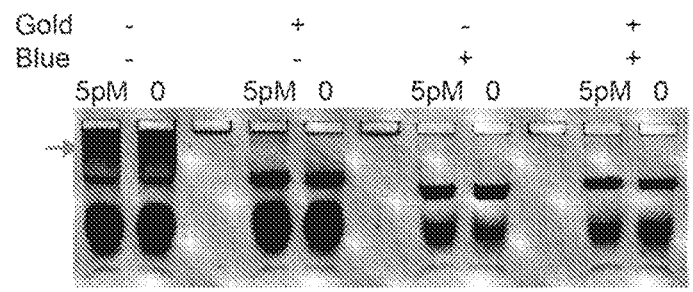
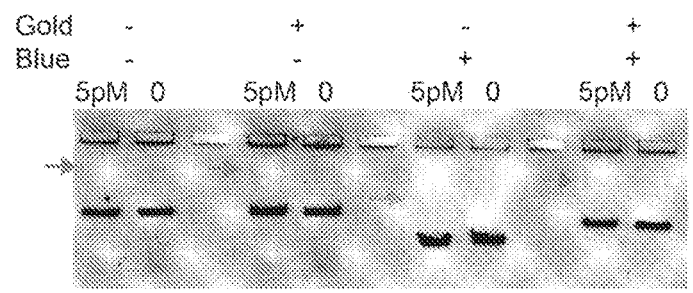
Figure 2B

RAPID AND SENSITIVE DETECTION AND QUANTIFICATION OF ANALYTES IN COMPLEX SAMPLES USING POLYMER-BASED METHODS

RELATED APPLICATIONS

This application is a national stage filing under 35 U.S.C. § 371 of International Patent Application Serial No. PCT/US2017/023813, filed Mar. 23, 2017, entitled "RAPID AND SENSITIVE DETECTION AND QUANTIFICATION OF ANALYTES IN COMPLEX SAMPLES USING POLYMER-BASED METHODS", which claims the benefit under 35 U.S.C. § 119(e) of U.S. Provisional Application Ser. No. 62/311,975, filed on Mar. 23, 2016, entitled "RAPID AND SENSITIVE QUANTIFICATION OF ANALYTE IN COMPLEX SAMPLES USING POLYMER-BASED METHODS" and of U.S. Provisional Application Ser. No. 62/355,285, filed on Jun. 27, 2016, entitled "RAPID AND SENSITIVE DETECTION AND QUANTIFICATION OF ANALYTES IN COMPLEX SAMPLES USING POLYMER-BASED METHODS", the entire contents of each of which are incorporated by reference herein.

REFERENCE TO A SEQUENCE LISTING SUBMITTED AS A TEXT FILE VIA EFS-WEB

The instant application contains a Sequence Listing which has been submitted in ASCII format via EFS-Web and is hereby incorporated by reference in its entirety. Said ASCII copy, created on Sep. 24, 2018, is named C123370102US02-SEQ-MAT and is 3,331 bytes in size.

BACKGROUND

Sensing platforms to detect and quantify specific proteins have found widespread use in both medical and research applications (Banoo et al. 2006). The traditional sandwich enzyme-linked immunosorbent assay (ELISA) uses an immobilized antibody to capture the target analyze and an enzyme-linked secondary antibody to bind the captured analyte for detection (Lequin et al. 2005). Despite numerous advances, the standard ELISA technique is still in widespread use due to ease-of-use, low cost per sample, and low instrumental costs.

SUMMARY

This disclosure provides, inter alia, an improved method for detecting an analyte in a sample. This method uses polymers that change configuration upon analyte binding, and that then are separated from each other via gel electrophoresis, each migrating a distinct distance through the gel. The techniques described herein can be applied to any detection technique that involves (1) gel electrophoresis of large nucleic acids or polymers with modifications and (2) quantification of a band to determine the amount of material within a sample. Such methods include but are not limited to the joining of two polymers in the presence of an analyte (but not in the absence of the analyte) or the creation of a loop within a polymer in the presence of an analyte (but not in the absence of the analyte), for example, which may be regarded as "analyte sandwiching". Such polymers or polymer pairs (or polymer systems) are regarded herein as nanoswitches. An exemplary technique uses nucleic acid, such as DNA, nanoswitches to assay the presence and/or amount of nucleic acids or protein targets. In some embodiments, the sample being tested is or comprises a complex matrix, such as serum or urine. The method may therefore involve assay of analytes, such as but not limited to proteins, in complex matrices, such as serum or urine. The nanoswitch is able to detect molecular associations between proteins and/or small molecules (Koussa et al. 2015). Such association is detected via a topological change in the nanoswitch structure from a linear to a more slowly migrating form such as but not limited to a looped form, which is imaged after gel electrophoresis.

Thus provided in one aspect is a method for detecting an analyte in a sample comprising (1) combining a sample with a first polymer and a second polymer, each conjugated, directly or indirectly, to an analyte-specific binding partner, under conditions that allow binding of analyte-specific binding partners to respective analytes, wherein the analyte-specific binding partners are able to bind to a single analyte simultaneously, and (2) detecting a complex formed by the binding of the first polymer and the second polymer to an analyte in the sample, wherein presence of the complex is indicative of presence of the analyte in the sample, wherein the sample is a complex sample, wherein the sample and polymers are combined in the presence of EDTA and a charged protein binding dye. The first polymer is conjugated to a first analyte-specific binding partner and the second polymer is conjugated to a second analyte-specific binding partner.

In some embodiments, the first and second polymers are nucleic acids, such as but not limited to DNA, and the sample and first and second polymers are combined in the presence of a nucleic acid binding dye, EDTA and a charged protein binding dye.

Provided in another aspect is a method for detecting an analyte in a sample comprising (1) combining a sample with a nucleic acid conjugated, directly or indirectly, to a first analyte-specific binding partner and a second analyte-specific binding partner, under conditions that allow binding of the first and second analyte-specific binding partners to their respective analytes, wherein the analyte-specific binding partners are able to bind to the same single analyte simultaneously, and (2) detecting the nucleic acid in a looped conformation formed by the binding of the first analyte-specific binding partner and the second analyte-specific binding partner to the same single analyte in the sample, wherein presence of the looped conformation is indicative of presence of the analyte in the sample, wherein the sample is a complex sample, wherein the sample and the nucleic acids are combined in the presence of EDTA, a nucleic acid binding dye, and a charged protein binding dye. In some embodiments, the first and second binding partners are conjugated to first and second oligonucleotides that are hybridized to the nucleic acid.

In some embodiments, the sample is a serum sample. In some embodiments, the sample is a blood sample. In some embodiments, the sample is a filtered blood sample. In some embodiments, the sample is a lysed blood sample.

In some embodiments, the protein binding dye is negatively charged. In some embodiments, the protein binding dye is positively charged. In some embodiments, the protein binding dye is Coomassie Blue.

In some embodiments, the nucleic acid binding dye is SYBR-Gold.

In some embodiments, the analyte is a low abundance analyte.

In some embodiments, the nucleic acid binding dye is SYBR-Gold, the protein binding dye is Coomassie Blue, the analyte is EPF, and the sample is a urine sample.

In some embodiments, the first and second analyte-specific binding partners are identical, for example identical in nature or type (e.g., both antibodies) and/or identical in binding specificity. In some embodiments, the first and second analyte-specific binding partners recognize and bind the same analyte (e.g., they both bind to early pregnancy factor). In related embodiments, the first and second analyte-specific binding partners have the same affinity and avidity for the same analyte. In some embodiments, the first and second analyte-specific binding partners bind to an identical epitope that is present at least twice in an analyte.

In some embodiments, the first and second analyte-specific binding partners are different. In some embodiments, the first and second analyte-specific binding partners bind to different epitopes of an analyte (i.e., of the same analyte).

In some embodiments, the first and second analyte-specific binding partners are antibodies. In some embodiments, the first and second analyte-specific binding partners are antigen-binding antibody fragments. In some embodiments, one or both of the analyte-specific binding partners are aptamers. In some embodiments, the analyte-specific binding partners are located at about the mid-point along the length of the first or second polymer.

In some embodiments, the first polymer and/or the second polymer is a nucleic acid. In some embodiments, the first polymer and/or the second polymer comprises M13 DNA. In some embodiments, the nucleic acid comprises M13 DNA.

In some embodiments, the method detects an analyte that is present at less than 100 or less than 10 copies in a sample.

Another aspect of this disclosure provides a method for identifying an agent that modifies the structure of an analyte comprising providing an analyte conjugated to a first and a second oligonucleotide (referred to as the "oligonucleotide-conjugated analyte"), hybridizing the oligonucleotide-conjugated analyte to a scaffold nucleic acid, wherein the first and the second oligonucleotides respectively hybridize to a first and a second target region in the scaffold nucleic acid, wherein the first and second target regions are spaced apart from each other, optionally wherein the scaffold nucleic acid is hybridized to a plurality of unconjugated oligonucleotides at non-target regions, thereby forming a looped nanoswitch, exposing the looped nanoswitch to an agent, detecting and/or measuring looped nanoswitches and linear nanoswitches using gel electrophoresis, wherein presence of linear nanoswitches indicates that the agent affects the structure of the analyte.

In some embodiments, the agent is an enzyme. In some embodiments, the analyte is a protein and the agent is a protease.

Another aspect of this disclosure provides a method for detecting an analyte in a sample comprising providing a nanoswitch comprising a scaffold nucleic acid hybridized to one or a plurality of oligonucleotides (referred to as "non-functionalized oligonucleotides" also referred to herein as "unfunctionalized oligonucleotides") and having a first and a second single stranded target region, hybridizing the nanoswitch to a first and a second functionalized oligonucleotide, each comprising an oligonucleotide conjugated to an analyte-specific binding partner (the "first" and "second" analyte-specific binding partners), wherein the first and second oligonucleotides respectively have nucleotide sequences that are complementary to the first and second single stranded target regions, to form a functionalized nanoswitch, combining the functionalized nanoswitch with a sample, wherein the analyte-specific binding partners are able to bind to the same single analyte simultaneously, detecting a looped nanoswitch formed by the binding of the first and second analyte-specific binding partners to the same analyte in the sample, wherein presence of the looped nanoswitch is indicative of presence of the analyte in the sample. The method may comprise a number of modifications or variations selected from the following: In some embodiments, hybridization of the functional oligonucleotides to the nanoswitch occurs at a temperature in the range of 20-30° C. and the functionalized oligonucleotides and target regions are chosen to have secondary structure free sequences in that temperature range, optionally wherein the temperature is room temperature.

In some embodiments, the functionalized oligonucleotides are purified, optionally by gel electrophoresis, prior to hybridizing with the nanoswitch.

In some embodiments, the nanoswitch is purified, optionally by gel electrophoresis, prior to hybridizing with the functionalized oligonucleotides.

In some embodiments, the scaffold nucleic acid is purified, optionally by gel electrophoresis, prior to hybridizing with the one or plurality of oligonucleotides. In some embodiments, the functionalized oligonucleotides are formed using (a) a copper-free click chemical reaction between each analyte-specific binding partner and the oligonucleotide to be functionalized, optionally wherein the copper-free click chemical reaction uses copper-free click bifunctional reagents comprising maleimide or N-hydroxysuccinimidyl ester groups that react with sulfhydryl or amine groups respectively, or (b) a fusion protein comprising the analyte-specific binding partner conjugated to a Snap-tag or a Halo-tag and oligonucleotides conjugated to Snap or Halo ligands.

One or any combination of the foregoing embodiments may be used together.

In some embodiments, purification by gel electrophoresis of the scaffold nucleic acid, the functionalized oligonucleotides, the nanoswitch, and/or the looped nanoswitch comprises dye-free gel electrophoresis, and optionally is real-time continuous gel electro-elution or reverse gel electro-elution.

Another aspect of this disclosure provides an apparatus for purifying a component from a sample having one or more components via gel electrophoresis, the apparatus comprising: a chamber; a gel disposed in the chamber, the gel having first and second wells, the second well being positioned downstream of the first well, the sample being loaded into the first well, the component arranged to migrate from the first well to the second well, wherein the apparatus is arranged to aspirate fluid from the second well, the aspirated fluid including the component.

In some embodiments, the apparatus is arranged to continuously aspirate fluid from the second well.

In some embodiments, fluid is continuously aspirated into one or more fractions.

In some embodiments, the apparatus further comprises a fluid-flow device arranged to aspirate fluid from the second well. In some embodiments, the fluid-flow device is arranged to supply a second fluid to the second well. In some embodiments, wherein the fluid-flow device comprises first and second tubes, the first tube arranged to transfer the fluid from the second well to a fraction, the second tube arranged to transfer the second fluid from a fluid supply to the second well.

In some embodiments, the apparatus further comprises first and second electrodes, the first and second electrodes arranged to produce an electric field, the component migrating towards the second well in response to the electric field.

In some embodiments, the chamber is filled with a buffer. In some embodiments, the chamber is filled with a buffer and the second fluid includes a second buffer, the second buffer being different from the buffer. In some embodiments, the chamber is filled with a buffer and the second fluid includes a second buffer, the second buffer being the same as the buffer.

In some embodiments, the apparatus is arranged to aspirate the fluid after 10 minutes, 20 minutes, 30 minutes, 1 hour, or longer.

In some embodiments, the gel is positioned on a tray disposed in the chamber.

In some embodiments, the fluid-flow device comprises first and second pumps for transferring fluid in the first and second tubes, respectively.

Another aspect of this disclosure provides a method of purifying a component from a sample having one or more components via gel electrophoresis, the method comprising: inserting a sample into a first well of a gel placed in a chamber, the gel having a second well located downstream of the first well; applying an electric field to cause the component to migrate from the first well to the second well; aspirating fluid from the second well, the fluid having the component.

In some embodiments, the step of aspirating the fluid from the second well includes continuously aspirating the fluid from the second well. In some embodiments, the step of continuously aspirating the fluid includes continuously aspirating the fluid into one or more fractions.

In some embodiments, the step of applying the electric field includes applying the electric field to cause a second component to migrate from the first well, the second component migrating to a position in between the first well and the second well.

In some embodiments, the method further comprises after the step of aspirating the fluid from the second well, applying the electric field to cause the second component to migrate to the second well; aspirating fluid from the second well, the fluid having only the second component.

In some embodiments, the method further comprises transferring a fluid into the second well.

In some embodiments, the step of transferring the fluid includes transferring a buffer into the second well.

Another aspect of this disclosure provides a method of purifying a component from a sample having one or more components via gel electrophoresis, the method comprising: inserting a sample into a well of a gel, the gel having first and second gel sections, the well being located in the first gel section; applying an electric field to cause first and second components to migrate from the first well, the second component migrating from the well to the second gel section; removing the second gel section; applying a second, opposite, electric field to cause a first component to migrate back to the well; aspirating fluid from the well, the fluid having the first component.

In some embodiments, the step of aspirating fluid includes continuously aspirating fluid from the well.

In some embodiments, the method further comprises adding a tracking dye to the well, the tracking dye arranged to migrate in between the first and second components; wherein the step of removing the second gel section includes removing the second gel section when the tracking dye is located in the second gel section.

In some embodiments, the method further comprises adding a tracking dye to a second well, the second well positioned adjacent to the well in the first gel section, the tracking dye arranged to migrate to a position located in between the first and second components; wherein the step of removing the second gel includes removing the second gel section when the tracking dye is located in the second gel section.

In some embodiments, the method further comprises adding a dye-stained sample to a second well, the second well positioned adjacent to the well in the first gel section, the dye-stained sample including a dyed first component and a dyed second component; wherein the step of removing the second gel section includes removing the second gel section when the dyed second component is located in the second gel section.

These and other aspects and embodiments of this disclosure will be described in greater detail herein.

BRIEF DESCRIPTION OF DRAWINGS

FIG. 1. Schematic of a nucleic acid, such as DNA, nanoswitch detection technique.

FIGS. 2A and 2B. Use of dyes to enable entry of nanoswitches into the agarose gel for separation. Gel electrophoresis results of 5 pM or 0 pM of PSA in fetal bovine serum (FIG. 2A) or bovine urine (FIG. 2B) in the absence of any dyes, only SYBR gold, only Coomassie Brilliant Blue G-250, or both SYBR gold and Coomassie Brilliant Blue G-250, as described in Online Methods. The locations of the looped bands are specified by the orange arrows.

DETAILED DESCRIPTION

Figure 3:
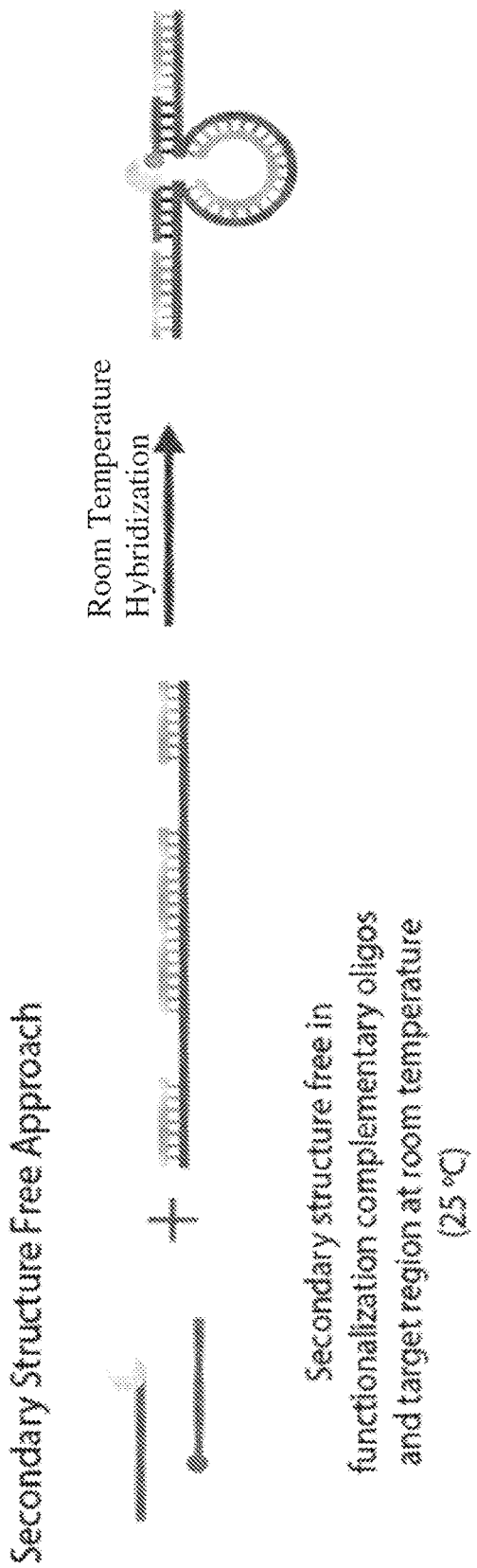
FIG. 3. Schematic of the secondary structure free approach. The target regions on the backbone or scaffold nucleic acid and their complementary oligonucleotides are designed to have no secondary structure at a temperature that does not affect the analyte of interest (e.g., does not affect the structure and/or activity of the analyte of interest), including for example at room temperature or physiological temperature, hence they can hybridize without the need for temperature ramping which may degrade the analyte structure and/or activity.

The disclosure provides, in part, improvements to analyte detection methods such as protein and nucleic acid detection methods that involve polymer-based gel electrophoresis techniques. The methods may be performed in a laboratory setting or as a point-of-care device or in a high-throughput analyzer in medical applications. Significantly, in some aspects provided herein, the methods may be used to detect analytes such as proteins in complex matrices (complex samples) that may for example comprise high concentration of non-analyte protein and other components that might otherwise interfere with the assay, particularly the assay of low concentration analyte.

These improved assays have been shown to have high sensitivity (e.g., sensitivity down to 100 fM in some instances). Thus they are particularly suited to assays of low concentration analytes that have heretofore not been easily or reproducibly assayed. One example of a low concentration analyte is early pregnancy factor (EPF). The ability to assay EPF, particularly at times when it is present in low concentrations, may allow for earlier detection of pregnancy.

The disclosure also provides, in part, improvements relating to the synthesis of nucleic acid nanoswitches, including selection of linear scaffold regions as points of attachment for analyte-specific binding partners and improved methodology for conjugating analyte-specific binding partners to oligonucleotides (that will then be hybridized to a scaffold nucleic acid), as well as improved methods for purifying nanoswitches and the various reactants that combine to form them. Provided herein are devices and methods for purifying linear scaffolds, oligonucleotides, and looped and linear nanoswitches, which individually or collectively contributed to increased yield and more accurate and more sensitive analyte detection methods.

The improved assays may be miniaturized, for example to the scale of a hand-held device such as a point of care device or at OTC product, in some instances due to the improved visualization of the polymer (e.g., nucleic acid) complexes that are readout of such methods.

The improved assays may also be used to achieve high throughput detection, given the low cost of the assay (e.g., on the order of cents per sample). The assays also do not require specialized equipment, making them more amenable to high throughput applications. It is contemplated that hundreds or thousands of samples may be tested in a day, all at relatively low cost. The samples to be run may include biological samples (e.g., where the presence of a particular analyte may indicate a particular condition such as pregnancy or infectious disease or cancer), environmental samples (e.g., where the presence of a particular analyte may indicate the presence of pathogens, chemicals, and the like), food samples (e.g., where the presence of a particular analyte may indicate contamination by pathogens, presence of pesticides, presence of allergens, and the like).

In addition to analyte detection methods, the nano switch technology and improvements thereof provided herein can be used, inter alia, in single molecule force spectroscopy measurements and in kinetic and equilibrium binding measurements using gel-electrophoresis.

Basic Nanoswitch Approach

FIG. 1 illustrates one exemplary nanoswitch synthesis and method of use. As illustrated, in one embodiment, DNA nanoswitches may be made by hybridizing one or more oligonucleotides to a longer scaffold nucleic acid, wherein at least one such oligonucleotide is conjugated to a binding partner of an analyte of interest. The illustration shows a plurality of oligonucleotides hybridized to the scaffold, but the method may be performed with a single oligonucleotide or with no oligonucleotide and simply conjugation of the binding partner to the scaffold itself. The use of hybridizing oligonucleotides facilitates specific positioning of the binding partner along the length of the scaffold and also renders the nanoswitch technology more versatile and universal since a plurality of oligonucleotides may be created that differ with respect to the binding partner conjugated to them. Various ways of generating a nanoswitch such as that illustrated in the Figure are available and should be apparent to one of ordinary skill in the art, apart from hybridization of a plurality of oligonucleotides. These include single-strand nicking of a double stranded nucleic acid, followed by hybridization to the nicked nucleic acid with one or more oligonucleotides conjugated to a binding partner of interest. The nicking action may be sequence-independent or sequence-dependent. The binding partners may be but are not limited to antibodies and antigen binding antibody fragments. The scaffold nucleic acid may be scaffold DNA such as linearized M13 DNA. In the presence of analyte, the two binding partners of the nanoswitch bind to a single analyte and thereby cause the nanoswitch to form a loop. Thus, such loop formation requires the action of at least two binding partners. The disclosure contemplates nanoswitches comprising two or more binding partners, with each binding interaction involving two or more binding partners rendering a different conformation that can be distinguished from other conformations using gel electrophoresis. In still other embodiments, not illustrated, the method may involve two physically separate polymers such as two physically separate nucleic acids, each conjugated to a binding partner, and in the presence of the analyte the two binding partners bind to the analyte, thereby causing the physical interaction of the two polymers. The result is a complex comprising the two polymers joined together via a common analyte and at two binding partners to such analyte. The resulting mixture is run on a gel such as an agarose gel and imaged, with signal given by the intensity of the slower migrating band that corresponds to nanoswitches having a looped conformation with analyte bound, in some embodiments. In other embodiments, the band of interest may correspond to a complex of two polymers indirectly conjugated to each other as described above.

Typically, the concentration of nanoswitch is greater than the dissociation constant of the more strongly binding antibody, so that almost all the analyte is bound to a nanoswitch after incubation. The technique enables detection of concentrations as low as 100fM.

Improved Nanoswitch Approach for Complex Matrices

This disclosure provides an improvement on the foregoing method for use with complex samples. A complex sample, as used herein, is a sample comprising components other than the analyte of interest. Such components may be proteins or small molecules that may interfere with the binding of the analyte to its binding partners or that may interfere with other steps in the process such as loading of the mixture into a gel and/or migration of the nanoswitches or complexes through the gel in a manner that allows different conformations or complexes to be differentiated from each other. In some embodiments, a complex sample may comprise a mixture of different proteins. In some embodiments, a complex sample may comprise a high amount or concentration of one or a small number of proteins. An example of a complex sample is a serum sample. Another example is a filtered blood sample. Yet another example is a urine sample.

Illustrated in FIG. 1 is one embodiment in which the nanoswitches comprise two analyte-binding antibodies at specific locations along a linear DNA scaffold. When the DNA nanoswitches are mixed with a sample containing the analyte (or target molecule, as the terms are used interchangeably herein), the antibodies sandwich the analyte to form looped structures. After mixing with loading buffer, these looped nanoswitches are physically separated from unbound, linear nanoswitches using gel electrophoresis. In one embodiment of the improved method, the gel is pre-stained with SYBR Gold or other nucleic acid (e.g., DNA) binding dye (or DNA binding stain, as the terms are used interchangeably herein). The dye is useful for visualizing the complex during or after gel electrophoresis. The dye may be pre-loaded into the gel or alternatively the nanoswitches may be incubated with the dye prior to loading into the gel.

In some embodiments, a large amount of sample may be loaded into the gel (e.g., using a thick 3 mm comb to create the loading wells). This serves to increase band intensity for better detection of analytes that are present in the sample at low concentrations. Rectangular shaped combs, trapezoidal shaped combs with the shorter side facing the anode, as well as other comb shapes may be used in order to reduce noise by preventing smearing along the edges of the gel lane. The intensity of the band corresponding to looped nanoswitches measures the amount of analyte in the sample. The procedure can be performed with no washing or amplification steps.

In some embodiments, one or more nuclease inhibitors may be added to the sample, or the nanoswitches, or the sample/nanoswitch mixture. An example of such an inhibitor is EDTA which chelates cations, such as magnesium ions, that are co-factors for nucleases. In the presence of EDTA or other inhibitors, nucleases such as DNases will not degrade the nanoswitches.

In some embodiments, a protein binding dye may also added to the sample, or the nanoswitches, or the sample/nanoswitch mixture (e.g., it may be added to the loading dye ahead of the gel electrophoresis). The protein binding dye preferably is a dye that binds to proteins indiscriminately (i.e., it binds non-specifically to proteins). The dye may be negatively charged, including negatively charged at the conditions in which the assays is performed including under which the gel is run. Such conditions may include a pH of about 7. An example of such a protein binding dye is Coomassie Blue. In some embodiments, the protein binding dye is positively charged under the assay conditions.

It has been found in accordance with this disclosure that the combined use of a protein binding dye with a nuclease inhibitor and/or a nucleic acid binding dye leads to a significantly improved assay. Such assay may be better able to detect analytes that are present at low concentration, or may be used to reproducibly and robustly assay a complex sample without waste or need for duplication that might be otherwise required due to the large non-analyte protein matrix present in the sample.

As described in the Examples, in an exemplary demonstration of the improved method, human PSA spiked into a 1:4 dilution of fetal bovine serum was measured. In order to protect the DNA nanoswitches and PSA from degradation during incubation, EDTA was added to a concentration of 100 mM. Both SYBR Gold and Coomassie Blue G-250 were included in the loading buffer, to allow the nanoswitches to enter the gel and increase the signal-to-noise, as shown in FIGS. 2A and 2B. A similar analysis has been performed to assay thyroid-stimulating hormone (TSH) in serum (data not shown).

Coomassie Blue G-250 is negatively charged at a pH of about 7 and it binds to proteins indiscriminately. Coomassie Blue is able to bind to proteins in the serum sample, giving them a negative charge, causing them to migrate out of the well, and thereby allowing the nanoswitches to enter the gel. It has been found that in some instances in the absence of such protein binding dyes the proteins remain in or near the loading wells and can interfere with nanoswitch entry or migration through the gel.

Including SYBR Gold in the loading buffer stains the nucleic acid of the nanoswitch more strongly than if SYBR Gold was only present in the agarose (e.g., in a preloaded gel). Additionally, SYBR Gold in the loading buffer also helps polymers (e.g., nucleic acids and/or proteins) enter the gel, presumably because the positively charge SYBR Gold molecules also bind to such polymers and cause them to move out of the well.

The methods provided herein may be performed using any charged molecule that binds to proteins indiscriminately in the complex matrix being assayed, as such charged molecules cause protein to enter the gel during electrophoresis. While the method has been exemplified using dyes in serum, it is to be understood that it may be used on other complex matrices with high protein content, such as but not limited to blood in which cells have been removed using filtration or centrifugation, blood in which cells have been lysed either chemically or physically, cell lysate, and culture media or supernatant.

Detection of Individual Analytes or Multicomponent Complexes

The methods provided herein can be used to detect analytes with low noise, thereby allowing for sensitive detection of low abundance analytes. Various descriptions provided herein may refer solely to analytes but it is to be understood that this is for the sake of brevity and that multicomponent complexes are also intended in such descriptions unless stated otherwise. Various descriptions provided herein may refer solely to nanoswitches but it is to be understood that this is for the sake of brevity and that other polymer based techniques, such as those described herein involving polymers indirectly complexed to each other via a common analyte (or multicomponent complex) are also intended in such descriptions unless stated otherwise.

Thus, some methods detect and optionally quantitate a multicomponent complex. A multicomponent complex is a complex of two or more components. The components may be covalently linked to each other, or they may be non-covalently linked to each other. Examples of such complexes include transcriptional or translational complexes, cell cycle complexes, inflammasomes, and other "-some" like complexes. In these methods, the binding partners may recognize and bind to different components of the complex yet together they still bind to the sample complex. These methods rely on the association between the components of the complex to be sufficiently stable to withstand the binding reaction and the readout process (e.g., gel electrophoresis). If they are not, then a latch mechanism may be used to stabilize the interaction between the two polymers of a polymer pair or between the two binding partners on a single polymer.

Nanoswitches

The nanoswitches of this disclosure minimally comprise a scaffold or backbone nucleic acid comprising one or more, and typically two or more binding partners. The scaffold nucleic acid may be of any length sufficient to allow association (i.e., binding) and dissociation (i.e., unbinding) of binding partners to occur, to be detected, and to be distinguished from other events. In some instances, the scaffold nucleic acid is at least 1000 nucleotides in length, and it may be as long as 20,000 nucleotides in length (or it may be longer). The scaffold nucleic acid may therefore be 1000-20,000 nucleotides in length, 2000-15,000 nucleotides in length, 5000-12,000 in length, or any range therebetween. The scaffold may be a naturally occurring nucleic acid (e.g., M13 scaffolds such as M13mp18). M13 scaffolds are disclosed by Rothemund 2006 Nature 440:297-302, the teachings of which are incorporated by reference herein. The scaffold nucleic acid may be lambda DNA, in other embodiments. The scaffold nucleic acid may also be non-naturally occurring nucleic acids such as polymerase chain reaction (PCR)-generated nucleic acids, rolling circle amplification (RCA)-generated nucleic acids, etc.

In some embodiments, the binding partners are positioned along the scaffold nucleic acid to yield loops and thus length changes that are detectable. These may include loops that are about 40-100 base pairs, or about 100-1000 base pairs, or about 500-5000 base pairs. The scaffold may be partially or fully single-stranded or partially or fully double-stranded. The complex may comprise varying lengths of double-stranded regions.

The scaffold nucleic acid may comprise DNA, RNA, DNA analogs, RNA analogs, or a combination thereof. In some instances, the binding partners are conjugated to a scaffold nucleic acid via hybridization of oligonucleotides to the scaffold, wherein such oligonucleotides are themselves conjugated to a binding partner. In some instances, the scaffold nucleic acid is a DNA.

In some instances, then the scaffold nucleic acid may be hybridized to one, two or more, including a plurality, of oligonucleotides. Each of the plurality of oligonucleotides may hybridize to the scaffold nucleic acid in a sequence-specific and non-overlapping manner (i.e., each oligonucleotide hybridizes to a distinct sequence in the scaffold).

The number of oligonucleotides hybridized to a particular scaffold may vary depending on the application. Accordingly, there may be 2 or more oligonucleotides hybridized to the scaffold, including 3, 4, 5, 6, 7, 8, 9, 10, 20, 30, 40, 50, 60, 70, 80, 90, 100, 200, 300, 400, 500, 600, 700, 800, 900, or 1000 or more oligonucleotides.

In some instances, some oligonucleotides hybridized to the scaffold nucleic acid will be unmodified. Unmodified oligonucleotides include oligonucleotides that are not linked to binding partners such as binding partners being tested (e.g., an antibody or an antigen). In other instances, some or all the oligonucleotides hybridized to the scaffold may be modified. Modified oligonucleotides include those that are linked to binding partners being tested (e.g., a receptor and/or its ligand, an antibody and/or its antigen, etc.). Modified oligonucleotides may also include those that are modified and thus used to immobilize the nanoswitch to a solid support such as but not limited to a bead. Such modified oligonucleotides including biotinylated oligonucleotides. Modified oligonucleotides may be referred to herein as "variable" oligonucleotides since these oligonucleotides may be modified by linking to a variety of binding partners depending on the method of use.

Regions comprising scaffold hybridized to modified oligonucleotides may be referred to herein as "variable" regions and the remaining scaffold regions may be referred to as "fixed" regions.

The scaffold-binding partner construct may be made in a number of ways including through nicking of a double stranded nucleic acid to which binding partners are conjugated (to one strand), or by hybridization of one or more oligonucleotides to the scaffold, as described herein in greater detail.

In other instances, the binding partners may be conjugated to the scaffold nucleic acid itself rather than to an oligonucleotide that is hybridized to the scaffold.

The spacing of binding partners, and thus in some instances of the modified (or variable) oligonucleotides, along the length of the scaffold nucleic acid may vary. In some embodiments, the nanoswitch may comprise two, three or four binding partners, and thus in some embodiments variable regions (e.g., two or three or four modified oligonucleotides). As an example, a nucleic acid nanoswitch may comprise two internal modified oligonucleotides. The modified oligonucleotides internal to the nanoswitch may be linked individually to members of a binding pair (i.e., each of the two oligonucleotides is linked to a member of the binding pair such that the nanoswitch comprises the binding pair, with each member of the pair on a different oligonucleotide). The internal modified oligonucleotides may be symmetrically or quasi-symmetrically located around the center of the scaffold. In other words, they may be positioned equi-distant from the center of the scaffold.

The distance between the binding pair members may be 300 base pairs, 200 base pairs, 150 base pairs, 100 base pairs, 80 base pairs, 60 base pairs, and 40 base pairs.

Importantly, the distance between the binding partners will be used to distinguish association and dissociation between binding partners linked to the nanoswitches. This is because when the binding partners are associated with each other, a loop will be formed comprising the nucleic acid sequence that exists between the binding partners. When the binding partners are not associated to each other (i.e., unbound), then the loop does not form and the complex length is different (i.e., longer). The nanoswitch configuration can be determined by analyzing the migration of the nanoswitch through a matrix such as a gel in a gel electrophoretic system. The unbound, linear form travels more rapidly than does the bound, looped form. Thus, presence of an analyte of interest, to which the binding partners on a single nanoswitch bind, will trigger the formation of a bound and looped nanoswitch. The bound, looped nanoswitch will be distinguished from its unbound, linear counterpart based on the difference in their migration distances through a gel or other pore-containing matrix.

It is to be understood that several variations on the nucleic acid nanoswitches described herein. Typically, these variations all commonly comprise a nucleic acid nanoswitches having two or more binding partners. The binding partners typically have binding specificity for a common analyte. Several of the methods rely on the association and/or dissociation of binding partners. A change in conformation of the nanoswitch (e.g., from an open to a closed conformation) provides information about the presence of the analyte. The binding partners may be non-covalently or covalently bound to the scaffold.

In another variation, the nucleic acid complex comprises two binding partners having binding specificity for a common analyte. The binding partners are physically separate and thus spaced apart from each other (when not bound to the common analyte). When bound to the common analyte, the nucleic acid nanoswitch assumes a looped (or closed or bound) conformation having a different formation and thus a different "apparent" length (as for example measured using migration through a gel electrophoresis system), compared to the nucleic acid nanoswitch in an open (or unbound) conformation.

The invention further contemplates that a nucleic nanoswitches may comprise more than two conjugated binding partners. The number of binding partners may be 2, 4, or more. In some embodiments, pairs of binding partners are provided, with each pair having binding specificity for a particular analyte. A single nanoswitch may comprise a binding pair for a first analyte, which may be a test analyte, and a second binding pair for a second analyte, which may be a control analyte. In this way, the nanoswitch may have a control reading as well as a test reading. For example, if the nanoswitch is used to measure a marker of ovulation or pregnancy, then a first binding pair may bind to such marker and a second binding pair may bind to a control protein or other moiety that will always be present in the sample being tested (e.g., the urine) in order to establish to the end user that a sufficient quantity of sample was applied to the system. The location or arrangement of the binding partners may vary and may include serially positioned binding pairs or nested binding pairs, or combinations thereof. As an example, assume that A1 and A2 are a binding pair (e.g., first and second binding partners) and B1 and B2 are a different binding pair (e.g., third and fourth binding partners), then these may be arranged as 5'-A1-A2-B1-B2-3', or they may be arranged as 5'-A1-B1-B2-A2-3'. In other embodiments, assuming that a single nanoswitch is able to bind to a number of different analytes, but can only bind to one analyte at a time, the nanoswitch may be arranged as follows: 5' A1-A1a-A1b-A1c-A1d-A1e 3'. In this nanoswitch, all the analytes being detected may commonly bind to the A1 location, but each may then also bind to only one unique location chosen from A1a through to A1e. Alternatively, the test and control analytes may be assayed using different nanoswitches that are nevertheless still run through the same gel system.

The nanoswitches comprise binding partners such as for example an antibody or an antigen. The linkage between the nucleic acid and the binding partner may be covalent or non-covalent depending on the strength of binding required for a particular application. They may be generated by first incorporating a reactive group (or moiety) into the nucleic acid (or into an oligonucleotide hybridized to the nucleic acid), and then reacting this group (or moiety) with the binding partner of interest which may or may not be modified itself. Suitable reactive groups are known in the art. Examples of reactive groups that can covalently conjugate to other reactive groups (leading to an irreversible conjugation) include but are not limited to amine groups (which react to, for example, esters to produce amides), carboxylic acids, amides, carbonyls (such as aldehydes, ketones, acyl chlorides, carboxylic acids, esters and amides) and alcohols. Those of ordinary skill in the art will be familiar with other "covalent" reactive groups. Examples of reactive groups that non-covalently conjugate to other molecules (leading to a reversible conjugation) include biotin and avidin or streptavidin reactive groups (which react with each other), antibody (or antibody fragment) reactive groups and antigens, receptors and receptor ligands, aptamers and aptamer ligands, nucleic acids and their complements, and the like. Virtually any reactive group is amenable to the methods of the invention, provided it participates in an interaction of sufficient affinity to prevent dissociation of the binding partner from the nucleic acid nanoswitch.

It is to be understood that the scaffold nucleic acid and if used the oligonucleotides may be DNA or RNA in nature, or some combination thereof, or some analog or derivative thereof. The term nucleic acid refers to a polymeric form of nucleotides of any length, including deoxyribonucleotides, ribonucleotides, or analogs thereof. In some embodiments, the nucleic acids will be DNA in nature, and may optionally comprise modifications at their 5' end and/or their 3' end.

In some embodiments, the binding partners may include without limitation antibodies (or antibody fragments) and antigens, receptors and ligands, aptamers and aptamer receptors, nucleic acids and their complements, and the like. This list is not intended to be limited or exhaustive and other binding partners will be apparent and may be used in conjunction with the nanoswitches described herein.

Reference may also be made to published PCT application WO 2013/067489 and PCT application PCT/US15/60952.

Other Polymer Complexes

As discussed above, the methods provided herein may be performed using polymers, including polymer pairs, that are conjugated to binding partners of known or unknown specificity. The polymer pairs are designed so that both polymers in the pair bind to the same analyte, thereby converting from two separate, optionally linear polymers, into a complex in which the two polymers are effectively joined through the analyte. This newly formed complex is distinguishable from the linear forms of the polymers, and can be detected readily using any one of a variety of standard techniques including but not limited to gel electrophoresis. Additionally, combinations of polymer pairs may be used together, each specific for a different analyte, and each able to form upon binding analyte a complex that is distinguishable from complexes formed by other polymer pairs. Thus, the methods are amenable to multiplexed analysis, allowing detection and quantitation of a two or more analytes simultaneously.

Some of these approaches employ polymer pairs that are able to bind to an analyte, such as a single molecule or compound, or a multicomponent complex, thereby undergoing a conformational change from single, optionally linear, polymers to a polymer-analyte complex typically having an X-shaped structure, with four free ends, and an analyte bridge. The difference in structure between the bound and unbound (e.g., essentially linear) states allows for separation between bound and unbound states.

In a first approach a polymer pair (i.e., two polymers) is used. Each polymer of the pair is conjugated to an analyte-binding partner such as but not limited to an antibody. These analyte-specific binding partners may bind to the same analyte or to different components of the same multicomponent complex. (The same applies for the nanoswitches described herein.) If binding to the same analyte, the analyte-specific binding partners may or may not be identical (i.e., they may bind to the same epitope, provided the analyte has at least two copies of the epitope, or they may bind to different epitopes on the same analyte). Importantly, the binding partners must be capable of binding to the same analyte (or multicomponent complex) simultaneously in order to form the bridge between the two polymers of the polymer pair. The binding partners may be located anywhere along the length of the polymers, with the most pronounced separation from unbound polymers more likely to occur if they are located at about the mid-point of the polymer. Polymers having binding partners located at their ends or at other internal locations, once complexed, can also be distinguished from linear unbound polymers and perhaps more significantly can be distinguished from other complexes, thereby facilitating multiplexed assays.

The second approach uses a single polymer having conjugated thereto two analyte-specific binding partners. As in the first approach, these binding partners may bind to the same analyte or to different components of the same multicomponent complex. If binding to the same analyte, the analyte-specific binding partners may or may not be identical (i.e., they may bind to the same epitope, provided the analyte has at least two copies of the epitope, or they may bind to different epitopes on the same analyte). Importantly, the binding partners must be capable of binding to the same analyte (or multicomponent complex) simultaneously in order to form a loop structure from the polymer. The binding partners may be located anywhere along the length of the polymer, although the most pronounced separation from unbound polymers is more likely to occur if they are located at about one quarter and three quarters the length of the polymer, as illustrated. Binding of the two binding partners to the same analyte or multicomponent complex forms a looped structure, and this looped structure is cleaved by any known means to form an X-shaped structure similar to that of the first approach. Cleavage may be achieved chemically or enzymatically, although other means are not excluded. Cleavage can occur directly on the polymer (such as a restriction enzyme cutting a specific nucleotide sequence), or via a distinct entity connecting two polymer portions (such as using TCEP to cleave a disulfide bond connecting two nucleic acids).

This disclosure provides variations of these two approaches, including detection of more than one analyte using a single polymer pair, detection of more than one analyte using more than one polymer pair (with each pair specific for one analyte), identification of one or more analytes simultaneously with or following detection, and the like. This disclosure also contemplates additional mechanisms for bridging polymers in order to enhance or stabilize their binding, particularly when the binding affinity of the binding partner for the analyte is low or the target is a multicomponent complex which is easily disrupted. These and other variations are considered part of this disclosure and will be discussed in greater detail herein.

Polymers

The polymers may be naturally occurring polymers or non-naturally occurring polymers. They may be or may comprise nucleic acids, peptides, proteins, polysaccharides, lipids, and the like. They may be or may comprise block polymers or block-co-polymers.

The polymers may be nucleic acids in whole or in part. They may comprise naturally occurring nucleotides and/or non-naturally occurring nucleotides. They may be or may comprise DNA, RNA, DNA analogs, RNA analogs, PNA, LNA and combinations thereof, provided it is able to hybridize in a sequence-specific manner to oligonucleotides and/or to be conjugated to a binding partner.

In some instances, the polymers are single-stranded nucleic acids. Such nucleic acids may be modified to include one or more binding partners at particular positions.

The polymers may be single stranded nucleic acids hybridized to one or more modified oligonucleotides that are conjugated to one or more binding partners. Such nucleic acids may be referred to herein as scaffold nucleic acids. They may also be referred to as "single-stranded" and it is to be understood that this refers to their state prior to hybridization to the one or more oligonucleotides. The scaffold nucleic acid may be hybridized to one or more including two, three, four, or more oligonucleotides. Each oligonucleotide may comprise one or more binding partners, depending on their length. As an example, if a nucleic acid is conjugated to two binding partners, the nucleic acid may be hybridized to one oligonucleotide comprising the two binding partners or it may be hybridized to two oligonucleotides, each of which comprises a binding partner. The oligonucleotides are typically designed to hybridize to particular regions on the scaffold, such as at about the mid-point of the scaffold. The scaffold nucleic acid may or may not be hybridized to additional, unmodified oligonucleotides.

Accordingly, the polymer may be a single-stranded nucleic acid, a partially double-stranded nucleic acid, or a completely double-stranded nucleic acid. The polymer may be a double-stranded nucleic acid. For example, it may be at least 10%, at least 20%, at least 30%, at least 40%, at least 50%, at least 60%, at least 70%, at least 80%, at least 90%, at least 95%, at least 96%, at least 97%, at least 98%, at least 99%, or 100% double-stranded. The nucleic acids may therefore comprise double-stranded and single-stranded regions. Double-stranded regions may comprise "single-stranded nicks" as the hybridized oligonucleotides may not be ligated to each other.

When the polymer is a nucleic acid, it may be of any length sufficient to visualize the nucleic acid and the resultant complex it forms in the presence of analyte, and in some instances to form a loop upon binding to analyte. In some instances, the nucleic acid is at least 1000 nucleotides in length, and it may be as long as 20,000 nucleotides in length, or it may be longer. The nucleic acid may be 1000-20,000 nucleotides in length, 2000-15,000 nucleotides in length, 5000-12,000 in length, or any range therebetween. The nucleic acid may be a naturally occurring nucleic acid (e.g., M13 DNA such as M13mp18 having a length of about 7250 nucleotides). Use of M13 DNA as a scaffold nucleic acid is disclosed by Rothemund 2006 Nature 440:297-302, the teachings of which are incorporated by reference herein. The disclosure contemplates use of full length M13 DNA or use of a fragment of M13 DNA provided it is of sufficient length.

Nucleic acids to be used as polymers may be naturally occurring and thus harvested from a naturally occurring source. Alternatively, they may be non-naturally occurring nucleic acids such as polymerase chain reaction (PCR)-generated nucleic acids, rolling circle amplification (RCA)-generated nucleic acids, etc. If the polymer is a single stranded nucleic acid, it may be generated using for example asymmetric PCR. Alternatively, double-stranded nucleic acids may be subjected to strand separation techniques in order to obtain the single-stranded nucleic acids.

It is to be understood that the nucleic acid may also comprise a plurality of nicks that are typically located between bound oligonucleotides. The length and the number of oligonucleotides used may vary. In some instances, the length and sequence of the oligonucleotides is chosen so that each oligonucleotide is bound to the scaffold nucleic acid at a similar strength. This is important if a single condition is used to hybridize a plurality of oligonucleotides to the nucleic acid. In some instances, the oligonucleotides are designed to be of approximately equal length. The oligonucleotides may be about 10, about 15, about 20, about 30, about 40, about 50, about 60, about 70, about 80, about 90 or about 100 nucleotides in length. The number of oligonucleotides in the plurality may be about 50, about 60, about 70, about 80, about 90, about 100, about 110, about 120, about 130, about 140, about 150, about 160, about 170, about 180, about 190, or about 200, without limitation.

The number of oligonucleotides hybridized to a particular scaffold may vary depending on the application. Accordingly, there may be 2 or more oligonucleotides hybridized to the scaffold, including 3, 4, 5, 6, 7, 8, 9, 10, 20, 30, 40, 50, 60, 70, 80, 90, 100, 200, 300, 400, 500, 600, 700, 800, 900, or 1000 or more oligonucleotides. It will be understood that the number of oligonucleotides will depend in part on the application, the length of the scaffold, and the length of the oligonucleotides themselves.

Selection of Secondary Structure (SS) Free Scaffold Regions and Complementary Oligonucleotides As described herein, in some instances, a nucleic acid nanoswitch may minimally comprise a scaffold nucleic acid conjugated to one or two or more molecules, such as but not limited to analyte-specific binding partners or bridging oligonucleotides, thereby rendering a "functionalized" scaffold. The molecules of interest may be directly or indirectly conjugated to the scaffold. If indirectly conjugated, typically the molecules of interest are conjugated to an oligonucleotide that is complementary to a region (sometimes preferably a single region) of the scaffold. Such regions may be referred to herein as "target" regions (or sequences). To functionalize a nucleic acid (e.g., DNA) nanoswitch, the target regions are left single stranded. An oligonucleotide that is complementary to the target region is conjugated to the molecule of interest, and the oligonucleotide is then capable of hybridization to its complementary target region in the scaffold.

In some instances, the complementary oligonucleotides and their target regions may have internal secondary structure, which limits their hybridization efficiency. In order to increase the hybridization efficiency, nucleic acid nanoswitch hybridization may be performed at an elevated temperature. A drawback to this methodology is that such elevated temperature may be incompatible with the stability and activity of some analyte-specific binding partners and/or some analytes. To further address the issue, in certain embodiments, a temperature ramp protocol may be used (typically from 90 to 20° C. at 1° C. min$^{-1}$) that reduces the internal secondary structure to increase the hybridization efficiency. However, even a temperature ramp may not yield maximal results, in some instances, because the analyte-specific binding partners and/or the analyte may still degrade and/or lose function due to thermal damage or denaturation.

Thus, the full impact of such internal secondary structure on hybridization efficiency and the various methodologies for overcoming it have not been fully appreciated heretofore. Provided herein are further improvements to this methodology. For example, hybridization of the functionalized oligonucleotide can be improved if it is selected to have a secondary structure free sequence, as illustrated in FIG. 3. A sequence that has no internal base-pairing in its most thermodynamically favorable structure (i.e., the structure having the lowest free energy) at the desired temperature, such as room temperature, may be selected. Without secondary structure in the target region and in the complementary oligonucleotide, the scaffold and the oligonucleotide can be efficiently hybridized without the need to increase the temperature to melt the internal base-pairing, including for example without the need for a temperature ramp.

Figure 4A:
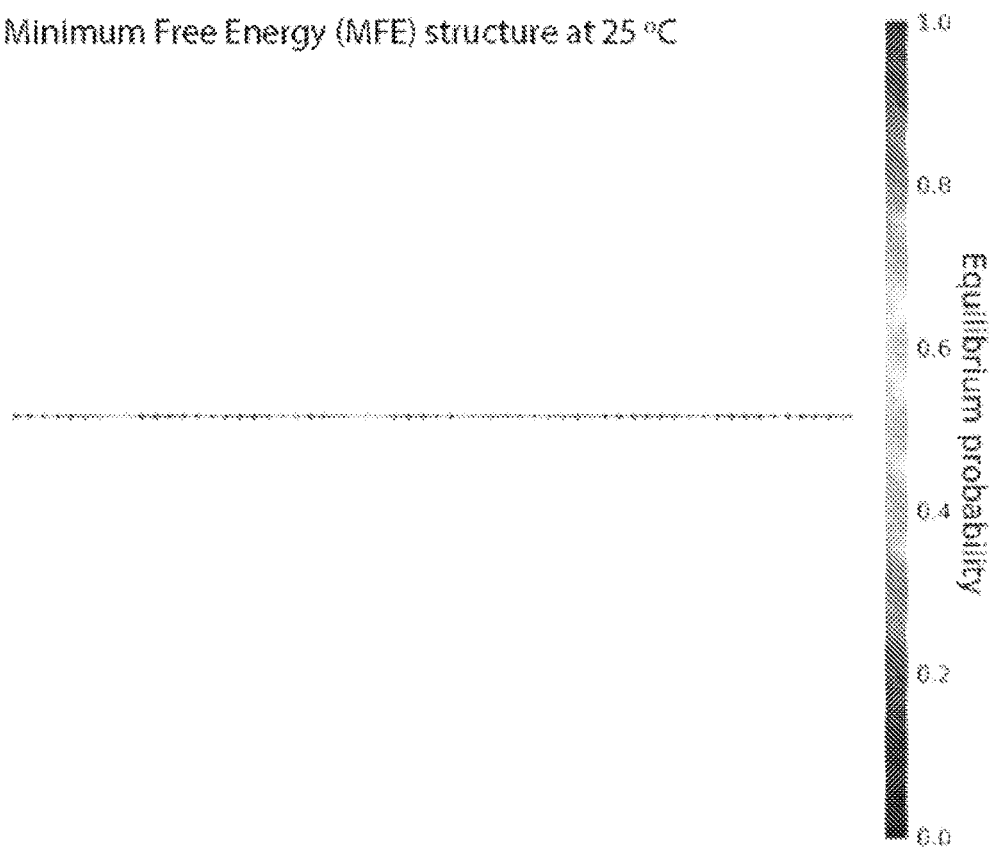
FIGS. 4A to 4C. Example of the secondary structure free nanoswitch.
Figure 4B:
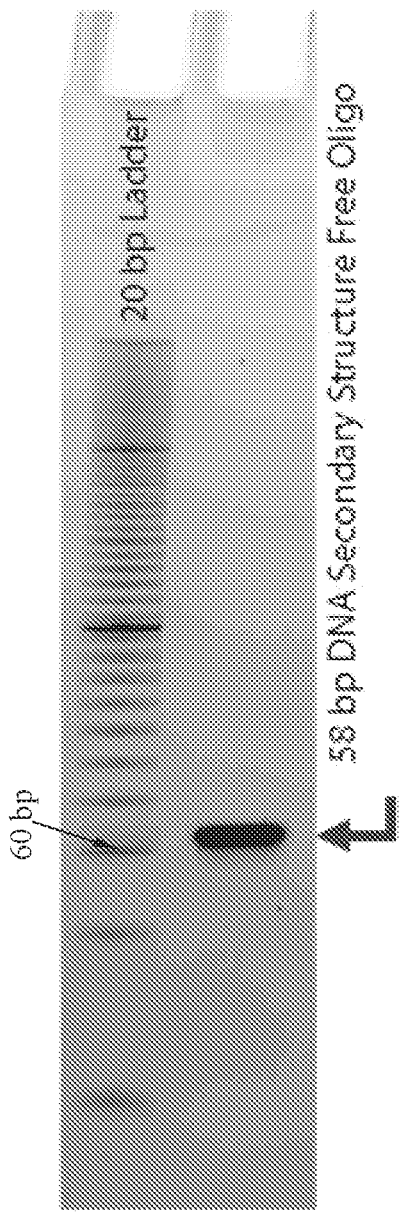

Suitable target regions in the context of a larger scaffold may be selected using, for example, computational sequence analysis, such as but not limited to an algorithm such as NuPack (Zadeh et al. 2011) (or other algorithms). These algorithms may be used to identify the regions on a scaffold of known sequence, such as the M13 scaffold, that are secondary structure free at a desired temperature or temperature range (FIG. 4A). Gel electrophoresis analysis can be carried out on the oligonucleotide to further verify the absence of internal base-pairing (leading to secondary structure), as shown in FIG. 4B. This analysis reveals that the 58 bp oligonucleotide adopts a single linear form, as evidenced by a single band of the appropriate length. In comparison, FIG. 4C demonstrates that an oligonucleotide, 29 bp in length, adopts a linear, secondary structure free form and a form having secondary structure. The higher MW band, indicative of the latter form, may adopt the conformation shown in the inset at the top.

Figure 5:
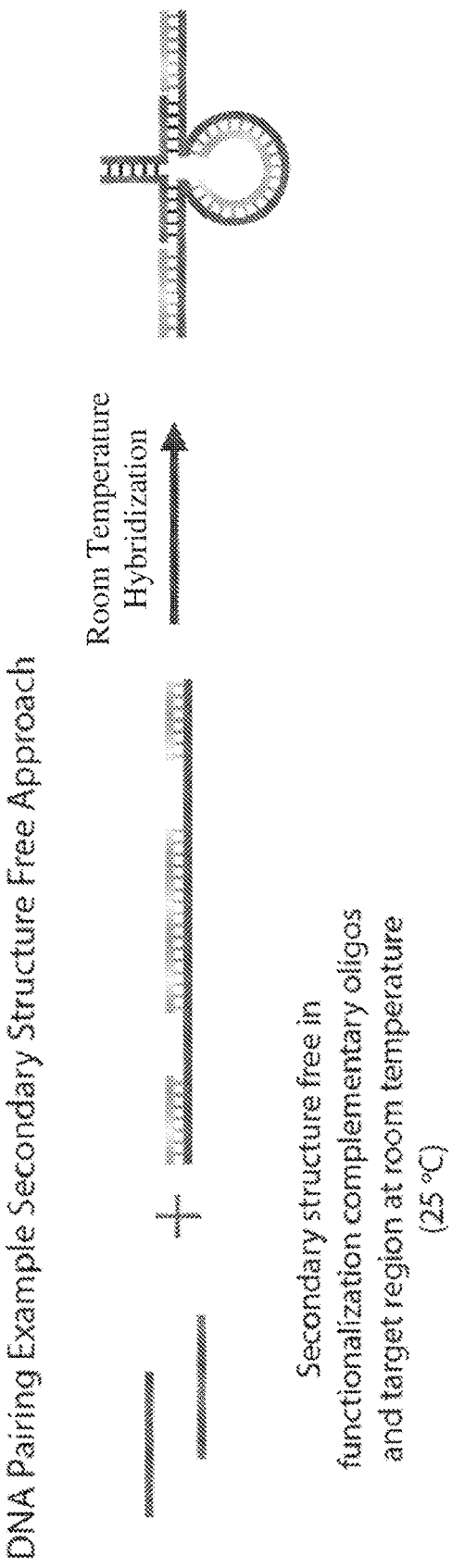
FIG. 5. Schematic of DNA pairing using the secondary structure free approach. Shown is an example of a secondary structure free target region selection approach. The DNA nanoswitch loop is formed by hybridization of the oligonucleotides. The entire process may be performed at room temperature since the nanoswitch is linear at that temperature.
Figure 6:
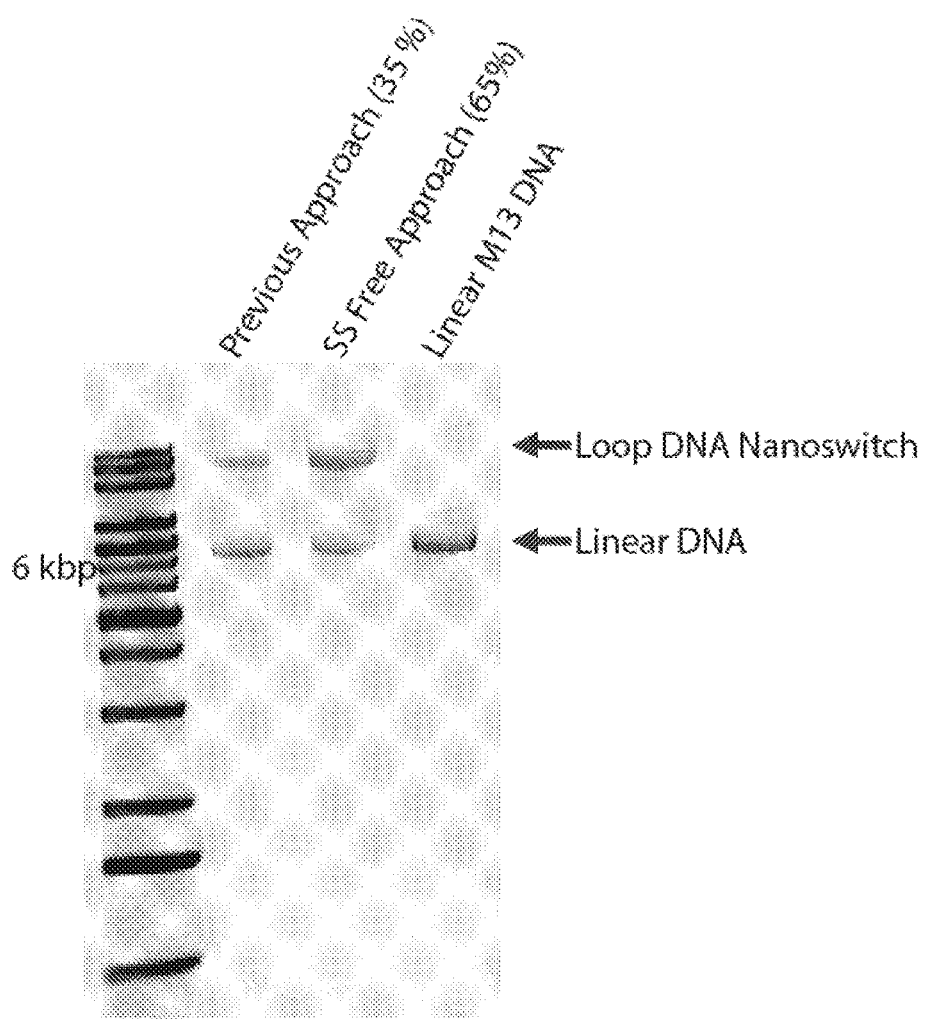
FIG. 6. Gel electrophoresis of the DNA nanoswitch, showing loop formation in the presence of the bridging oligonucleotide The previous approach refers to a method in which loop formation occurs under high temperature in order to melt existing secondary structure present in the nanoswitch (e.g., in the scaffold nucleic acid of the nanoswitch). The Figure shows improved formation of the loop form using the secondary structure (SS) free form as compared to the previous approach (e.g., the ratios of looped to unlooped (or linear) for previous and improved approach appear inversed).

A schematic use of a SS-free oligonucleotide and scaffold is provided in FIG. 5. In this example, the nanoswitch is designed to bind to two different oligonucleotides (shown on the left), which are partially complementary to each other, thereby resulting in a loop form (shown on the right). As with other nanoswitch systems, the hybridization efficiency may be quantified by the fraction of looped yield, as provided in FIG. 6. There it is shown that hybridization efficiency is increased when oligonucleotides and target regions are selected or designed to have no (or little likelihood of) secondary structure at a desired temperature.

An analysis of M13 for sequences having little or no secondary structure at room temperature (e.g., about 20-25° C.) was conducted using the NuPack algorithm. This analysis yielded a number of regions having little or no secondary structure. The sequences of some of these regions are as follows:

```
                                              (SEQ ID NO: 1)
CTGAGTAATGTGTAGGTAAAGATTCAAAAGGGTGAGAAAGGCCGGAGACA
GTCAAATCAC (SEQ ID NO: 2)
CATCACCTTGCTGAACCTCAAATATCAAACCCTCAATCAATATCTGGTCA (SEQ ID NO: 3)
CAATATATGTGAGTGAATAACCTTGCTTCTGTAAATCGTCGCTATTAATT
AATTTTCCCT (SEQ ID NO: 4)
CTGAACAAGAAAATAATATCCCATCCTAATTTACGAGCATGTAGAAACC
AATCAATAAT (SEQ ID NO: 5)
TTGTTTAACGTCAAAAATGAAAATAGCAGCCTTTACAGAGAATAACAT
AAAAACAGGG (SEQ ID NO: 6)
GGTCATAGCCCCCTTATTAGCGTTTGCCATCTTTTCATAATCAAAATCAC
CGGAACCAGA (SEQ ID NO: 7)
GTTTAGTACCGCCACCCTCAGAACCGCCACCCTCAGAACCGCCACCCTCA
GAGCCACCAC (SEQ ID NO: 8)
AAGAACCGGATATTCATTACCCAAATCAACGTAACAAAGCTGCTCATTCA (SEQ ID NO: 9)
CCAGAACGAGTAGTAAATTGGGCTTGAGATGGTTTAATTTCAACTTTAAT
CATTGTGAAT
```

Nanoswitch System with Two-Point Attachment

Figure 10:
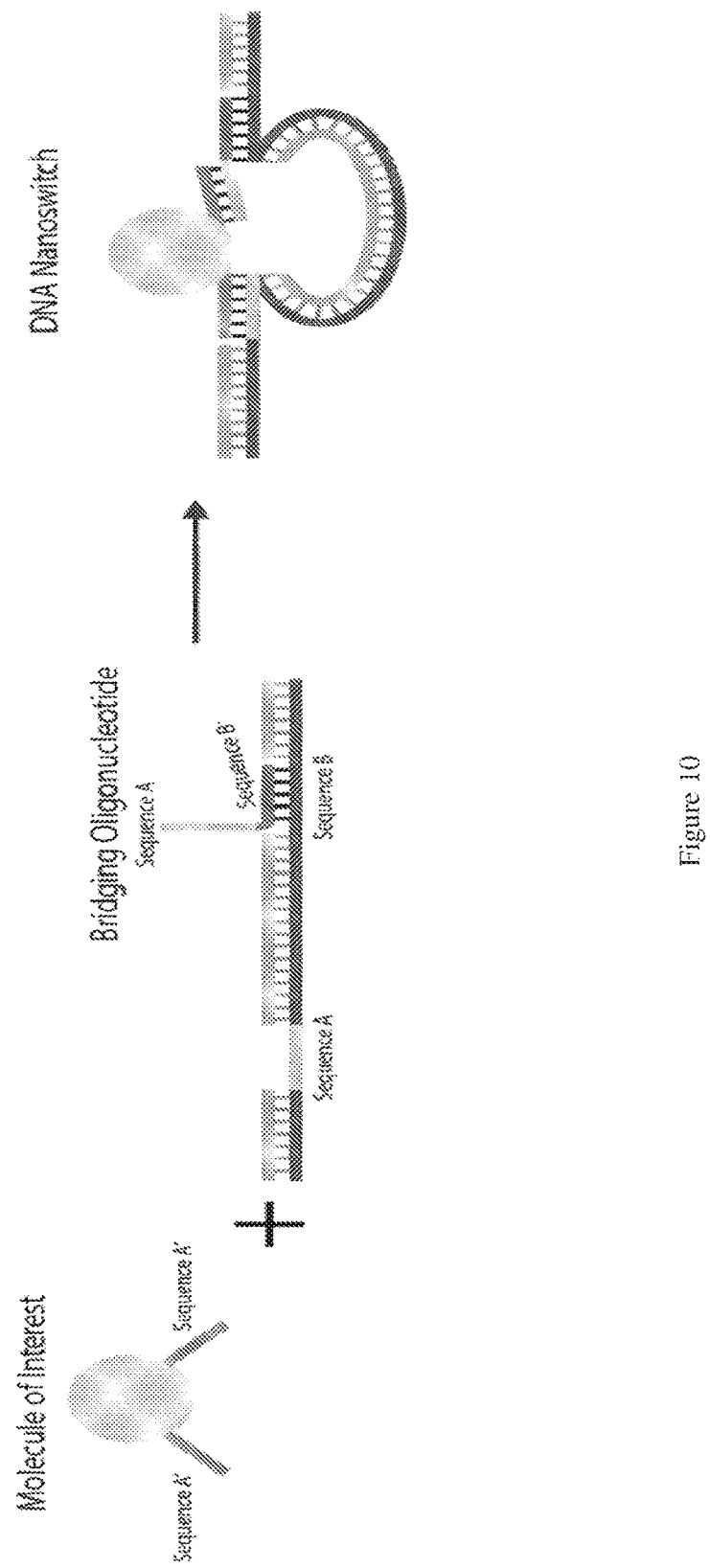
FIG. 10. Schematic of the oligonucleotide-bridging method used to construct a looped nanoswitch.

A variation of the nanoswitch system described herein was further developed. This approach is illustrated schematically in FIG. 10 and is referred to herein as a two-point attachment approach. This approach involves conjugating a molecule of interest to two oligonucleotides and hybridizing the oligonucleotides to their respective complementary sequences on the nanoswitch. In the illustrated embodiment, the oligonucleotides are identical in sequence (both sequence A'). The nanoswitch is designed to contain a target region that is complementary to the oligonucleotide (and thus has sequence A) as well as a bridging oligonucleotide that is (a) partially hybridized to the scaffold at the target region having sequence B and (b) partially single stranded and available for hybridization to the oligonucleotide having sequence A'. The molecule of interest can then bind to the nanoswitch via its two oligonucleotides, thereby forming a looped structure.

This design can be used to assess the stability and integrity of the molecule of interest under different conditions including in the presence of other molecules some of which may for example degrade or cleave (including enzyme cleavage of) the molecule of interest. Once the integrity of the molecule of interest is compromised, the looped structure may be relaxed and may begin to resemble the linear structure of the nanoswitch. In this way, there is a readout for conditions or agents that impact the structure of the molecule of interest.

This design can also be used for force spectroscopy analyses.

Sample and Analytes

The sample being tested for the presence of the one or more analytes may be a biological sample such as a bodily fluid (e.g., a blood sample, a urine sample, a sputum sample, a stool sample, a biopsy, and the like). The sample may be complex. As used herein, a complex sample refers to a sample comprising a plurality of known and unknown components. The plurality may be in the tens, hundreds or thousands.

The analyte to be detected may be virtually any analyte provided binding partners specific for the analyte are available and that it can be bound by at least two binding partners simultaneously. This typically means that it is large enough to be bound by two binding partners and that it has at least two epitopes that can be bound simultaneously, whether those epitopes are identical or different from each other. The analytes may be or may comprise nucleic acids, peptides or proteins, carbohydrates, lipids, or any combination thereof.

In one illustrative example, the analyte may be a compound used to diagnose a particular condition in a subject such as but not limited to a human subject. For example, the analyte may be a marker of pregnancy such as Early Pregnancy Factor (EPF) which is released within hours of fertilization. The ability to detect EPF using the methods provided herein will therefore lead to a more sensitive determination of pregnancy at early time points post-fertilization. It may also be used to assess infertility in a subject. Thus, in some embodiments, the analyte will be EPF (or other pregnancy markers), the analyte-specific binding partners will be specific for EPF and may be antibodies or antigen-binding antibody fragments that bind to EPF, and the polymers may be nucleic acids such as DNA. The polymers may or may not have cleavable linkers between the locations of the two binding partners.

Binding Partners

The binding partners may include without limitation antibodies including but not limited to single chain antibodies, antigen-binding antibody fragments, antigens (to be used to bind to their antibodies, for example), receptors, ligands, aptamers, aptamer receptors, nucleic acids, small molecules, and the like.

The linkage between the polymer (e.g., nucleic acid) and the binding partner may be covalent or non-covalent depending on the strength of binding required for a particular application.

The sample is combined with a polymer pair or with a polymer (conjugated to analyte-specific binding partners), such as a nanoswitch, under conditions that allow binding of analyte-specific binding partners to their respective analytes if present in the sample. Those conditions may vary depending on the nature of the analyte and the binding partner. Those conditions may also take into consideration the stability of the polymer, binding partner and/or analyte. In some embodiments, the conditions may comprise a temperature at about 4° C., between 4-25° C., a pH between 5.5-7, and a physiological salt concentration. The temperature may be between 4-10° C., between 10-15° C., between 15-20° C., between 20-25° C., or about room temperature. The conditions may comprise inhibitors such as DNase inhibitors, RNase inhibitors, or protease inhibitors.

Copper-Free Click Chemistry and Snap-Chemistry and Method for Joining Molecules of Interest with DNA Oligonucleotide to Functionalize DNA Nanoswitch As described herein, the target regions or the oligonucleotides complementary thereto are conjugated to molecules of interest including for example analyte-specific binding partners. Sortase-mediated and amine-to-sulfhydryl chemistry (via sulfo-SMCC bifunctional reagent) can be used to conjugate the complementary oligonucleotide to protein as described in Koussa et al. 2014. Alternative approaches have now been tested and it has been found surprisingly that they produce high yields, while being less complicated to perform.

One such alternative conjugation approach involves copper-free click chemistry. Another alternative conjugation approach involves SNAP-tag systems. Both approaches can be used to conjugate proteins and other molecules of interest to oligonucleotides. This approach is described in greater detail herein.

Figure 7:
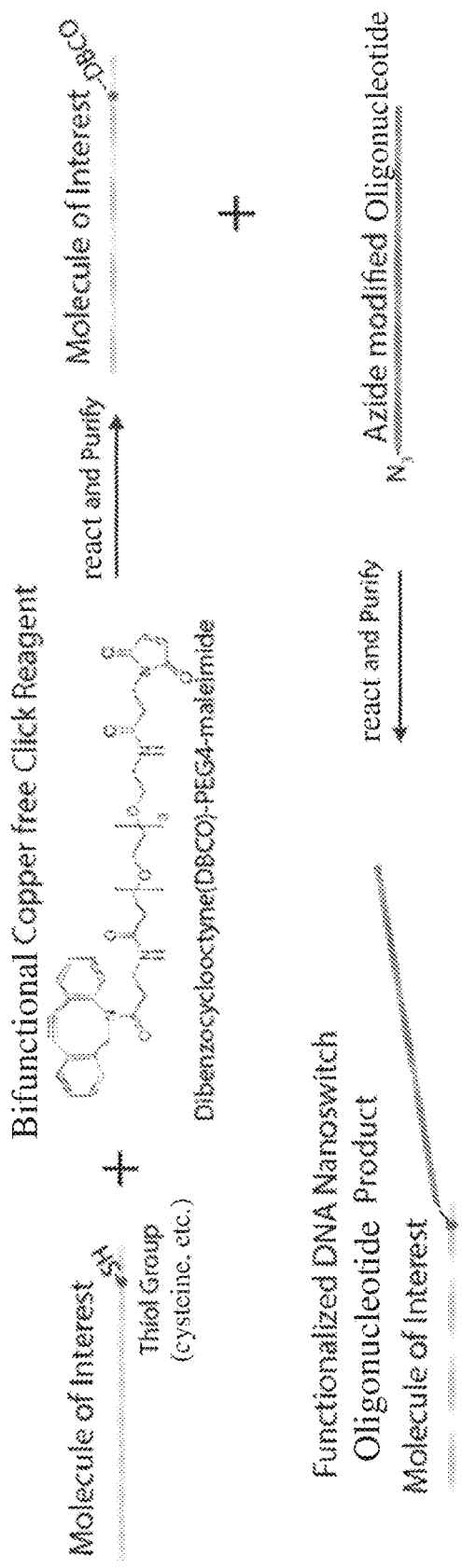
FIG. 7. Schematic of the sulfhydryl group (—SH) mediated attachment of oligonucleotide to a molecule of interest such as an analyte-specific binding partner.
Figure 8:
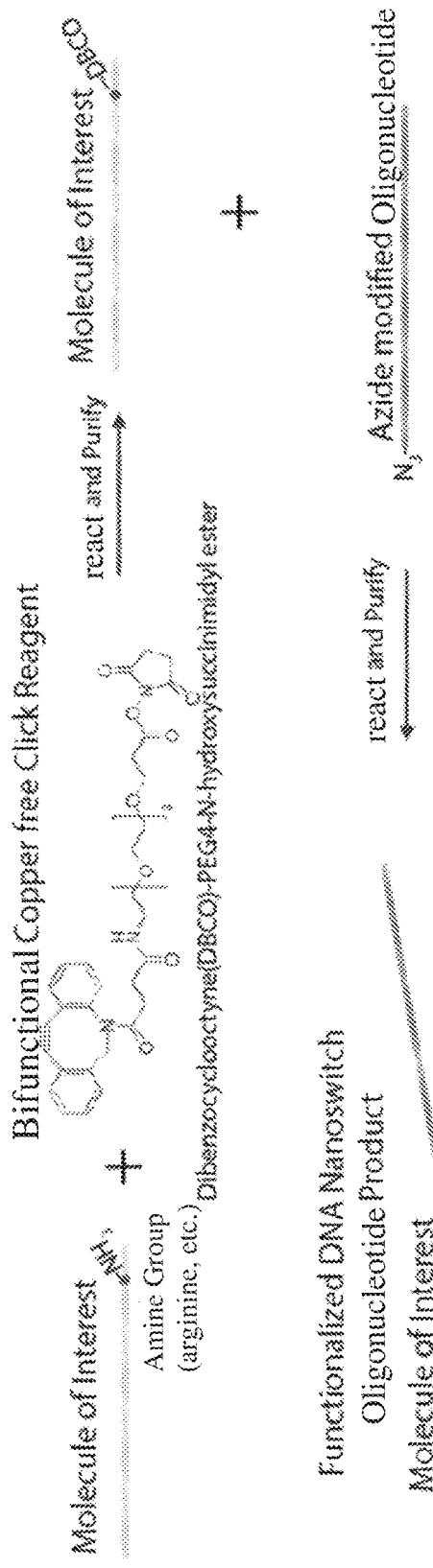
FIG. 8. Schematic of the amine group (—NH$_3$) mediated attachment oligonucleotide to a molecule of interest such as an analyte-specific binding partner.

The copper-free click chemistry approaches can be classified as sulfhydryl-group (—SH) attachment and amine-group (—NH$_3$) attachment approaches. In these approaches, protein or other molecules of interest containing thiol (e.g., in the form of cysteine, etc.) or amine (e.g., in the form of an arginine, lysine, etc.) reactive groups can be crosslinked to azide functionalized oligonucleotides through a bifunctional copper-free click reagent. There are two reaction steps in the crosslinking procedure. In the first step the thiol or amine groups are reacted with dibenzocycloctyne-PEG4-maleimide or dibenzocycloctyne-PEG4-N-hydroxysuccinimidyl ester, respectively. The dibenzocycloctyne labeled protein can further react with azide modified oligonucleotide in the second reaction step. The PEG4 linker in the copper-free click bifunctional reagent increases the solubility of the reagent. These reactions are shown in FIGS. 7 and 8.

These reactions may be modified in a number of ways. For example, the thiol group may be reduced by using equal molar (or more) thiol-free reducing agent such as tris(2-carboxyethyl) phosphine in the reaction mixture. As another example, after the first reaction step, any excess click reagent may be removed using, for example, a desalting column or dialysis membrane. In some instances, it is preferable to remove the excess click reagent since it can reduce coupling efficiency in the second reaction step if it is present in large molar excess.

In still another modification, the order of the reaction steps can be switched. Specifically, azide modified oligonucleotide may be reacted with the bifunctional copper-free click reagent in the first reaction step. In some instances, this may not be preferred since the maleimide or the N-hydroxysuccinimide-ester can undergo hydrolysis and lose its reactivity with thiol and amine, respectively.

In still another improvement, the amine-based reaction solution preferably should not contain any non-target amine such as tris buffer. Similarly, the solution preferably should not contain any free azide as may be present as a bacteriostatic agent.

Additionally, a high ratio of click reagent to molecule of interest (e.g., >10:1) in the first reaction step is also not preferred in some instances as it can lead to excess amine-to-DBCO conversion, resulting in the molecule of interest losing its functional amine group and multiple oligonucleotides per-molecule of interest getting crosslinked in the second reaction step. Lower ratios such as 2:1, 3:1, 4:1 or 5:1 may be used instead. The reaction may be performed with the lower ratio (e.g., 2:1) and then increased if necessary. If a high ratio is used, then a lower the ratio of oligonucleotide to activated molecule of interest may be used to reduce crosslinking of multiple oligonucleotides per single molecule of interest.

An alternative conjugation approach involves site-specific nanoswitch oligonucleotide attachment to fusion proteins that comprise the molecule of interest. Proteins of interest may be converted to fusion proteins comprising Snap- or Halo-Tags. The oligonucleotides can be easily functionalized with the respective Snap or Halo ligands, via amine chemistry or thiol chemistry. These coupling strategies have the advantage of site specific coupling, in addition to ensuring that a single oligonucleotide is coupled to each protein.

Improving Efficiency by Purifying Reactants and Products

The synthesis and assay methods provided herein can be impacted by the quality of the reactants including the oligonucleotides and scaffold nucleic acid. Similarly, it has been found that in some instances a nanoswitch can degrade, leading to less than optimal results. The presence of certain degraded or interfering reactants and their effect, sometimes significant effect, on the methods provided herein has not been recognized. Additionally, attempts to purify the reactants such as the oligonucleotides or the scaffold nucleic acid or in some instances the nanoswitch itself using prior art methods have not been optimal. Accordingly, provided herein are novel approaches for purifying reactants and products.

Separation of functionalized oligonucleotides from excess unfunctionalized oligonucleotides. Some embodiments involve purifying functionalized oligonucleotide from excess oligonucleotides. In the second reaction step of crosslinking a molecule of interest to an oligonucleotide, there may be unreacted oligonucleotides present at the end of the reaction. Such unreacted oligonucleotides, if not removed, may hybridize with their complementary target regions on the scaffold nucleic acid and reduce the yield of the final functionalized nanoswitch. Therefore, it may be beneficial in some instances to purify functionalized oligonucleotides from any excess unfunctionalized oligonucleotides. This can be achieved via gel purification techniques and devices such as but not limited to BluePippin™ or BioRad's Preparative Electrophoresis, although in certain instances this can be time consuming and prone to low yields. Improved electrophoretic methods are provided herein. These approaches are referred to as Real-Time Continuous Gel Electro-Elution and Reverse Gel Electro-Elution. Both are described in greater detail below.

Several non-electrophoretic methods are provided herein for purifying the functionalized oligonucleotide from excess oligonucleotides. These include:

His-tag purification. The molecule of interest may be conjugated to a polyhistidine-tag (e.g., by using recombinant technology). It is then possible to capture the functionalized oligonucleotide using an affinity chromatography matrix such as Ni-NTA agarose, followed by a washing step to remove excess unfunctionalized oligonucleotide, and a final elution step using buffer containing imidazole to release the captured oligonucleotide from the matrix.

Size exclusion chromatography. If the molecular weight of the molecule of interest is significantly larger than the molecular weight of the oligonucleotide, size exclusion chromatography may be used to separate functionalized oligonucleotides from unfunctionalized oligonucleotides.

High performance liquid chromatography. If the molecular weight of the molecule of interest is similar to the molecular weight of the oligonucleotide, high performance liquid chromatography may be used to separate functionalized oligonucleotides from unfunctionalized oligonucleotides.

Ammonium sulfate precipitation. If the molecule of interest is a protein, including an antibody, ammonium sulfate may be used to precipitate out the protein-oligonucleotide complex.

Separation of DNA nanoswitches from excess tiling oligonucleotides, fragmented DNA nanoswitch impurities, unfunctionalized molecules of interest, and functionalized oligonucleotides. This disclosure contemplates various methods for separation of DNA nanoswitches from various reactants such as fragmented nanoswitches, non-conjugated molecules of interest, such as analyte-specific binding partners, and excess functionalized oligonucleotides. The effects of these contaminants is described in detail below.

Excess tiling oligonucleotide. As described herein, in certain embodiments, DNA nanoswitches are synthesized using a large molar excess of tiling oligonucleotide that is added to linearized single-stranded scaffold such as M13, leaving the target regions single-stranded and available to hybridize with functionalized oligonucleotides. The large excess of free tiling oligonucleotides can act as non-specific hybridization sites for functionalized oligonucleotides, thereby interfering with the hybridization of the functionalized oligonucleotide to their respective complementary single-stranded target region.

Fragmented DNA nanoswitch. The circular M13 DNA scaffold starting material can contain impurity from random fragmentation. Upon specific linearization of the circular M13 starting material, the randomly fragmented M13 impurity can be visualized as a smear below the specific linear band in gel electrophoresis analysis. This impurity again can also interfere with DNA nanoswitch methodology.

Unfunctionalized molecule of interest. Unfunctionalized molecules of interest may remain after the crosslinking reaction, and may interfere with the hybridization of the functionalized oligonucleotide and its respective single-stranded target region.

Functionalized oligonucleotides. To increase the yield of the functionalized DNA nanoswitch yield, in the functionalization step, a large excess of functionalized oligonucleotide may be incubated with the DNA nanoswitch construct. After hybridization, excess functionalized oligonucleotide should be removed.

Looped nanoswitches versus unlooped nanoswitches. These purification or separation methods may be used, for example, to purify looped nanoswitches from linear or unlooped nanoswitches. Purified looped nanoswitches can be further treated to dialyze away the bound analyte or introduce a competitor that competes away binding of the analyte from the nanoswitch, rendering the nanoswitch linear yet capable of looped formation upon re-introduction of the analyte.

Functional nanoswitches from non-functional nanoswitches. After DNA nanoswitches have been formed, a significant fraction (sometimes −50%) of the final constructs are typically non-functional and not able to form loops. As will be appreciated, this may have negative consequences for a wide range of DNA nanoswitch applications. For example, for biomolecular interaction analysis, the ratio of looped versus unlooped DNA nanoswitches may not accurately reflect the difference in free energy between these two states, making it difficult to measure the Kd of molecular interactions from equilibrium measurements (the fraction of unloopable DNA nanoswitches tends to be quite variable, so it is difficult to account for this by simply adding an offset to the unlooped signal). Similarly, for detection applications, the brightness of the looped and unlooped bands may not directly reflect the chemical potential (and therefore the concentration) of analyte in solution. Additionally, a large unloopable population may reduce the sensitivity of detection applications as the linear band resulting from unloopable constructs may smear into the looped band, increasing the background and decreasing signal-to-noise. Having a large fraction of non-functional DNA nanoswitches also may reduce the efficiency of DNA nanoswitch experiments, both for single-molecule and bulk experiments.

One approach for solving this challenge is to purify looped constructs from unlooped constructs (and from free oligos, proteins, and anything else in the solution). As will be appreciated, after such a purification, all of the resulting constructs will be loopable, i.e. functional. According to some embodiments, such a purification may be performed via gel electrophoresis, including real-time continuous gel electro-elution and reverse gel electro-elution, as will be described. DNA separation also may be accomplished via topology. In other embodiments, methods for enriching loops using nanostructures that can "catch" the loops, e.g. a nano "ring toss" may be used.

In some embodiments, if an equilibrium distribution is desired, the loops may be allowed to re-equilibrate, with the final distribution of looped versus unlooped DNA nanoswitches reflecting the appropriate Kd/Boltzman weighting. As will be appreciated, for detection applications, one typically may want unlooped DNA nanoswitches that are functional (i.e. loopable). To obtain such unlooped DNA nanoswitches, one may start with pure looped construct, then dialyze out the analyte, or introduce a (removable) competitor that can bind to the analyte in order to shift the nanoswitch equilibrium distribution to mostly open, and then wait for the DNA nanoswitch population to re-equilibrate. This process also may be accelerated using heat or other perturbations.

Figure 9:
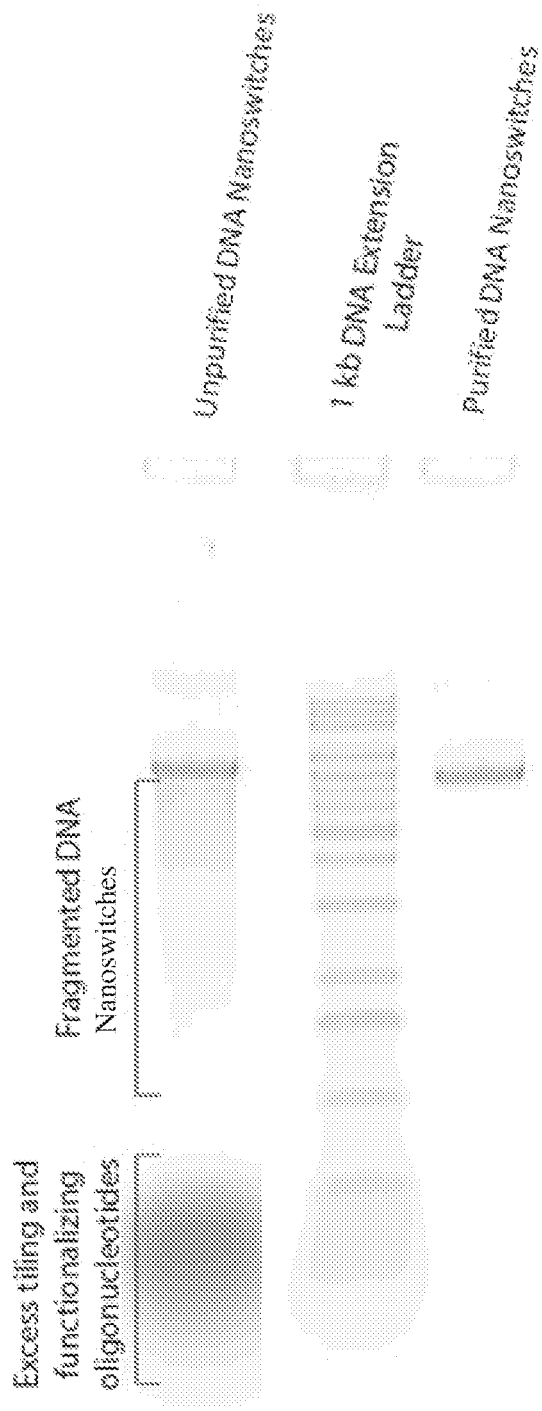
FIG. 9. Gel-electrophoresis purification technique.

One way of removing these impurities and/or purifying the product of interest is through gel electrophoresis. The recovery when using a gel electrophoretic approach is higher as compared to DNA PEG precipitation, Solid Phase Reversible Immobilization (SPRI)-based separation, or ethanol-based DNA extraction techniques (Qiagen, Zymo, etc.). In addition, some of these other techniques utilize alcohol solvent that can damage the molecule of interest including for example proteins. As an example, the BluePippin™ instrument (Sage Science) may be used to carry out gel electrophoresis based purification. The BluePippin™ instrument uses a dye-free, pre-cast agarose gel that can be used to separate and then extract DNA nanoswitch. The separation that can be achieved using BluePippin™ is shown in FIG. 9, which shows the separation of DNA nanoswitches from excess tiling and functionalized oligonucleotides.

Other gel-electrophoresis approaches can be used as an alternative to BluePippin™ purification. Some improved electrophoretic methods are Real-Time Continuous Gel Electro-Elution and Reverse Gel Electro-Elution, both of which are described herein.

The two common methods for recovering the desired material after the separation by gel-electrophoresis are gel electro-elution (McDonell et al. 1977) or direct band elution (Hansen et al. 1993, Bellot et al. 2011). In the gel electro-elution method, DNA in the gel is visualized with fluorescent dyes (ethidium bromide, SYBR stains, YOYO, etc.) or a UV shadowing technique (Hassur et al. 1974) to locate the desired band to be isolated from the gel for extraction. The extraction of DNA from the isolated gel can be carried out using electro-elution or spin-column centrifugation (Thuring et al. 1975). DNA staining dyes can interfere with downstream applications, and therefore a dye removal process such as ethanol-based solution washing is often required after purification. However, molecules that are coupled to the nanoswitch can be denatured with the solvent washes. Furthermore, the nucleic acid that constitutes the nanoswitch is itself subject to photo-damage by fluorescence stain or UV (Ravanat et al. 2001). Besides the issues of dye contamination and nucleic acid degradation, the current techniques are labor intensive and require significant training to perform.

Applicant has recognized that by eliminating the requirement of direct visualization of the desired band during purification, various advantages may be realized. The electrophoretic approaches provided herein eliminate the requirement of direct visualization of the desired band during purification, preserving the integrity of the molecule of interest, and reduced user inputs. Applicant has further recognized that advantages may be realized by incorporating the purification step into a conventional electrophoresis, instead of conducting the purification in subsequent electrophoresis protocols or by using other known protocols for isolating DNA from the gel. To achieve this, we have developed two methods: real-time continuous gel electro-elution and reverse gel electro-elution.

Real-Time Continuous Gel Electro-Elution

According to some embodiments, DNA purification may be achieved via real-time continuous gel electro-elution apparatus ("the apparatus"). That is, DNA may be removed from the gel during a conventional electrophoresis. In such embodiments, the gel may include a first well (a "loading well") for loading a sample to be purified and a second well (a "collection well") for collecting the purified sample. As will be appreciated, the second well may be located in a position downstream of a direction of migration of the sample travelling from the first well (loading well) through the gel. In some embodiments, the conventional gel electrophoresis is run until the component to be isolated from the DNA sample, such as linear DNA, reaches the collection well.

Thus, we modified the conventional gel electrophoresis setup to include a collection well in the downstream position of the migration direction. A fluid-flow apparatus that continuously collects fluid from the collection well and maintains a constant volume of fluid within the collection well may also be used. The fluid drawn out of the collection well may be split into fractions downstream as shown in FIG. 15B.

Since all components in the sample can be purified into individual fractions continuously, this method allows purification of many components from a single mixture. More importantly, the need to visualize the desired band for elution is completely eliminated. Subsequent conventional gel electrophoresis analysis can be carried out to identify the fraction that contains the desired material. Another advantage of this method is the flexibility of choosing the collection buffer allowing the user to choose the final sample buffer rather than being limited to high viscosity or gel electrophoresis running buffer.

Figure 16:
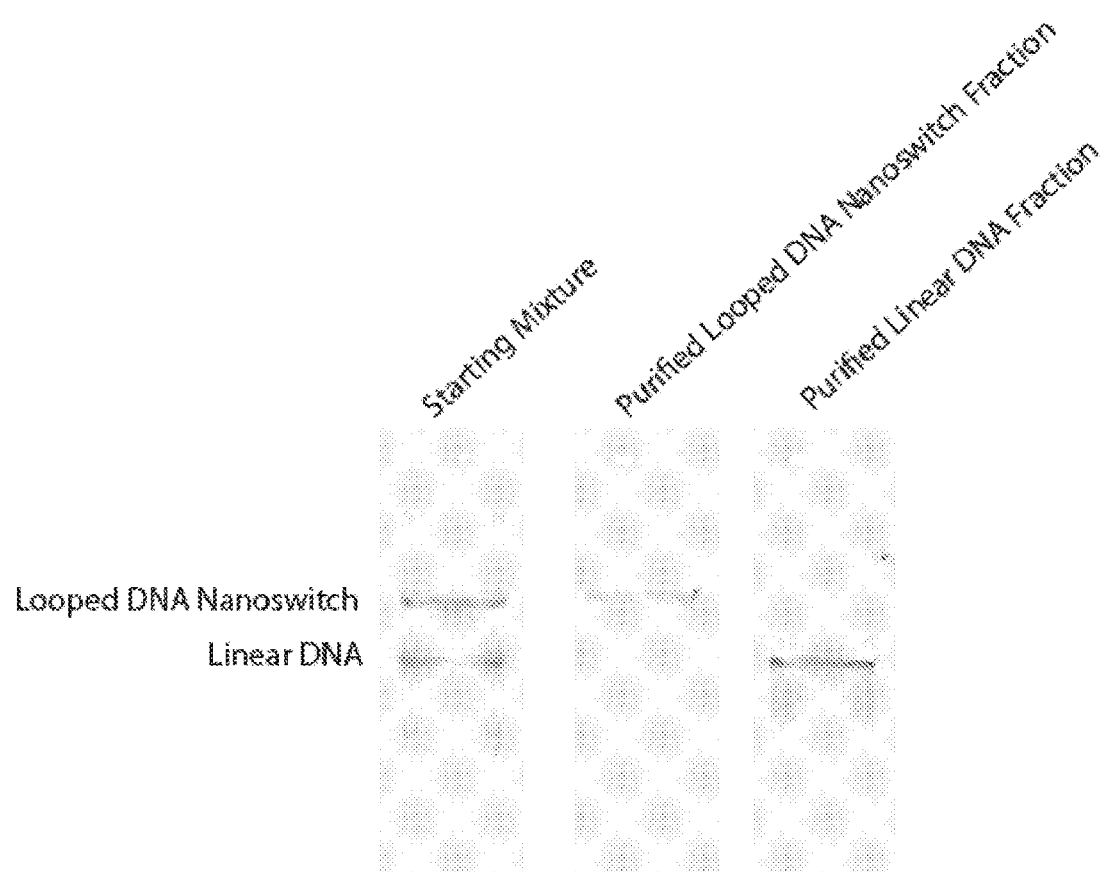
FIG. 16. Downstream agarose gel electrophoresis analysis of the fractions obtained through the real-time gel electro-elution method. The looped DNA nanoswitch is purified from the mixture containing the linear DNA.

As an example, we used the real-time continuous gel electro-elution method to separate and purify looped DNA nanoswitch (Koussa et al. 2015, Halvorsen et al. 2011) from a mixture of looped and linear DNA. The results are shown in FIG. 16.

If only a small number of bands are needed, it may be sufficient to simply pipette the desired sample from the collection well as it passes into the well. We have successfully done this to purify looped DNA nanoswitches from unlooped DNA nanoswitches, greatly enriching the "loopable" fraction of nanoswitch constructs.

In some embodiments, the conventional gel electrophoresis is run until a component to be isolated from the DNA sample, such as linear DNA, reaches the collection well. In some embodiments, the apparatus includes a fluid-flow device that is arranged to continuously collect fluid from the collection well and maintain a constant volume of fluid within the collection well. For example, once the fluid has been removed from the collection well additional buffer may be added. In such embodiments, the fluid drawn out of the collection well is split into fractions downstream (see FIGS. 15A and 15B). As will be appreciated, the fraction may include the component isolated from the DNA sample and/or buffer.

In some embodiments, more than one component may be purified via real-time continuous gel electro-elution. For example, the protocol may be run, with samples being aspirated from the collection well and into one or more fraction, until such time as a first component travels from loading well to the collection well. In such embodiments, the fluid flow device also may be arranged transfer fluid back into the collection well. Once the first component has been isolated, this protocol may be continued to aspirate additional fluid from the collection chamber and isolate a second, third, fourth, etc., component into second, third, fourth, etc., fractions.

Such a real-time continuous gel electro-elution may allow purification of many components from a single mixture. As will be appreciated, the desired band for elution need not be visualized prior to aspirating the fluid from the collection well. That is, the sample need not be treated with a dye to achieve separation of the components. In some embodiments, subsequent conventional gel electrophoresis analysis may be performed to confirm that the collected fraction contains only the desire material. In some embodiments, continuous gel electro-elution may provide flexibility in choosing the collection buffer, which may allow the user to choose the final sample buffer rather than being limited to high viscosity or gel electrophoresis running buffer.

Figure 15A:
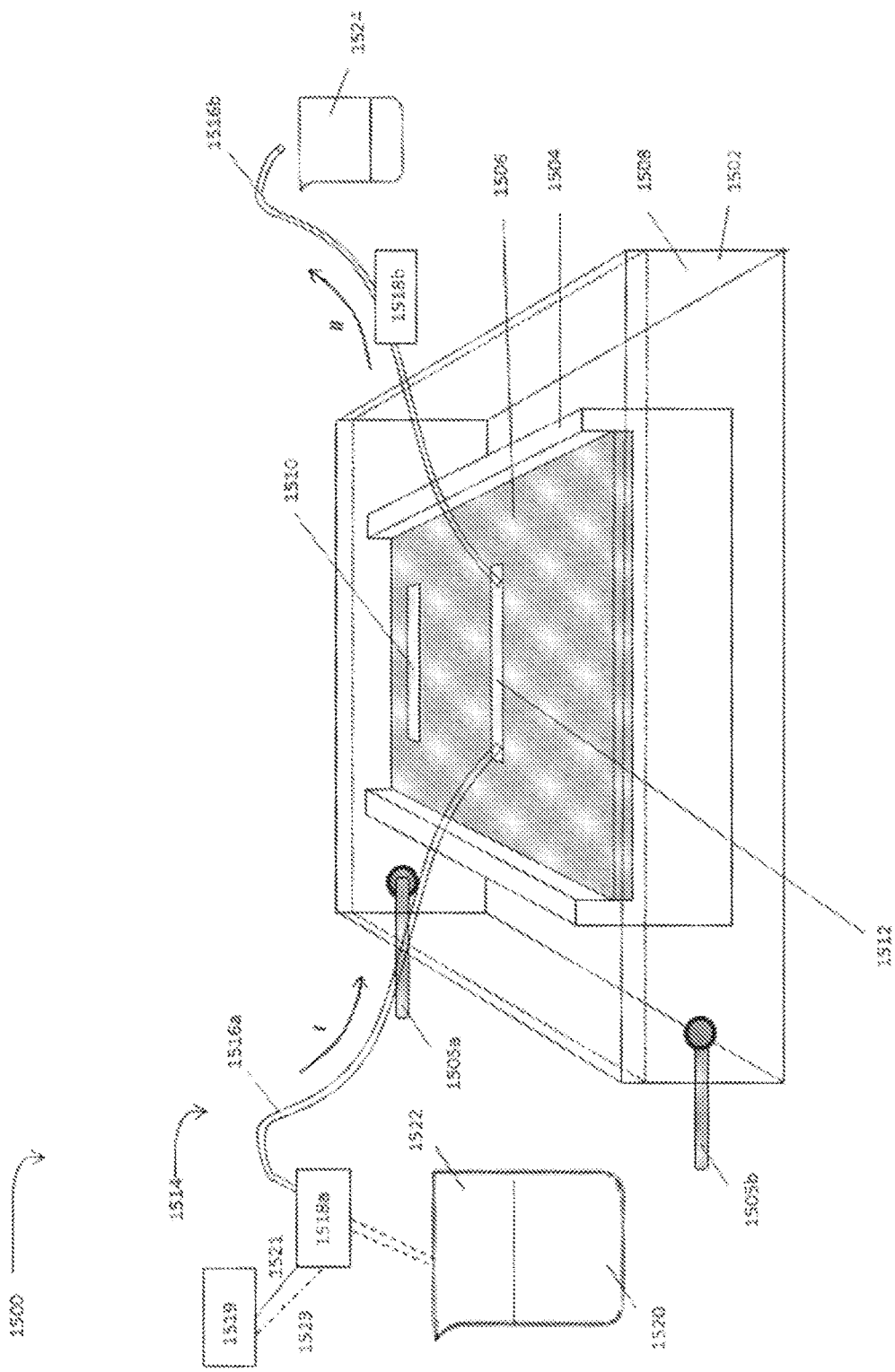
FIG. 15A. Schematic representation of real-time continuous gel electro-elution apparatus, according to one embodiment.
Figure 15B:
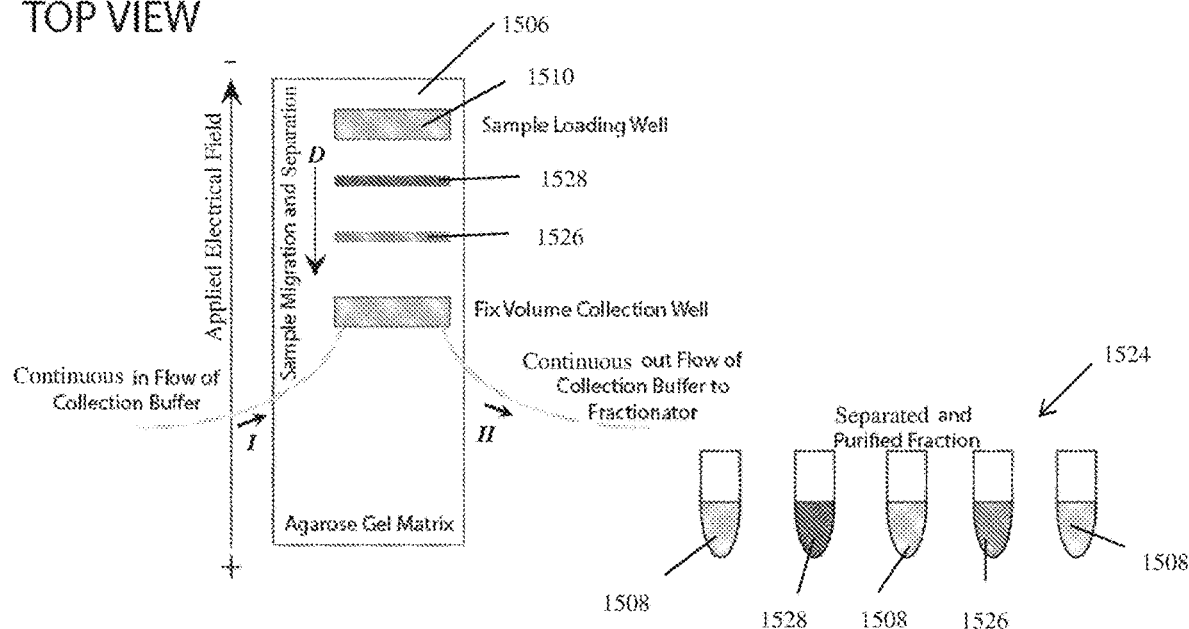
FIG. 15B. Schematic of the real-time continuous gel electro-elution set up and process.
Figure 15B:
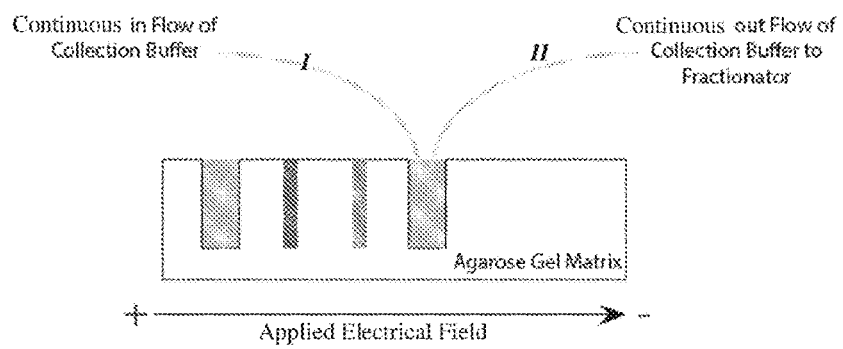

Turning now to FIG. 15A, a real-time continuous gel electro-elution apparatus ("the apparatus") 1500 is illustrated. As shown in this figure, the apparatus 1500 includes a chamber 1502 with a tray 1504 on which a gel 1506 is placed. The chamber is connected to electrodes, 1505*a*, 1505*b*, which may be arranged to create a negative and positive electrical field, respectively. As will be appreciated, the chamber 1502 is filled with a buffer 1508. In some embodiments, the buffer 1508 in the chamber is different from the buffer loaded into the collection well during the electrophoresis protocol, although the same buffer may be used.

In some embodiments, the gel 1506 includes first and second wells 1510, 1512. In such embodiments, a sample to be purified may be loaded into the first well 1510, with the second well 1512 being used to collect one or more components that migrate from the first well 1510 to the second well 1512, the one or more components being aspirated from the second well 1512 into fractions.

Although the gel in FIG. 15A is shown as having only one loading well and one collection well, it will be appreciated, that the gel may have one or more loading wells and one or more corresponding collection wells. For example, the gel may have two loading wells and only one collection well. The gel also may include two loading wells and two corresponding collection wells. In such embodiments, the apparatus may include multiple tubes for allowing fluid to be continuously aspirated from each of the collection wells and into fractions.

In some embodiments, as also shown in FIG. 15A, the apparatus 1500 includes a fluid-flow device 1514 for aspirating one or more components from the collection well 1512 and supplying a collection buffer into the collection well 1512. In some embodiments, the fluid-flow device 1514 includes first and second tubes 1516*a*, 1516*b* for supplying and removing fluid from the collection well 1512. As illustrated in FIG. 15A, each of the first and second tubes 1516*a*, 1615*b* may be connected to respective first and second pumps 1518*a*, 1518*b* arranged to transfer the fluid into and out of the collection chamber, respectively. For example, the first pump 1518*a* may transfer a buffer 1520 from a fluid supply chamber 1522 to the collection well 1512 (see the arrow labeled I), and the second pump 1518*b* may transfer fluid from the collection well 1512 to a fraction collection chamber 1524 (see the arrow labeled II). As will be appreciated, the pumps 1518*a*, 1518*b* may be arranged to apply a pressure (e.g., a positive or negative pressure) to transfer the fluid into and out of the collection well 1512.

In such embodiments, the fluid-control device (such as the first and second pumps 1518*a*, 1518*b*), may be connected to a control panel 1519 that controls the pumps to supply and remove fluid from the collection chamber. As will be appreciated, the control panel 1519 may be directly connected (e.g., via a wire) 1521 to one or more pumps, or it may be wirelessly 1523 connected to one or more pumps.

Although the fluid-flow device 1514 is show as having first and second pumps connected to respective tubes, it will be appreciated, that a single pump may be connected to both tubes. In such embodiments, the pump may be activated to first remove a sample fluid from the collection well via the second tube 1615. Once the fluid has been removed, the pump may then be activated to transfer fluid from the fluid supply chamber 1522 to the collection well 1512 via the first tube.

The control panel may be arranged to apply a pre-selected protocol, which may instruct the pumps 1518*a*, 1518*b* to supply and/or remove fluid from the collection well 1512 at certain intervals, such as every 10 seconds, 30 seconds, 2 minutes, 10 minutes, 20 minutes, etc. The control panel instruct the pumps 1518*a*, 1518*b* to supply and/or remove the fluid from the collection well 1512 for a certain duration of time, such as for 2 seconds, 3 second, 5 seconds, etc.

An example of real-time continuous gel electro-elution is shown in FIG. 15B, which illustrate top and right side views, respectively, of a gel 1506 used to separate and purify looped DNA nanoswitches (Koussa et al. 2015, Halvorsen et al. 2011) from a mixture of looped and linear DNA. As shown by the bands in the gel in FIG. 15B, the liner DNA 1526 and looped DNA nanoswitches 1528 have moved downstream (see the arrow labeled d) and have separated from one another in the gel 1506. As will be appreciated, the gel electrophoresis may continue to be run until the liner DNA reaches the collection well 1512 and is aspirated into a fraction 1524. the gel electrophoresis may still continue to be run until the looped DNA 1528 reaches the collection well and is aspirated into a fraction 1524. As shown in these FIG. 15B, the fluid-flow device has aspirated five purified fractions during the gel electrophoresis. As shown, three fractions 1508 having buffer were collected. A single fraction of each the looped DNA 1528 and linear DNA 1526 were also collected.

FIG. 16 illustrates supplemental gel electrophoresis analysis that have been conducted to test the composition of the fractions aspirated from the collection well, as compared to the composition of the sample loaded into the loading well. As shown in this figure, the initial sample had both looped DNA and linear DNA. A first fraction aspirated from the collection well had only linear DNA, and a second fraction collected from the collection well had only looped DNA. As will be appreciated, such results suggested that the above-described method of real-time continuous gel electro-elution is success in isolating components in a starting sample.

Although the apparatus has been shown and described as continuously aspirating fluid from the collection well, it will be appreciated that if only a small number of bands are needed, it may be sufficient to simply pipette the desired sample from the collection well as it passes through the collection well. Such a process has been shown to be successful to purify looped DNA nanoswitches from unlooped DNA nanoswitches, greatly enriching the "loopable" fraction of nanoswitch constructs.

Reverse Gel Electro-Elution

The reverse gel electro-elution method is capable of removing undesired material (e.g., DNA, RNA, protein, etc.) that has higher mobility (i.e., faster migration velocity) than desired material (e.g., looped nanoswitches), without direct visualization of the undesired material.

To achieve this, the gel used for separation is arranged into two sections (or portions) arranged in the direction of migration. The first section contains the sample loading well which is used for both loading the sample as well as recovering the desired material from the sample. The second section, which is located downstream of the first section, is used for trapping and removing the undesired material.

Figure 17A:
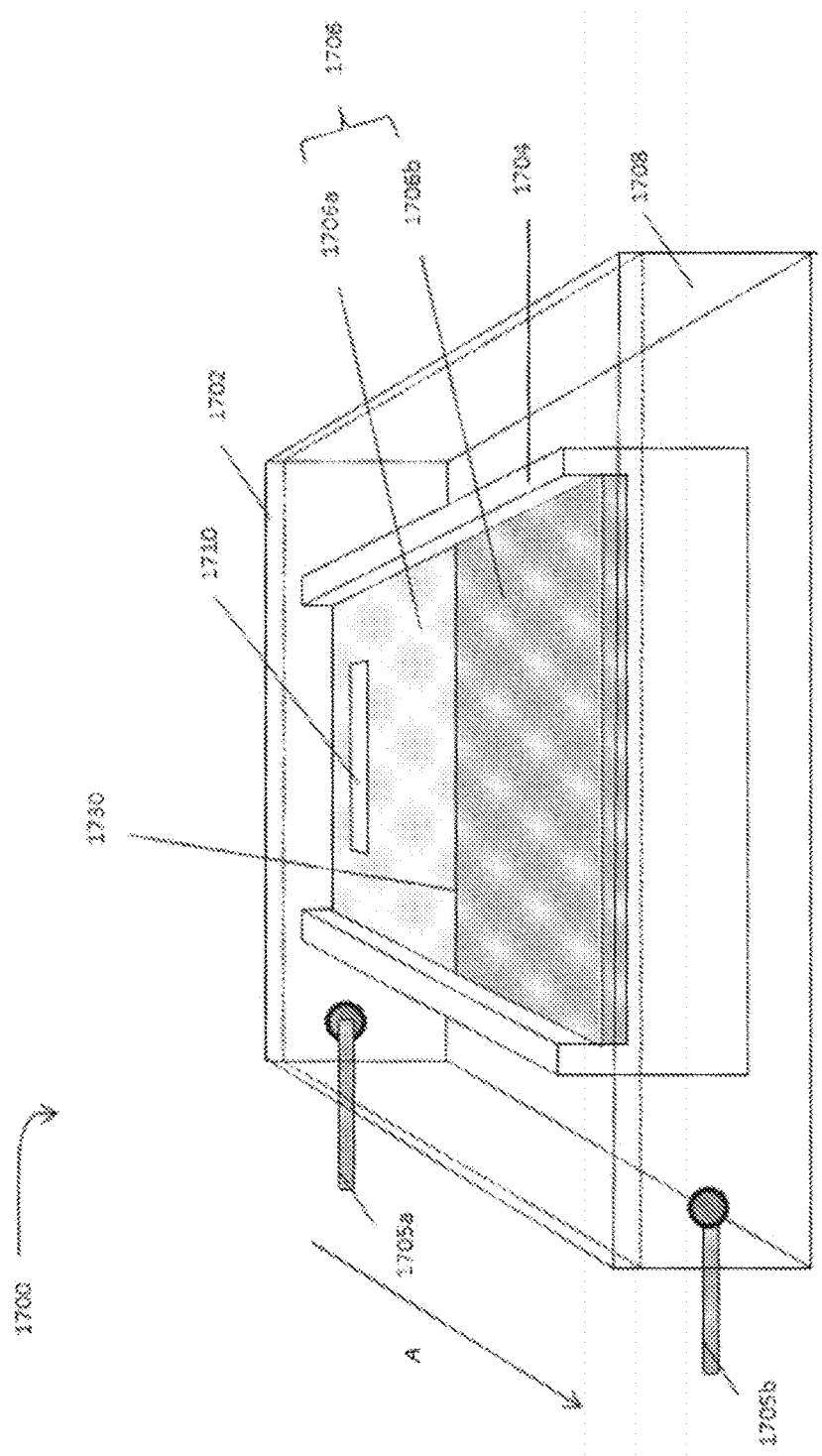
FIGS. 17A and 17B. Schematic representations of a reverse gel electro-elution according to various embodiments.
Figure 17B:
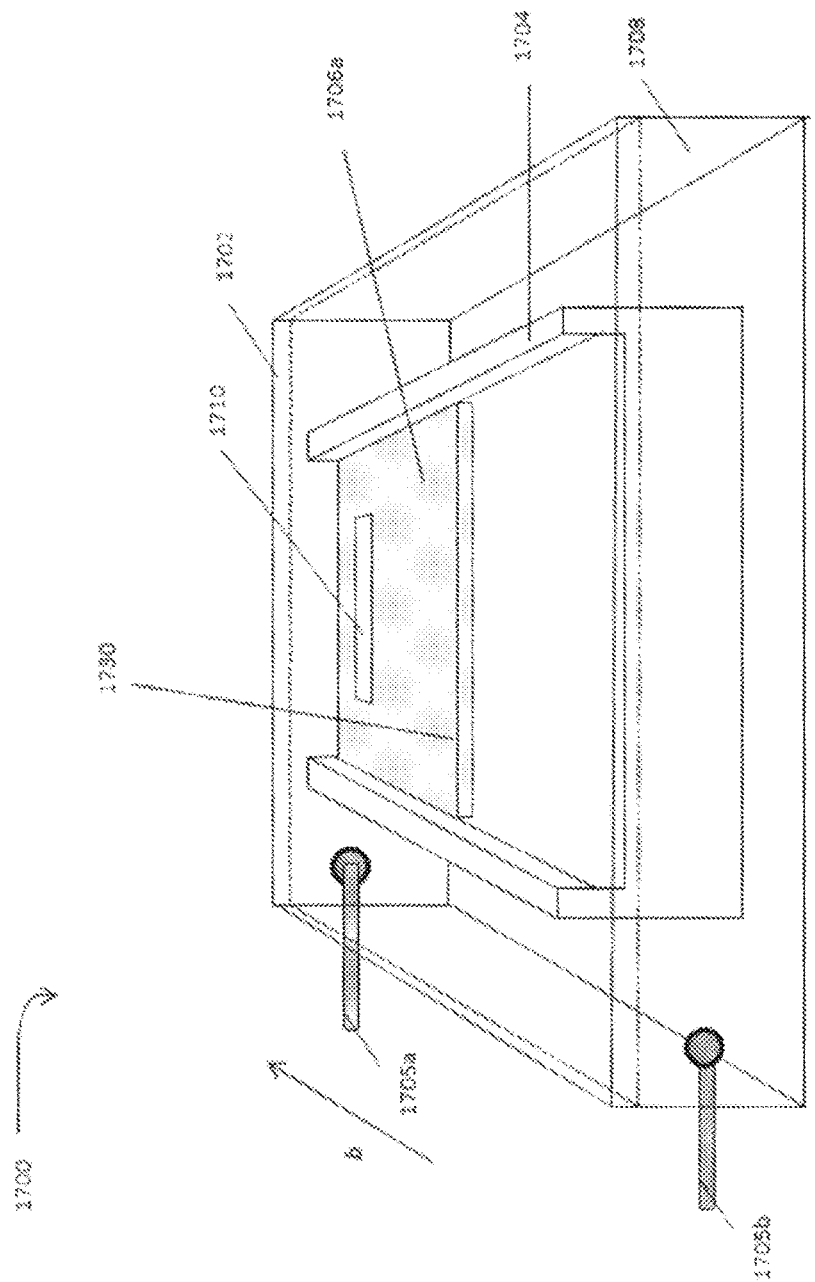
Figure 17C:
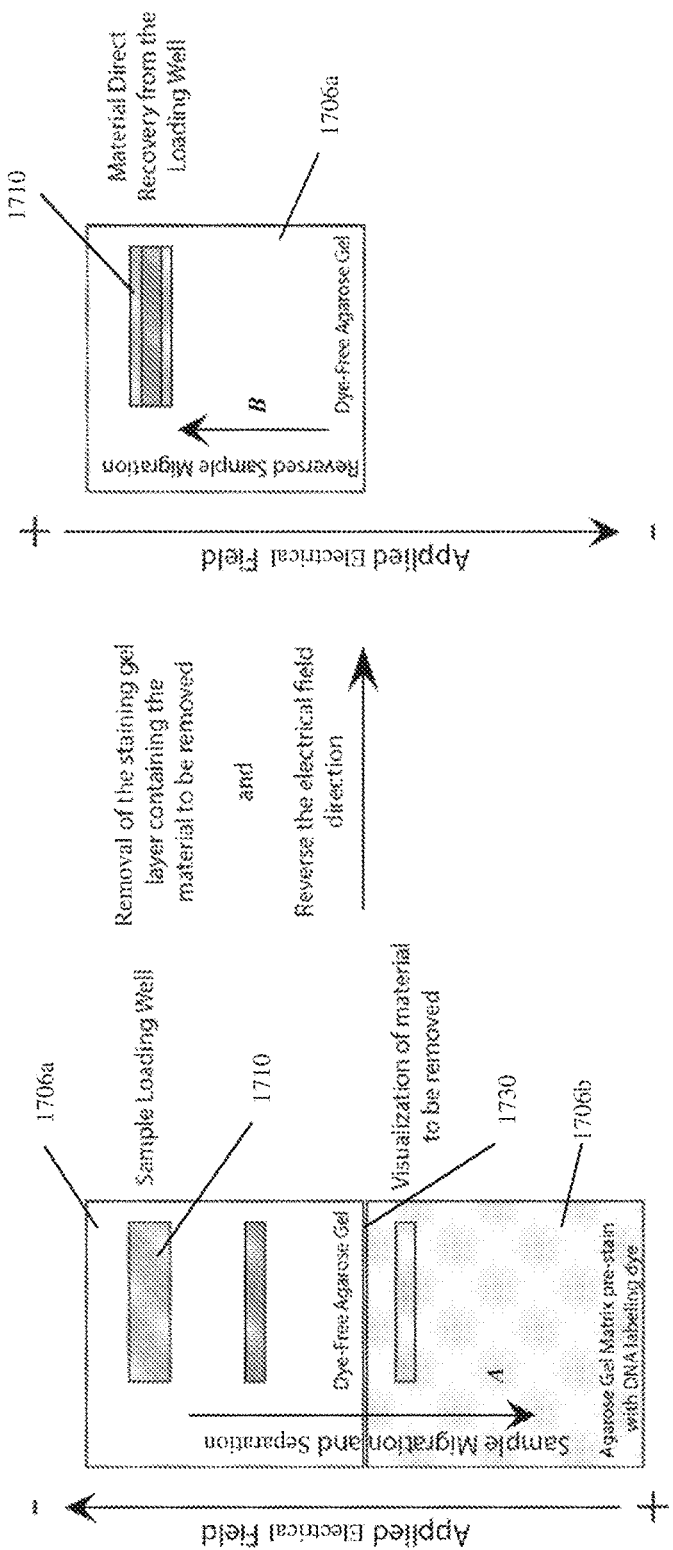
FIG. 17C. Illustration of the reverse gel electro-elution method with a negatively charged molecule such as DNA. The Figure illustrates the placement of two gels side-by-side in the direction of current. The first gel, referred to herein as the "top" gel, contains the sample loading well and preferably will be dye-free (i.e., it contains no nucleic acid staining dye such as an intercalator). The second gel, referred to herein as the "bottom" gel, contains dye (i.e., it contains nucleic acid staining dye such as an intercalator). The presence of such dye allows detection of the undesired material that is to be removed. Once the undesired material migrates into the "bottom" gel, it will be apparent because it will be bound by the dye. Once such undesired material is detected in the "bottom gel", that "bottom gel" is removed (e.g., it may be cut away from the "top gel" and the electrical field is reversed, causing the desired material from the original sample to migrate back to the elution well for collection.

A schematic of reverse gel electro-elution is illustrated in FIGS. 17A-C. In this particular example, the first gel section is free of nucleic acid staining dye whereas the second gel section contains such dye.

In the first step, after loading the sample in the loading well, an electric field is applied and the negatively charged components begin to migrate into the first gel section and towards the second gel section. The electric field is turn off once all the undesired material is visualized in the second gel section by virtue of the nucleic acid stain. The second gel section is removed and a reverse electric field is applied causing the desired material to migrate back into the initial loading well, from which it is then recovered.

Generally, for the material to migrate back to the loading well, the run time is set to be equal to the run time in the first forward step with the same electrical field strength. For maximizing the recovery, a piece of dialysis membrane may be added to the top-side of the loading well to keep the sample within the loading well while also increasing the reverse run time for example up to 10 minutes relative to the forward run time. This ensures that more and perhaps all of the desired material is captured. Beside dialysis membrane, high viscosity solution such as a buffer containing high percentage of PEG or sucrose can be added to the loading well before the recovery reverse run. In addition, continuous gel electro-elution can be implemented to the loading well to collect and fractionate the sample.

To that end, embodiments disclosed herein include a gel having a first well arranged to acts as both the loading well and the collection well. In use, the apparatus is arranged such that the electrodes have a first configuration for moving the components in the sample in a downstream direction. Once the undesired components of the sample (e.g., the linked DNA) have reached a desired location on the gel, a portion (or section) of the gel having those components may be removed. Next, the polarity of the electrodes may be reversed, and the gel electrophoresis may be run until the desired component (e.g., the looped DNA) returns to the well for collection. As will be appreciated, the desired component may be removed from the collection sample via a pipette. The fluid in the collection well also may be continuously removed during the reverse gel electrophoresis, as with other embodiments.

As shown in FIG. 17A, similar to continuous gel electro-elution, the reverse gel electro-elution apparatus 1700 includes a chamber 1702 with a tray 1704 on which a gel 1706 is placed. The chamber is connected to electrodes, 1705a, 1705b, which may be arranged to have first configuration (e.g., negative and positive electric fields, respectively) during a first portion of the electrophoresis protocol and a second, opposite configuration (e.g., positive and negative, respectively) during a second portion of the protocol. As will be appreciated, the chamber 1502 is filled with a buffer 1708.

As shown in FIG. 17A, the gel may include first and second sections, 1706a, 1706b defined along a longitudinal axis, the longitudinal axis corresponding to the direction of migration of the components in the sample towards and away from a well 1710. As shown in FIGS. 17A and 17B, the well 1710 is located in the first gel section 1706a includes. In some embodiments, a sample may be loaded into the well and may travel into the first and/or second gel sections 1706a, 1706b. As described, the second gel portion 1706b may be used trap and remove the undesired material.

In use, a conventional gel electrophoresis is performed, with the first and second electrodes 1705a, 1705b having negative and positive charges, respectively, and a direction of migration moving downstream of the chamber 1710, as noted by the arrow labeled A. Once the undesired component(s) has reached the second, downstream gel portion 1706b, the electrophoresis may be stopped, and the second portion 1706b of the gel may be removed. For example, the gel 1706 may be cut at line 1730 and the second portion may be removed. Next, as shown in FIG. 17B, the polarity of the first and second electrodes may be reversed, such that the first electrode carries a positive charge and the second electrode carries a negative charge. The electrophoresis protocol may again be run until the desired component has reached the channel 1710. In such embodiment, the direction of migration is reversed, as shown by the arrow labeled B. The desired component may then be aspirated from the chamber 1710.

As will be appreciated, the first and second portions of the gel may be equal in length (e.g., first and second halves of the gel), although they may have any suitable length in other embodiments. That is, the first and second gel portions may have different lengths. Without wishing to be bound by theory, the length of the first and second gel portions may correspond to the position of the migrated components on the gel with the components are moving in a downstream direction.

As will be described, a variety of techniques may be used to track and trap the undesired components of the DNA sample (e.g., the linear DNA) in the second portion 1706b of the gel 1706. As will be appreciated, the undesired components may be tracked to confirm if and when the undesired components have reached the second gel portion 1706.

For example, as shown in FIG. 17C, the first portion 1706a of the gel 1706 may be free of staining dye while the second gel portion 1706b may contains DNA dye. In such embodiments, after loading the sample to the loading well 1710, an electric field is applied for the components of the sample to move and separate between the first and second gel portions. As with other embodiments, the components migrate downstream of the loading well 1710 (see the arrow labeled A). Once the undesired material is visualized in the second portion 1706b of the gel (e.g., by looking for the dyed band), the electric field may be turned off. The second gel portion 1706b may then be removed, as shown in FIG. 17C. A reverse electric field may then be applied to cause the desired material to migrate back into the initial loading well for recovery (see the arrow labeled B).

Generally, for the material to migrate back to the loading well, the run time is set to be approximately equal to the run time in the first forward step with the same electrical field strength. In some embodiments, to maximize the recovery, a piece of dialysis membrane may be added to a top-side of the loading well to keep the sample within the well, while the reverse run time can be increased up to 10 mins relative to the forward run time. In addition to, or in place of, a dialysis membrane, high viscosity solutions such as a buffer containing high percentage of PEG or sucrose can be added to the loading well before the recovery reverse run. In some embodiment, in the recovery reverse run, a fluid-flow device may be used to collect and fractionate the sample.

Figure 18:
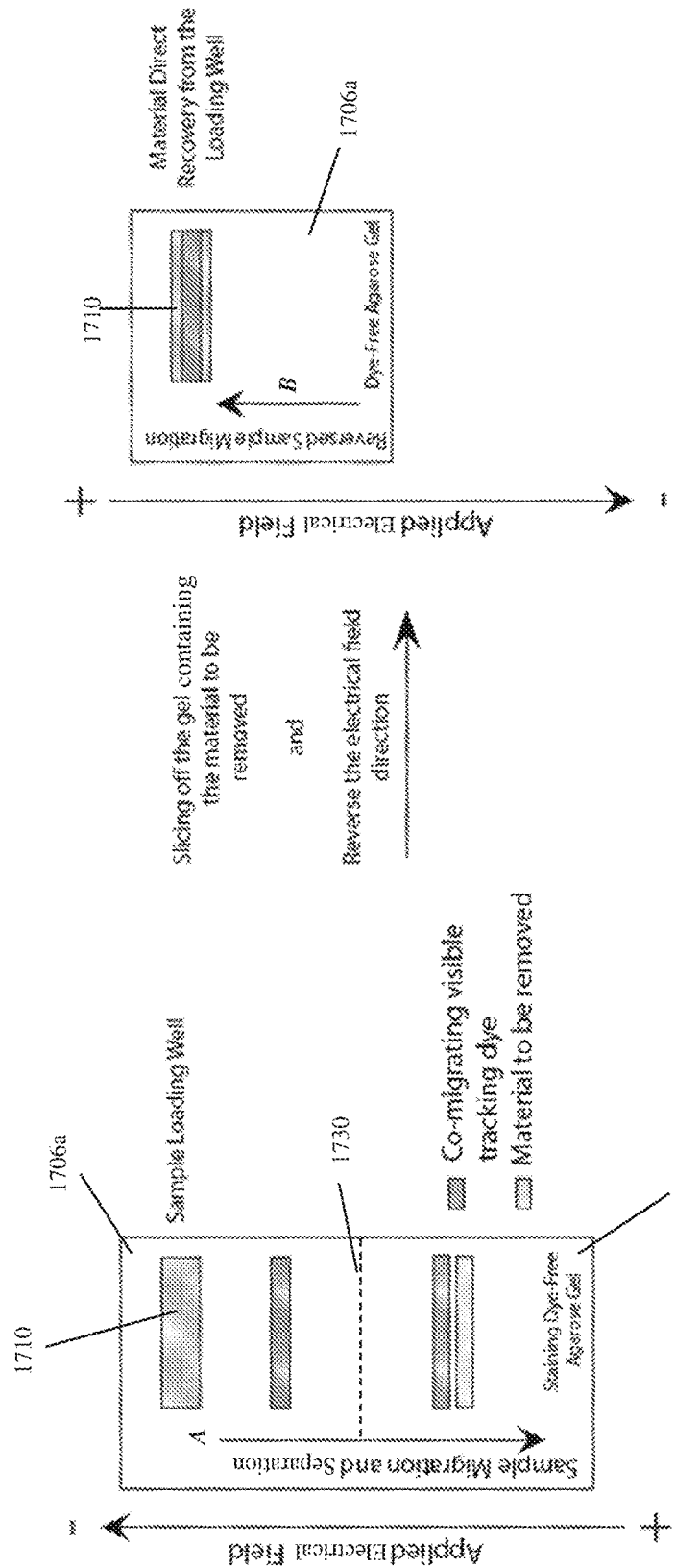
FIG. 18. Schematic of a variation of the reverse gel electro-elution method. In this example, the sample is run with a tracking dye that co-migrates with undesired material in the sample. The tracking dye may be added to the sample prior to running or the tracking dye may be run alone in an adjacent lane. The Figure illustrates the situation in which the tracking dye is added to the sample. Once the undesired material has migrated a sufficient distance (as indicated by the migration of the tracking dye), then this section of the gel may be removed (e.g., sliced away with a razor), following with the current may be reversed and the desired material may be collected upon its migration into the original sample loading well.

In some embodiments, instead of using a visible dye the second gel section, a labelling stain that directly binds to the undesired material for visualization may be used dyes. As will be appreciated, such a dye may be chosen such that it binds only to the undesired material and not the desired material. As such, the undesired material may be visible and removed once it has travelled into the second gel portion. In still another embodiment, as shown in FIG. 18, a tracking dye (orange G, bromophenol blue, xylene cyanol, etc.) may be added to the sample, the tracking dye co-migrating between the desired and undesired material under the tuned gel condition (agarose percentage, temperature, applied voltage, etc.). As will be appreciated, once the co-migrating tracking dye has reached the second gel portion 106b and is visualized by the user, the second gel portions 106b may be removed (removing the undesired components). The electric field may then be reversed such that the desired sample may migrate back to the well 1710.

Orange G and bromophenol blue gel electrophoresis tracking dyes (components of Promega Blue/Orange Loading Dye, 6×) migrate slower than a 60 bp size oligonucleotide and faster than the linear DNA nanoswitch under the running condition of 0.5×TBE, 0.7% agarose and 4.7 volt/cm. Therefore Orange G and bromophenol blue tracking dyes are useful in identifying the region of the gel that contains the excess oligonucleotides, used to make the nanoswitches, in the reverse gel electro-elution method and consequently which is to be removed Xylene cyanol FF gel electrophoresis tracking dye (component of Promega Blue/Orange Loading Dye, 6×) migrates with a 6500 bp size linear dsDNA under the running condition of 0.5×TBE, 0.7% agarose and 4.7 volt/cm. Therefore Xylene cyanol FF tracking dye is useful in purifying the looped DNA Nanoswitches in the reverse gel electro-elution method.

Although the co-migrating dye has been shown as being mixed with the sample in FIG. 18, in other embodiments, the co-migrating dye may be added to a neighboring tracking lane (not shown) on the same gel. As with other embodiments, once the tracking dye has reached the second portion of the gel, the second gel portion may be removed (along with the undesired components). The reverse the electric field may then be applied to cause the desired sample to migrate back to the well.

Figure 19:
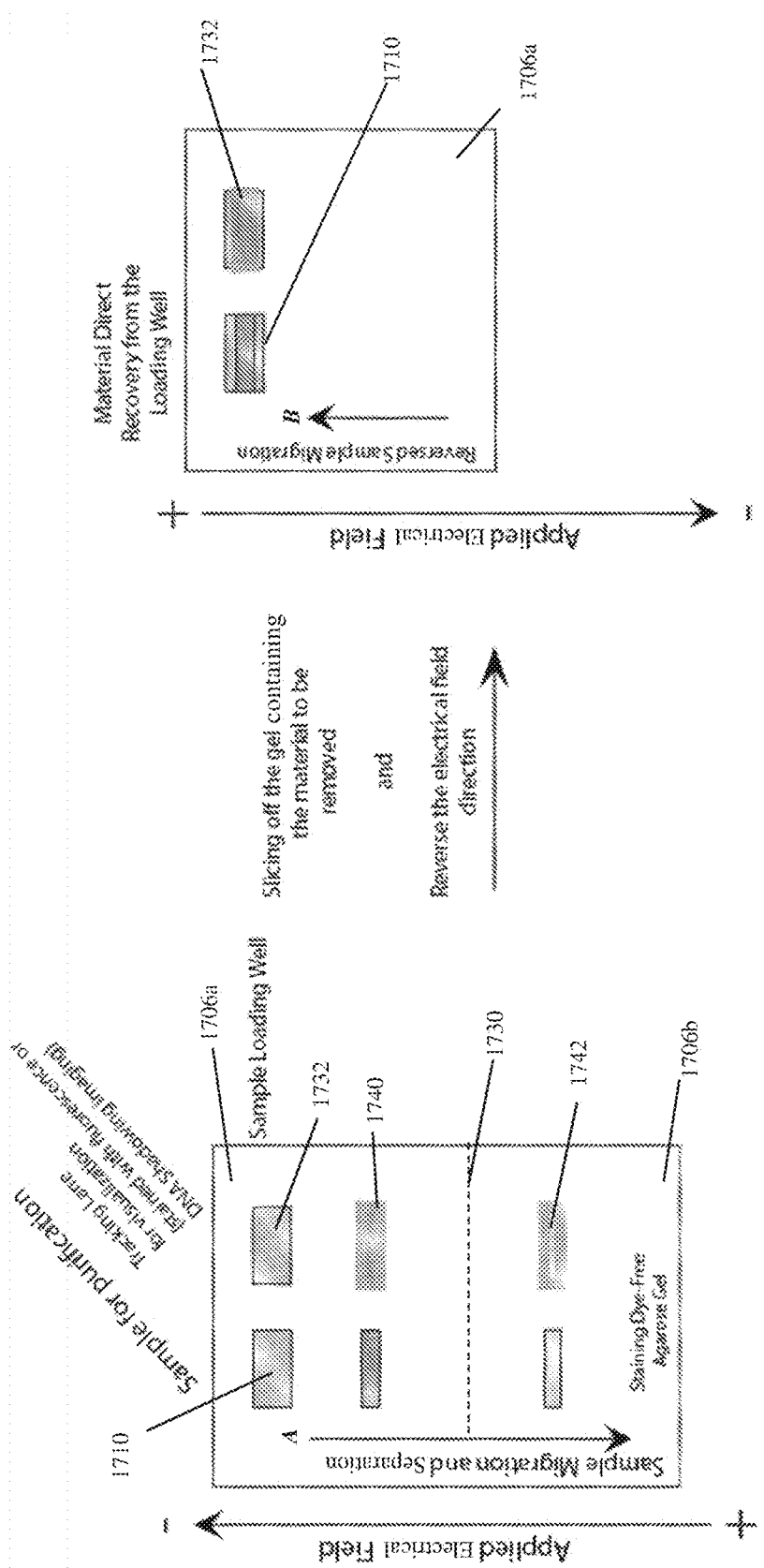
FIG. 19. Schematic depicting an additional variation of the reverse gel electro-elution method. Here, an aliquot of the sample is run in an adjacent lane, and such aliquot is combined with a tracking dye prior to running in the gel. The material in this "tracking" lane may be bound by a nucleic acid staining dye such as an intercalator, and thus visualized, or it may be co-migrate with a tracking dye. In either instance, the gel itself may be dye-free, thereby ensuring that the desired material in the sample lane is ultimately harvested without dye.
Figure 20:
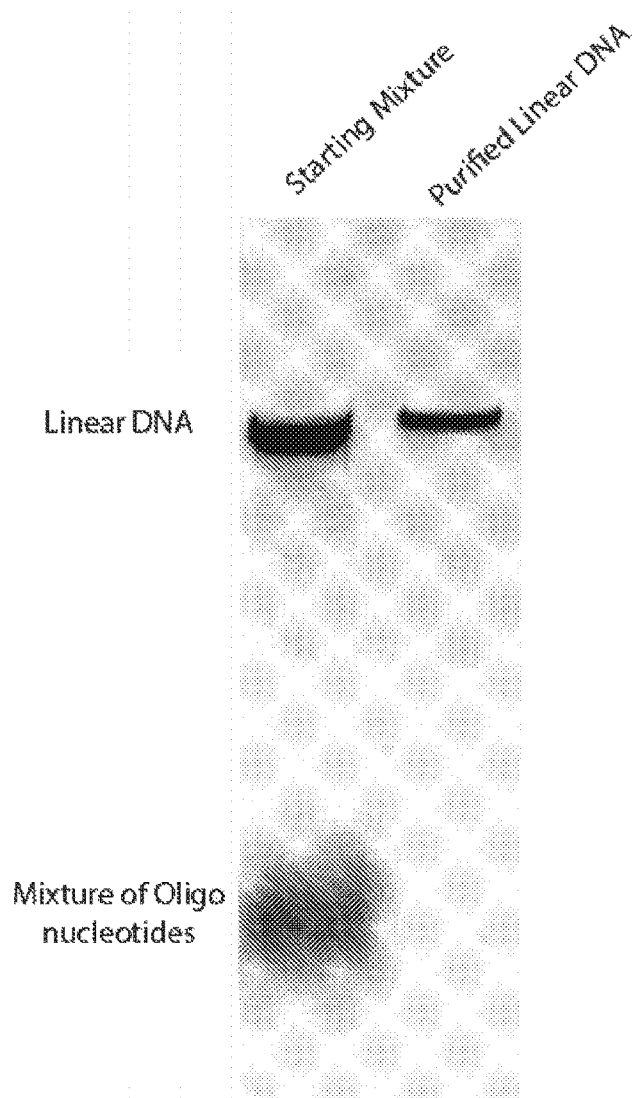
FIG. 20. Polyacrylamide gel electrophoresis analysis showing the purification of linear M13 DNA from a mixture that comprised the linear M13 DNA and oligonucleotides.

In still another embodiment, as shown in FIG. 19, instead of putting only tracking dye in a neighboring lane 1732, a small portion of the sample may be placed into the second lane with a DNA staining dye. In other words, a second lane may be used for visualization through fluorescence dye or DNA shadowing. In such embodiments, once the positions of the desired and undesired components 1740, 1742 relative to the first and second gel portions 1706a, 1706b are confirmed, the second gel portion 1706b may be removed, and the direction of the electric field may be reversed to cause the desired portion of the sample to migrate into the well. As will be appreciated, the stained dye loaded into the neighboring well will not be aspirated and is instead sacrificed for purposes of the purification process. FIG. 20 is an example in which small oligo nucleotide was purified from linear M13 DNA. As shown in this figure, a downstream agarose gel-electrophoresis analysis of the electro elution reverse gel electro-elution method showing linear DNA is purified from the starting mixture.

Thus, in a variation of the reverse gel electro-elution, visible gel tracking dyes (such as orange G, bromophenol blue, xylene cyanol, etc.) may be added to the sample. These gel tracking dyes are able to co-migrate between the desired and undesired material under the tuned gel condition (e.g., agarose percentage, temperature, applied voltage, etc.). In this way, material can be directly removed by slicing the gel at the appropriate location before the recovery reverse run is performed as shown in FIG. 18. In some instances, the co-migrating visible tracking dye is not mixed with the sample but is instead loaded into an neighboring lane on the same gel. In still another embodiment, an aliquot of the sample or a control sample is combined with a fluorescence dye or a DNA shadowing reagent such that migration of the bands of interest and those not of interest may be observed. This is illustrated in FIG. 19.

Reverse gel electro-elution was used to purify a linear M13 DNA from a mixture of oligonucleotides. The results are shown in FIG. 20, which is a downstream agarose gel electrophoresis analysis of the purified product obtained using reverse gel electro-elution.

Nanoswitch-Independent Analyte Detection

In general, any system that exhibits a detectable change in the presence of an analyte of interest could be used for detection. While the methods described here are primarily focused on attachment and purification, they could be used to detect (and/or quantify) these different nanoswitch states.

For example, in order to purify functionalized oligonucleotides from unfunctionalized oligo nucleotides, a gel shift assay may be used to quantify and separate out these two populations. A similar gel shift assay is contemplated for analyte detection. For example, if the goal is to detect the presence of an antibody, an oligo conjugated to the antigen may be mixed with the sample, and then run on a gel capable of separating out antibody-bound oligos from the original antigen-oligos. The presence and brightness of a shifted band (imaged by staining the DNA and/or the protein) would indicate the presence and amount of antibody present. Variations to this approach include replacing the short oligo with a longer piece of double-stranded DNA coupled to an antigen, which would increase the brightness of the shifted band but might decrease the degree of gel shift. This assay could also be reversed whereby the antibody is coupled to the oligo and the antigen (analyte) is detected through a gel shift that results from a binding event between the analyte and the antibody, provided this shift can be resolved. More generally, other separation methods capable of separating analyte-bound oligos from bare oligos, such as size exclusion chromatography as described above, could also be used to detect analytes through their binding to functionalized oligos.

Thus, this disclosure contemplates detection methods that may be independent of the nanoswitch loop formation methodology described herein, in some instances.

Products Including Kits

Also provided herein are the nanoswitches, polymers, polymer pairs, and kits comprising nanoswitches, polymers or polymer pairs along with specific reagents for analyte detection. The polymers may be conjugated to binding partners of interest or they may be provided with binding partners of interested with or without the reagents required to conjugate the two. Thus, for example, in some embodiments, a polymer conjugated to two binding partners which bind to the same analyte is provided. In some embodiments, two polymers each conjugated to a binding partner, wherein both binding partners bind specifically to the same analyte. In still other embodiments, provided are oligonucleotides that are bound to binding partners of interest and "scaffold" nucleic acids to which such oligonucleotides hybridize in a sequence specific manner to form one version of the polymers of this disclosure. Similarly nanoswitches may be provided fully assembled or scaffolds and oligonucleotides with or without conjugated binding partners may be provided. Instructions for conjugation of binding partners to polymers such as nucleic acids may also be provided. Instructions for incubating nanoswitches or polymers with samples including complex samples may also be provided.

Gel Analysis and Band Quantification

To determine the concentration of the analyte in a sample, the above method is performed and the intensity of the looped band after gel electrophoresis is determined. The first step involves accurately predicting the location and span of the looped band in the sample lane on the gel. This can be done in multiple ways, including but not limited to using a control lane on the same gel with known concentration of analyte spiked in as a reference, or previous gel runs with the same gel running conditions and control lanes containing known amounts of analyte as a reference after normalizing length by the linear band migration distance. The location and span in the reference lanes are given by fitting the filtered intensity to a Skew Normal distribution with an offset. To filter the data, each individual row was median filtered to remove noise, though other filters may also be used. We used a linear offset, but other functions that match the background of the intensity distribution could be used, such as multiple piecewise linear functions, an exponential decay plus a linear offset, or a Gaussian tail. The fit using a single linear offset results in 4 parameters for the skew normal distribution: the location scale w, skewness a, and amplitude A, and 2 parameters for the linear offset, the slope m and constant parameter b. The full equation is given by:

$$Ae^{-\left(\frac{x-\xi}{w}\right)^2}\left(1 + \text{erf}\left(\alpha\frac{x-\xi}{w}\right)\right) + mx + b$$

Figure 21:
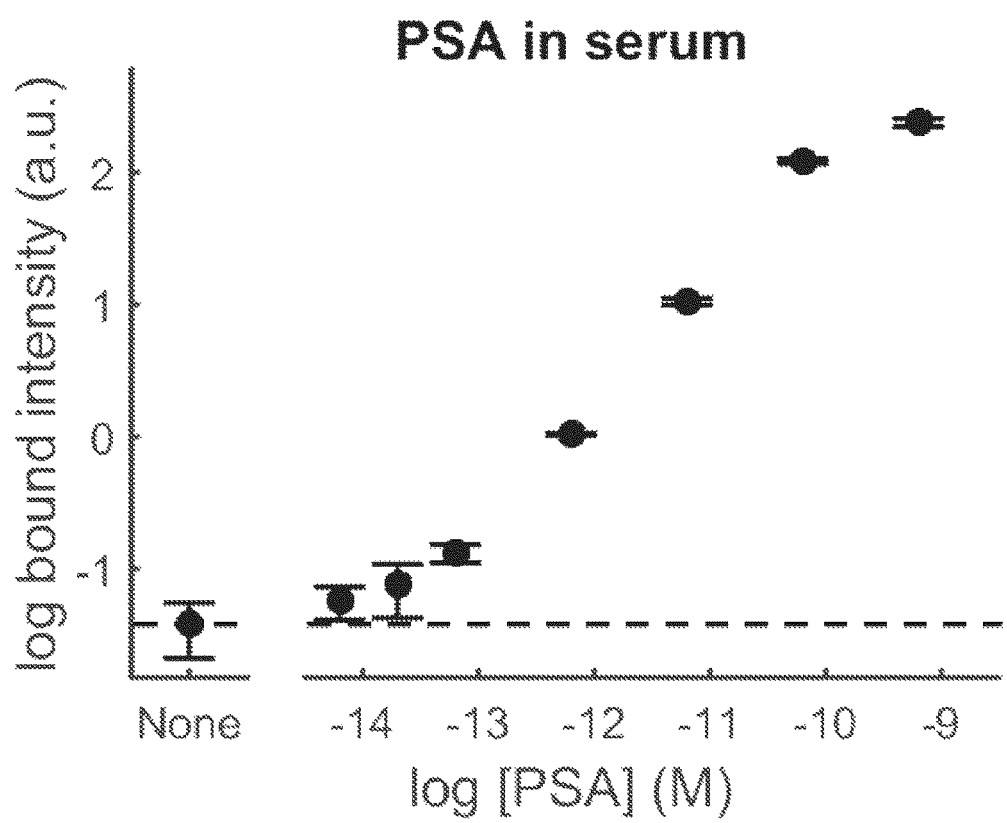
FIG. 21. DNA nanoswitch detection of human prostate-specific antigen (PSA) in complex fluids. Log-log plots of average bound intensity per lane as a function of concentration for PSA in 20% serum. Results are for 4 µl of sample run in one gel lane. Error bars are the s.d., with the background given by the dashed line, with 4 replicates per data point.

The location parameter is given relative to the edge of the well. The overall intensity of the band is given by Aw. Next, we fit the same function to the sample lane, with the location $\xi$, scale w, and skewness $\alpha$ parameters fixed. The concentration of analyte in the sample is then given by the amplitude A in the sample as compared to the reference lanes. Specifically, the predicted concentration is given by the intersection of the sample amplitude A with a curve of amplitude vs concentration for reference lanes having known concentrations of analyte. FIG. 21 demonstrates the use of this gel analysis with a background given by a decaying exponential intensity from the well, a decaying Gaussian tail from the linear band, and a constant offset to measure the bound intensity for a concentration series of human prostate-specific antigen (PSA) spiked into 4 μl of fetal bovine serum.

EXAMPLES

Antibody Coupling

Antibodies against PSA and TSH (Biospacific) were buffer exchanged to 10 mM sodium bicarbonate using two Zeba columns (Thermo Fisher Scientific) and were coupled to azide-modified oligonucleotides (Integrated DNA technologies) using DBCO-PEG4-NHS ester linkers (Sigma). Specifically, we mixed together antibody at a final concentration of ~3.6 uM, an equimolar amount of linker and 5× excess of oligonucleotide in a 10 mM sodium bicarbonate buffer and incubated at room temperature for 3 hours. Antibody pairs were coupled to the oligonucleotides CTCAAATATCAAACCCTCAATCAATATCT\3AzideN\ (SEQ ID NO: 10) and \5AzideN\TTTTGAAGCCTTAAA-TCAAGATTAGTTGCT (SEQ ID NO: 11). Antibodies were then purified from excess oligonucleotides and linkers using the Thunder-Link Conjugate Clean Up Reagent (Innova Biosciences) and resuspended in NEB buffer 2. Antibody coupling and purification were confirmed using 4-20% TBE polyacrylamide gel (Bio-Rad) stained with Krypton Fluorescent Protein Stain (Thermo Fisher Scientific).

Nanoswitch Formation

DNA nanoswitches were created as described in Koussa et al. 2015, with the antibodies added at 37° C. during the hybridization protocol. After hybridization, nanoswitches were purified from excess antibodies and oligonucleotides by using the BluePippin with a 0.75% agarose gel cassette, the S1 marker, and the high pass protocol with a 4500 bp cutoff. Alternatively, PEG precipitation can be used for purification (Koussa et al. 2015). After purification, nanoswitches were diluted to a concentration of 320 pM in 1×TBST. The purified nanoswitch solution is stable for months at 4° C.

Incubation and Gel Electrophoresis of Nanoswitch and Sample Mixture

The sample was mixed with nanoswitches to a final concentration of 160 pM and volume of 14 ul. When assaying serum or urine, EDTA was added to a final concentration of 100 mM. We mixed the samples in an Eppendorf Protein lobind tube, but the samples can also be mixed in Eppendorf lobind plates for a lower cost per sample. Then the mixture was incubated for 30 minutes at room temperature, unless otherwise specified. The mixture was then diluted by adding 1× volume of 0.5×TBE, a ficoll-based loading solution (Promega) was added, and if specified, 0.5 ul of 200×SYBR Gold and 0.5 ul of 1% Coomassie Brilliant Blue G-250 were added. The samples were then run on a 1.0% agarose gel for buffer and serum or a 0.7% agarose gel for urine. The gels were prestained with 0.6×SYBR gold and run on an Owl B1A Mini Gel Electrophoresis System (Thermo Fisher Scientific) at 300V for 11 minutes, unless otherwise specified. We used a custom comb to create wells of 3 mm by 5 mm.

Gel Imaging

Gels were imaged using a laser gel-scanner (GE Typhoon), as described in Koussa et al. 2015.

Secondary Structure Free Oligonucleotide and Target Region Selection and Use

Figure 4C:
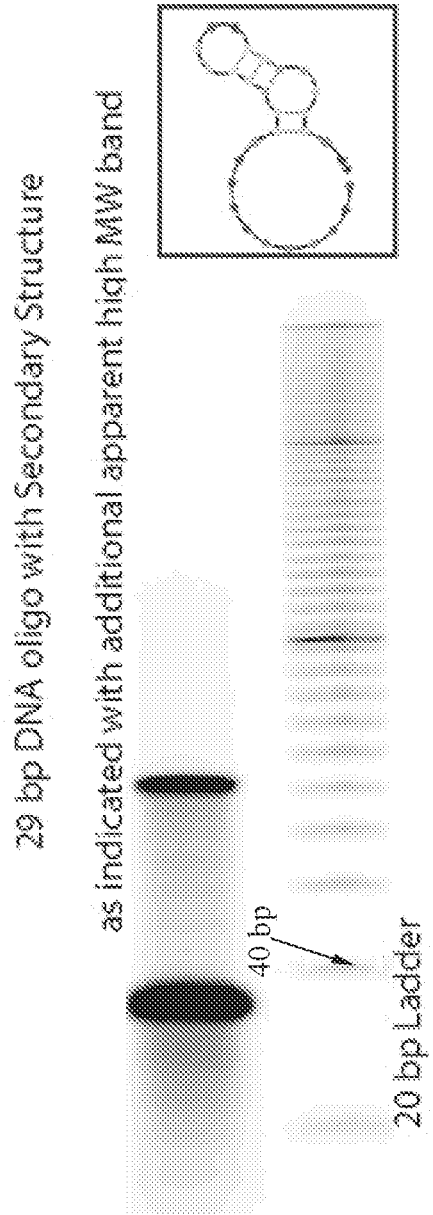

FIG. 4A shows an example of a 58 bp DNA oligo with a minimum free energy state containing no secondary structure at room temperature (25° C.) determined by NuPack sequence analysis program. Each base index is colored by the equilibrium probability of being in that particular state. This example oligo was used as the bridging oligo in the example of FIG. 5. FIG. 4B shows polyacrylamide gel electrophoresis of the oligo of the same sequence. FIG. 4C illustrates a complementary oligonucleotide from a previous target region design that has internal secondary structure in its population. An additional high MW band is apparent, presumably representing the hairpin-containing form of the oligonucleotide. The top insert is the likely minimum free energy structure predicted by NuPack sequence analysis program.

This approach was then applied to a nanoswitch designed to bind two bridging oligonucleotides, as illustrated schematically in FIG. 5. The experimental details are as follows:

Circular M13mp18 single-stranded DNA (ssDNA) (New England Biolabs, N4040S) was linearized by hybridizing a 40 bp oligo that created a double-stranded restriction site for the BtsCI enzyme (New England Biolab, R0647S). Subsequently, a set of complementary oligos (Integrated DNA Technologies) was hybridized onto the linear ssDNA. Functionalized oligos (biotinylated and digoxigenin-modified) were hybridized onto the 3' and 5' ends of the ssDNA respectively. The hybridization was carried out with 15 nM of linearized ssDNA and 10 molar excess of the complementary oligos in 1×NEBuffer 2 with a temperature ramp from 90 to 20° C. (−1° C./minute) in a thermocycler. After this initial hybridization, two specific single-stranded target regions free of secondary structure remained, which were bridged by two complementary oligos to form the final looped construct with the complementary bridge oligos secondary structure free as well. This secondary hybridization step (FIG. 5) was carried out at a final nanoswitch concentration of 250 pM with a 1.25 molar excess of the bridge oligos in 1×NEbuffer 2 at room temperature for 30 minutes. Looping of the nanoswitch was verified using gel-shift assays. A DNA nanoswitch loop was also constructed using previous approaches. This nanoswitch has secondary structure in the target regions and in the complementary oligonucleotides (as shown in FIG. 4C). Moreover, a temperature ramp from 90 to 20° C. (−1° C./minute) was used in the secondary hybridization process to achieve the maximum loop yield.

FIG. 5 demonstrates gel electrophoresis of the DNA nanoswitch showing loop formation. Lane 1 is the 1 kbp extension ladder (Invitrogen, 10511-012). Lane 2 is a nanoswitch having oligos that contain secondary structure and hybridized under linear ramping from high temperature (90 to 20° C. at 1° C./min.). Lane 3 is the nanoswitch made using target regions lacking secondary structure and hybridized under room temperature for 30 min. Lane 4 is the linear M13 scaffold without the bridging oligo that is required to form the loop.

Purification of DNA Nanoswitch Construct

A robust and effective way of removing those impurities from a nanoswitch reaction solution is to utilize a gel electrophoresis technique. FIG. 9 shows the separation that can be achieved using a BluePippin™ device. A dye-free 0.75% agarose, low-voltage protocol was used with Marker S1 in the BluePippin™ system to purify DNA nanoswitches. The high-pass protocol was used which involved eluting DNA that was more than 5 kb in length.

Example Involving Von Willebrand Factor A2 Domain Crosslinked to Secondary Structure Free Oligonucleotide Using Thiol-Based Copper-Free Click Chemistry, Purified Using His-Tag, and DNA Nanoswitch Formation Using Two-Point Attachment at Room Temperature von Willebrand factor A2 domain with cysteine residues engineered on the N and C terminal of the protein was previously described (Zhang et al. 2009). We crosslinked a secondary structure free DNA nanoswitch oligonucleotide onto each terminus through thiol-based copper-free click chemistry.

Coupling Protocol:
(1) Mix 60 µL of A2 solution (25 µM A2 protein, 20 mM Tris, 50 mM NaCl, pH 7.4) with 6.67 µL of 1 mM Tri(2-carboxyethyl)phosphine (TCEP, pH 7.4). The final concentration of TCEP is 100 µM. The mixture is incubated for 1 hour at room temperature to reduce the cysteine residues.
(2) Add 4.75 µL of freshly prepared reagent dibenzocycloctyne-PEG4-maleimide dissolved in anhydrous DMSO (15 mM). Flush the vial with inert gas, and incubate for 2 hours at room temperature or overnight in 4° C. The final concentration of the reagent is 1 mM.
(3) Use 7 k-cut-off Zeba desalting column (pre-equilibrate with 20 mM Tris, 50 mM NaCl, pH 7.4 azide-free buffer) to remove the excess reagent. Alternatively, dialysis may be performed.
(4) Into the mixture, suspend 15 nanomole of azide-oligonucleotide (final concentration of 250 µM of azide oligonucleotide, 10×molar excess of A2 protein) and incubate for 2 hours at room temperature or 6 hours in 4° C.

Azide-oligonucleotide sequence:
(SEQ ID NO: 12)
5'-CTCAAATATCAAACCCTCAATCAATATCT3'Azide His-tag Purification Protocol:
(1) Suspend the reaction mixture to 400 µL with binding buffer (20 mM Tris, 500 mM NaCl, 20 µM NiCl2, pH 8.0).
(2) Add 50 µL of washed Ni Sepharose excel bead solution (GE, pre-washed with binding buffer) and incubate in 4° C. for 1 hour with mixing.
(3) Spin the beads down for 30 seconds, and remove the supernatant.
(4) Suspend the beads with 100 µL wash buffer (20 mM Tris, 500 mM NaCl, 20 µM Imidazole, 0.01% Tween, pH 8.0). Spin the beads down immediately, and remove the supernatant.
(5) Repeat step (4) 3 more times.
(6) Suspend the beads with 100 µL elution buffer (20 mM Tris, 50 mM NaCl, 300 mM imidazole, 0.01% Tween, pH 8.0), and incubate for 5 minutes.
(7) Spin the beads down for 30 seconds, and remove the supernatant. The supernatant contains the purified A2-oligonucleotide product.
(8) Repeat (6) and (7) for a second elution.

Figure 11:
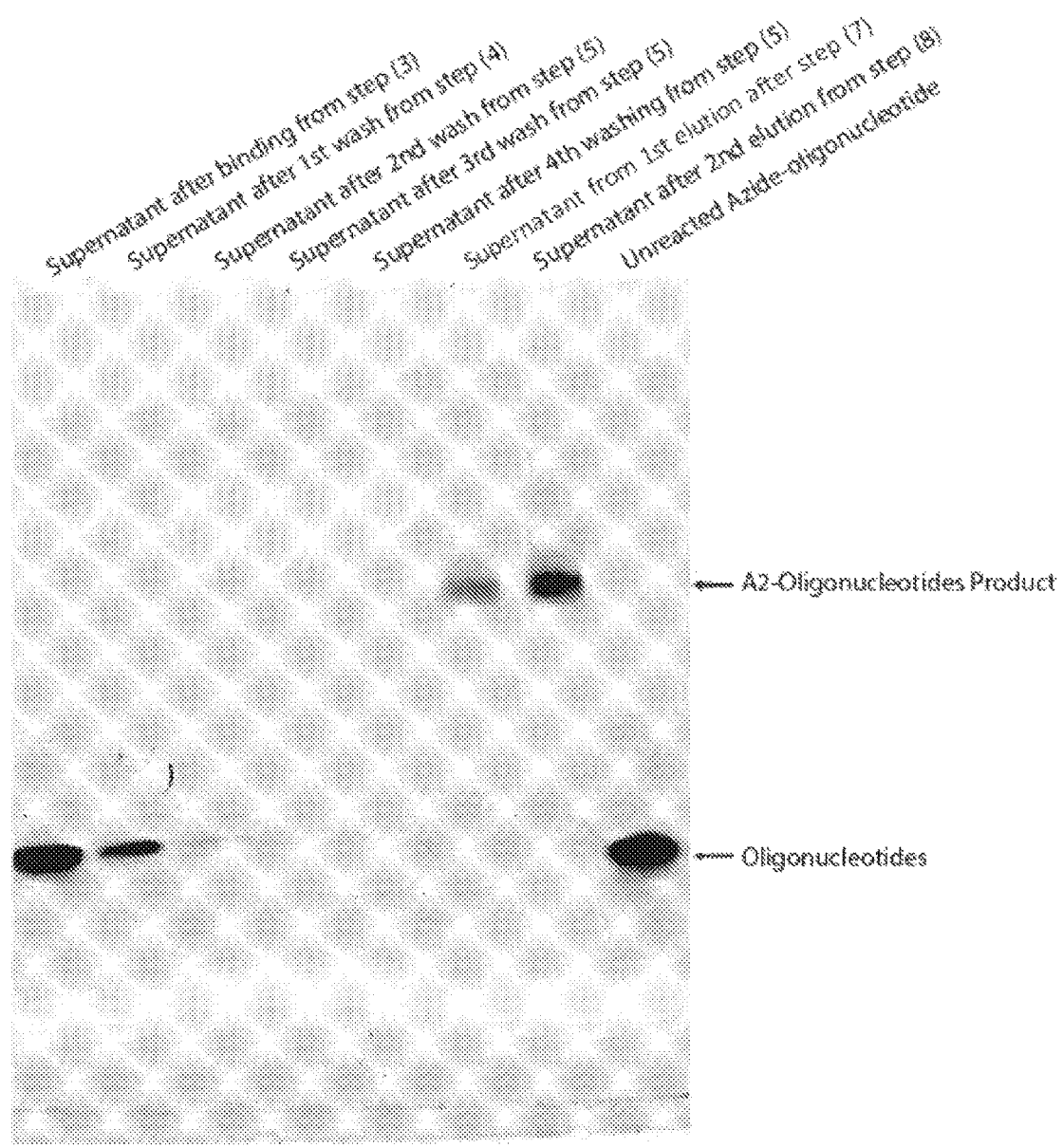
FIG. 11. Gel electrophoresis analysis of the thiol-based copper-free click chemistry reaction and product purification in the von Willebrand factor A2 two-point attachment example.

Polyacrylamide gel electrophoresis analysis of the reaction and product purification is provided in FIG. 11.

DNA Nanoswitch Loop Formation with Two-Point Attachment:

Circular M13mp18 single-stranded DNA (ssDNA) (New England Biolabs, N4040S) was linearized by hybridizing a 40 bp oligo that created a double-stranded restriction site for the BtsCI enzyme (New England Biolab, R0647S). Subsequently, a set of complementary oligos (Integrated DNA Technologies) was hybridized onto the linear ssDNA. The hybridization was carried out with 15 nM of linearized ssDNA and 10 molar excess of the complementary oligos in 1×NEBuffer 2 with a temperature ramp from 90 to 20° C. (−1° C./minute) in a thermocycler.

This initial hybridization contained a bridging oligonucleotide at 15 nM concentration. This oligonucleotide comprised a complementary sequence to the azide-oligonucleotide and complementary sequence to one specific target region.

After this initial hybridization, two specific single-stranded target regions were hybridized with the same complementary sequence azide-oligonucleotide, which can bridge the A2-oligonucleotide product. This hybridization step is carried out at room temperature for 30 minutes at a 2 nM construct and A2-oligonucleotide concentration.

Figure 12:
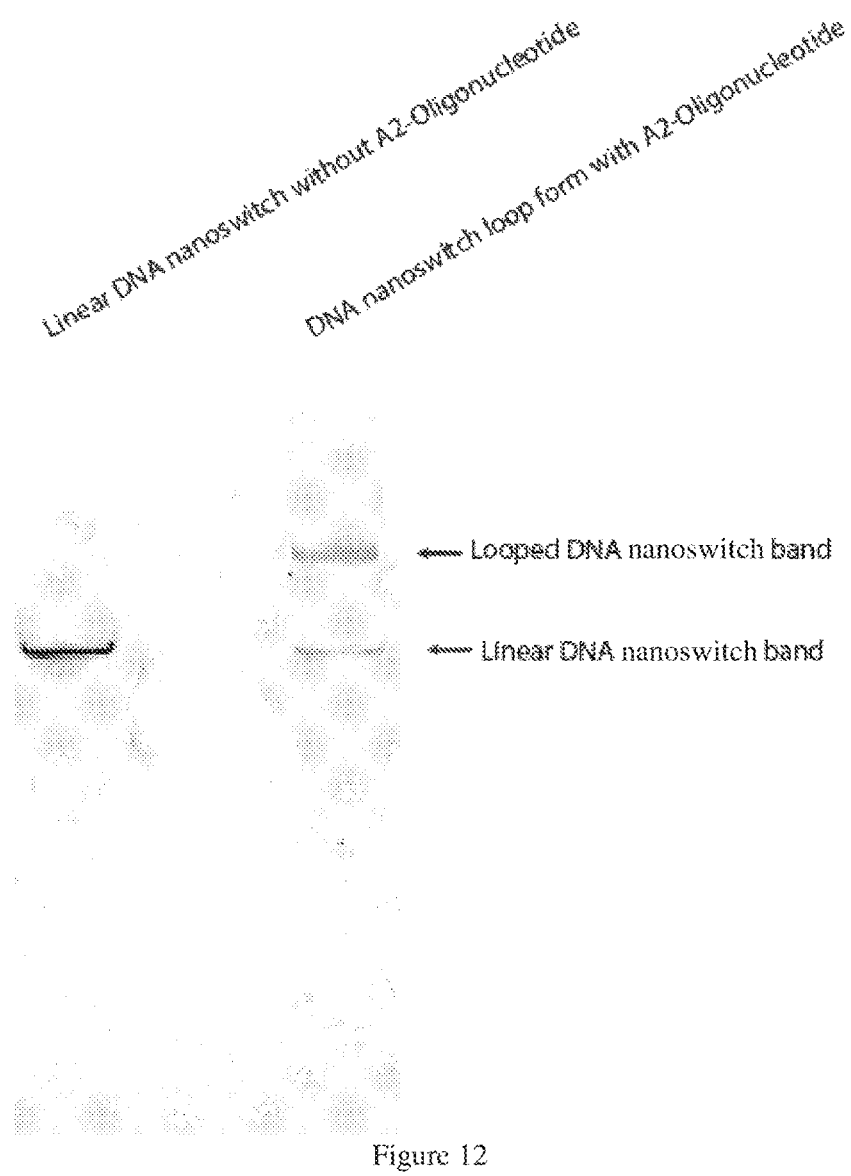
FIG. 12. Gel electrophoresis analysis of looped DNA nanoswitches formed using the two-point attachment strategy and A2-oligonucleotides.

The ability of the resultant nanoswitch to form a looped configuration is shown in FIG. 12. The looped and linear forms of the nanoswitch are readily apparent.

Anti-Fluorescein Antibody Crosslinked to Secondary Structure Free Oligonucleotide Through Amine-Based Copper-Free Click Chemistry, and Purified Using Size Exclusion Chromatography In this example, we crosslinked fluorescein antibody (Goat/IgG, polyclonal, ThermoFisher #A-11095) to a secondary structure free oligonucleotide via primary amines of the protein using amine-based copper-free click chemistry. After purification of the crosslinked product, we formed the DNA Nanoswitch loop with fluorescein oligonucleotide.

Coupling Protocol:
(1) Use Zeba desalting column (or dialysis) to exchange the 120 µL stock fluorescein antibody (1 mg/ml, 6 µm) into primary amine- and azide-free buffer such as 100 mM potassium phosphate, 150 mM NaCl, pH 8.0.
(2) Add 1.1 µL of freshly prepared reagent dibenzocycloctyne-PEG4-N-hydroxysuccinimidyl ester dissolved in anhydrous DMSO (2 mM). Flush vial with inert gas, and incubate for 1 hour at room temperature or 6 hours in 4° C. The final concentration of the reagent is roughly 3 molar excess of the antibody. For mono-labeling, increase the molar excess only if necessary.

(3) Use Zeba desalting column (or dialysis) to exchange the activated fluorescein antibody (1 mg/ml, 6 μm) into primary amine- and azide-free buffer such as 100 mM potassium phosphate, 150 mM NaCl, pH 7.4.

(4) Use the mixture to suspend 21.6 nanomole of azide-oligonucleotide (final concentration: 250 μM of azide oligonucleotide, 30×molar excess of antibody protein) and incubate for 2 hours at room temperature or 6 hours in 4° C.

Figure 13:
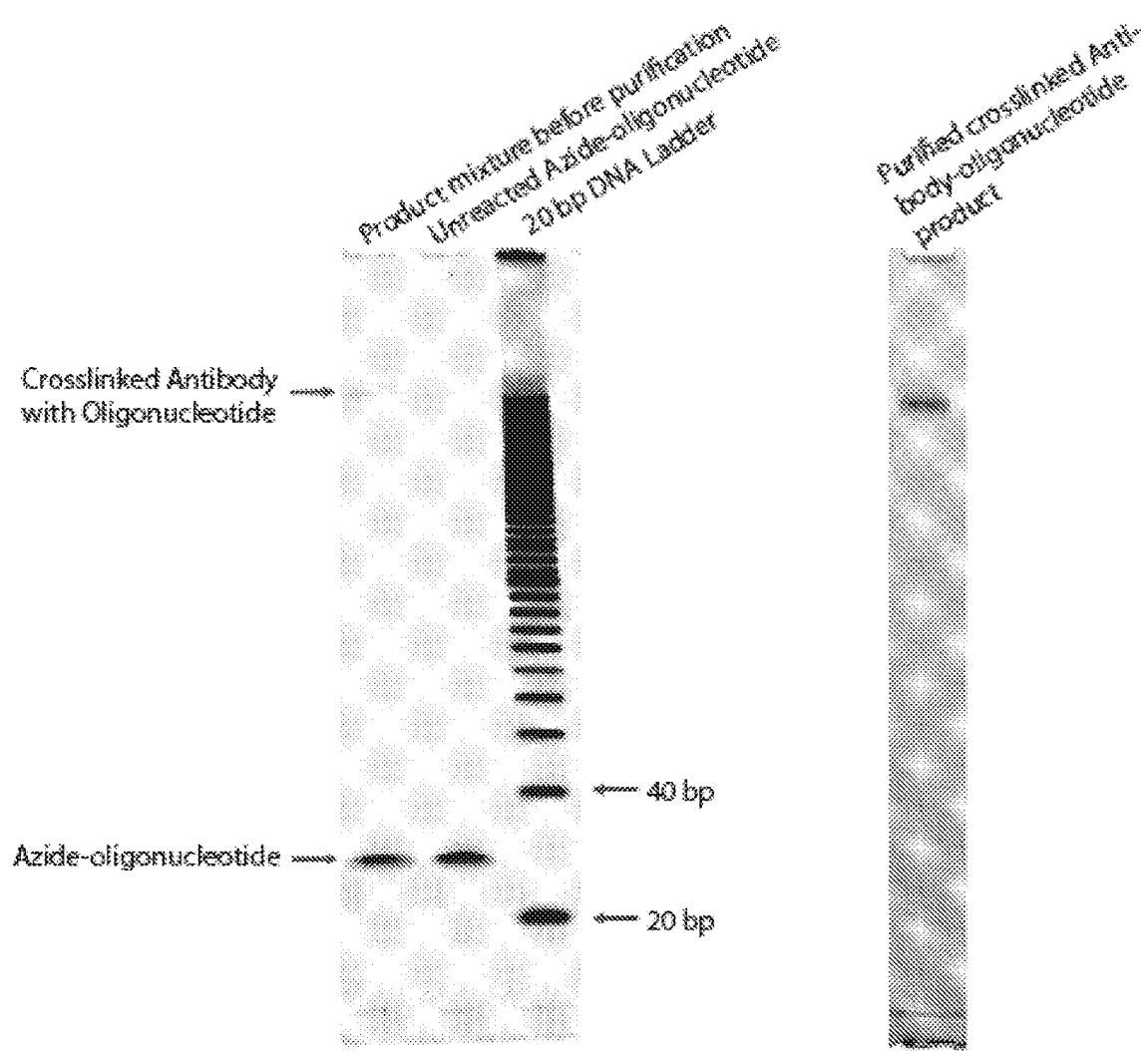
FIG. 13. Gel electrophoresis analysis of an elution of nucleic acids in the anti-fluorescein antibody exemplification.

Azide-oligonucleotide sequence:
(SEQ ID NO: 13)
5'-CTCAAATATCAAACCCTCAATCAATATCT-3'Azide Purification Using Size Exclusion Chromatography
(1) Equilibrate with 2 column volumes of Superdex 200 increase 10/300 gl with the desire final buffer such as 100 mM potassium phosphate, 150 mM NaCl, pH 7.4.
(2) Collect the elution and use polyacrylamide gel electrophoresis to identify the elution with the A2-oligonucleotide product The polyacrylamide gel electrophoresis analysis of the elution is shown in FIG. 13.

DNA Nanoswitch Loop Formation with Fluorescein and Anti-Fluorescein Antibody:

Circular M13mp18 single-stranded DNA (ssDNA) (New England Biolabs, N4040S) was linearized by hybridizing a 40 bp oligo that created a double-stranded restriction site for the BtsCI enzyme (New England Biolab, R0647S). Subsequently, a set of complementary oligos (Integrated DNA Technologies) was hybridized onto the linear ssDNA. The hybridization was carried out with 15 nM of linearized ssDNA and 10 molar excess of the complementary oligos in 1×NEBuffer 2 with a temperature ramp from 90 to 20° C. (−1° C./minute) in a thermocycler.

This initial hybridization contains the fluorescein-functionalized oligonucleotide at 15 nM concentration. This will bind with the antibody to form the DNA nanoswitch loop.

After this initial hybridization, a single-stranded target region that is complementary to the azide-oligonucleotide will remain. We then hybridized the crosslinked anti-fluorescein antibody oligonucleotide to the construct at room temperature for 30 minutes at a 2 nM construct and anti-fluorescein antibody oligonucleotide concentration.

Figure 14:
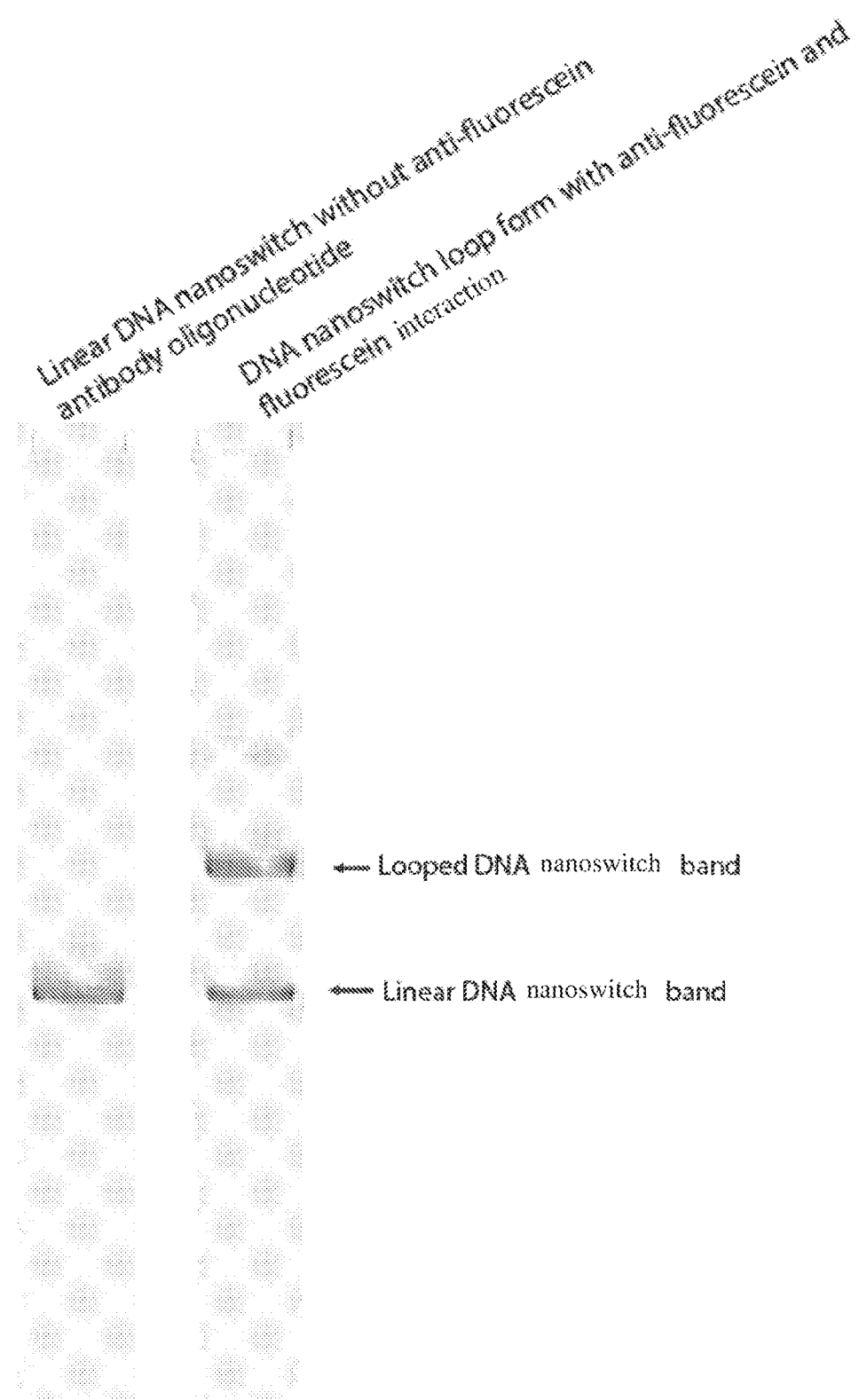
FIG. 14. Gel electrophoresis analysis of DNA nanoswitch loop formed with the fluorescein and anti-fluorescein technique.

FIG. 14 shows the electrophoretic pattern in the absence and presence of fluorescein.

REFERENCES

Banoo S. et al. Nat Rev Microbiol 4, S21-31 (2006).
Lequin, R. M. Clin Chem 51, 2415-2418 (2005).
Koussa, M. A., Halvorsen, K., Ward, A. & Wong, W. P. Nat Methods 12, 123-126 (2015).
Halvorsen, K. Schaak, D. & Wong, W. P. Nanotechnology 22, 494005 (2011).
Zadeh, J. N. et al. Journal of computational chemistry 32, 170-173 (2011).
Koussa, M. A., Sotomayor, M. & Wong, W. P. Methods 67, 134-141 (2014).
Zhang, X., et al. Science 324, 1330-1334 (2009).
McDonell, M. W. et al. Journal of molecular biology, 1977. 110(1): p. 119-146.
Hansen, H. et al. Biotechniques, 1993. 14(1): p. 28-30.
Bellot, G. et al. Nature methods, 2011. 8(3): p. 192-194.
Hassur, S. M. et al. Analytical biochemistry, 1974. 59(1): p. 162-164.
Thuring, R. et al. Analytical biochemistry, 1975. 66(1): p. 213-220.
Ravanat, J. L. et al. Journal of Photochemistry and Photobiology B: Biology, 2001. 63(1): p. 88-102.

Various aspects of embodiments may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Also, embodiments may be embodied as a method, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

The phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Having thus described at least one illustrative embodiment of the invention, various alterations, modifications, and improvements will readily occur to those skilled in the art. Such alterations, modifications, and improvements are intended to be within the spirit and scope of the invention. Accordingly, the foregoing description is by way of example only and is not intended as limiting.

What is claimed is:

1. A method for detecting an analyte in a sample comprising combining a sample with (a) a first polymer conjugated to a first analyte-specific binding partner and (b) a second polymer conjugated to a second analyte-specific binding partner, under conditions that allow binding of the first and second analyte-specific binding partners to respective analytes, wherein the first and second analyte-specific binding partners are able to bind to a single analyte simultaneously,
- detecting a complex formed by the binding of the first polymer and the second polymer to the single analyte in the sample, through their respective analyte-specific binding partners, using gel electrophoresis, wherein presence of the complex is indicative of presence of the single analyte in the sample,
- wherein the sample is a blood, serum or urine sample, wherein the complex is detected in the presence of a nuclease inhibitor and a charged protein binding dye, and the single analyte is a protein or a peptide, and
- wherein the first and second polymers are not bound to each other, directly or indirectly, prior to binding to the single analyte.

2. The method of claim 1, wherein the first and second polymers are nucleic acids, and the sample and first and second polymers are combined in the presence of a nucleic acid binding dye, EDTA and a charged protein binding dye.

3. The method of claim 1, wherein the sample is a serum sample.

4. The method of claim 1, wherein the sample is a blood sample.

5. The method of claim 1, wherein the sample is a filtered blood sample.

6. The method of claim 1, wherein the sample is a lysed blood sample.

7. The method of claim 1, wherein the charged protein binding dye is negatively charged.

8. The method of claim 1, wherein the charged protein binding dye is positively charged.

9. The method of claim 1, wherein the first and second analyte-specific binding partners are identical.

10. The method of claim 1, wherein the first and second analyte-specific binding partners are different.

11. The method of claim 1, wherein the first and second analyte-specific binding partners bind to an identical epitope that is present at least twice in the analyte.

12. The method of claim 1, wherein the first and second analyte-specific binding partners are antibodies or antigen-binding antibody fragments.

13. A method for detecting an analyte in a sample comprising
- combining a sample with (a) a first polymer conjugated to a first analyte-specific binding partner and (b) a second polymer conjugated to a second analyte-specific binding partner, under conditions that allow binding of the first and second analyte-specific binding partners to respective analytes, wherein the first and second analyte-specific binding partners are able to bind to a single analyte simultaneously,
- detecting a complex formed by the binding of the first polymer and the second polymer to an analyte in the sample, through their respective analyte-specific binding partners, wherein presence of the complex is indicative of presence of the analyte in the sample,
- wherein the complex is detected in the presence of a nuclease inhibitor and a charged protein binding dye,
- wherein the first and second polymers are not bound to each other, directly or indirectly, prior to binding to the single analyte, and
- wherein the nuclease inhibitor is EDTA, the analyte in the sample is Early Pregnancy Factor (EPF) and the sample is a urine sample.

14. The method of claim 13, wherein the charged protein binding dye is negatively charged.

15. The method of claim 13, wherein the charged protein binding dye is positively charged.

16. The method of claim 13, wherein the first and second analyte-specific binding partners are different.

17. The method of claim 13, wherein the first and second analyte-specific binding partners are identical.

18. The method of claim 13, wherein the first and second analyte-specific binding partners bind to an identical epitope that is present at least twice in the analyte.

19. The method of claim 13, wherein the first and second analyte-specific binding partners are antibodies or antigen-binding antibody fragments.

20. The method of claim 13, wherein the first and second polymers are nucleic acids, and the sample and first and second polymers are combined in the presence of a nucleic acid binding dye, EDTA and a charged protein binding dye.

* * * * *

SEQUENCE LISTING

<160> NUMBER OF SEQ ID NOS: 13

<210> SEQ ID NO 1
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 1
ctgagtaatg tgtaggtaaa gattcaaaag ggtgagaaag gccggagaca gtcaaatcac    60

<210> SEQ ID NO 2
<211> LENGTH: 50
<212> TYPE: DNA
<213> ORGANISM: Artificial Sequence
<220> FEATURE:
<223> OTHER INFORMATION: Synthetic Polynucleotide

<400> SEQUENCE: 2
catcaccttg ctgaacctca aatatcaaac cctcaatcaa tatctggtca                 50

<210> SEQ ID NO 3
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 3
caatatatgt gagtgaataa ccttgcttct gtaaatcgtc gctattaatt aattttccct      60

<210> SEQ ID NO 4
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 4
ctgaacaaga aaataatat cccatcctaa tttacgagca tgtagaaacc aatcaataat       60

<210> SEQ ID NO 5
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 5
ttgtttaacg tcaaaaatga aaatagcagc ctttacagag agaataacat aaaaacaggg      60

<210> SEQ ID NO 6
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 6
ggtcatagcc cccttattag cgtttgccat cttttcataa tcaaaatcac cggaaccaga      60

<210> SEQ ID NO 7
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 7
gtttagtacc gccaccctca gaaccgccac cctcagaacc gccaccctca gagccaccac      60

<210> SEQ ID NO 8
<211> LENGTH: 50
<212> TYPE: DNA
<213> ORGANISM: Artificial Sequence
<220> FEATURE:
<223> OTHER INFORMATION: Synthetic Polynucleotide

<400> SEQUENCE: 8
aagaaccgga tattcattac ccaaatcaac gtaacaaagc tgctcattca    50

<210> SEQ ID NO 9
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 9
ccagaacgag tagtaaattg ggcttgagat ggtttaattt caactttaat cattgtgaat    60

<210> SEQ ID NO 10
<211> LENGTH: 29
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (29)..(29)
<223> OTHER INFORMATION: Modified by [3]AzideN

<400> SEQUENCE: 10
ctcaaatatc aaaccctcaa tcaatatct    29

<210> SEQ ID NO 11
<211> LENGTH: 30
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: Modified by [5]AzideN

<400> SEQUENCE: 11
ttttgaagcc ttaaatcaag attagttgct    30

<210> SEQ ID NO 12
<211> LENGTH: 29
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (29)..(29)
<223> OTHER INFORMATION: Modified by Azide

<400> SEQUENCE: 12
ctcaaatatc aaaccctcaa tcaatatct    29

<210> SEQ ID NO 13
<211> LENGTH: 29
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (29)..(29)
<223> OTHER INFORMATION: Modified by Azide -continued

<400> SEQUENCE: 13
ctcaaatatc aaaccctcaa tcaatatct          29